(12) United States Patent
Hergenrother et al.

(10) Patent No.: US 9,249,116 B2
(45) Date of Patent: Feb. 2, 2016

(54) ENZYME-ACTIVATING COMPOUNDS AND COMPOSITIONS

(71) Applicant: The Board of Trustees of the University of Illinois, Urbana, IL (US)

(72) Inventors: Paul J. Hergenrother, Champaign, IL (US); Howard S. Roth, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/417,524

(22) PCT Filed: Aug. 5, 2013

(86) PCT No.: PCT/US2013/053648
§ 371 (c)(1),
(2) Date: Jan. 26, 2015

(87) PCT Pub. No.: WO2014/022858
PCT Pub. Date: Feb. 6, 2014

(65) Prior Publication Data
US 2015/0210659 A1    Jul. 30, 2015

Related U.S. Application Data

(60) Provisional application No. 61/679,129, filed on Aug. 3, 2012.

(51) Int. Cl.
C07D 295/16 (2006.01)
C07D 295/15 (2006.01)
G01N 33/50 (2006.01)

(52) U.S. Cl.
CPC ............ *C07D 295/16* (2013.01); *C07D 295/15* (2013.01); *G01N 33/5011* (2013.01); *G01N 2500/02* (2013.01); *G01N 2500/10* (2013.01)

(58) Field of Classification Search
CPC ............................ C07D 295/15; C07D 295/16
See application file for complete search history.

(56) References Cited

U.S. PATENT DOCUMENTS

| | | |
|---|---|---|
| 2011/0257398 A1 | 10/2011 | Hergenrother et al. |
| 2012/0040995 A1 | 2/2012 | Hergenrother et al. |
| 2013/0096133 A1 | 4/2013 | Hergenrother |

FOREIGN PATENT DOCUMENTS

| | | | |
|---|---|---|---|
| CN | 101712655 | * | 5/2010 |
| CN | 101565409 B | | 9/2011 |

(Continued)

OTHER PUBLICATIONS

Hsu et al., "Parallel Synthesis and Biological Evaluation of 837 Analogues of Procaspase-Activating Compound 1 (PAC-1)" ACS Combinatorial Science, Oct. 18, 2011. 14: 44-50.

(Continued)

*Primary Examiner* — Valerie Rodriguez-Garcia
(74) *Attorney, Agent, or Firm* — Haukaas Fortius PLLC; Michael H. Haukaas

(57) ABSTRACT

The invention provides compounds and compositions useful for the modulation of certain enzymes. The compounds and compositions can induce of cell death, particularly cancer cell death. The invention also provides methods for the synthesis and use of the compounds and compositions, including the use of compounds and compositions in therapy for the treatment of cancer and selective induction of apoptosis in cells.

19 Claims, 10 Drawing Sheets

(56) References Cited

FOREIGN PATENT DOCUMENTS

| | | | |
|---|---|---|---|
| CN | 102838567 | * | 12/2012 |
| WO | 2007008529 A2 | | 1/2007 |
| WO | 2008134474 A2 | | 11/2008 |
| WO | 2010091382 A1 | | 8/2010 |
| WO | 2012080088 A1 | | 6/2012 |

OTHER PUBLICATIONS

International Search Report and Written Opinion for PCT/US2013/053648 dated Nov. 28, 2013, 8 pages.

* cited by examiner

ENZYME-ACTIVATING COMPOUNDS AND COMPOSITIONS

RELATED APPLICATIONS

This application is a National Stage filing under 35 U.S.C. §371 of International Application No. PCT/US2013/053648, filed Aug. 5, 2013, which claims priority under 35 U.S.C. §119(e) to U.S. Provisional Patent Application No. 61/679,129, filed Aug. 3, 2012, which applications are incorporated herein by reference in their entirety.

BACKGROUND OF THE INVENTION

Apoptosis is a process used by higher organisms to maintain homeostasis by removing cells that are in excess, damaged, or potentially dangerous. Caspase enzymes are a class of cysteine proteases that cleave cellular substrates after recognition sequences with C-terminal aspartate residues. The activation of caspase enzymes is critical for apoptosis. There are two canonical apoptotic pathways, differing in that the apoptosis-initiating stimulus is intracellular (intrinsic pathway) or extracellular (extrinsic pathway). These pathways converge at the cleavage of procaspase-3 to form the active caspase-3, the key "executioner" caspase that catalyzes the hydrolysis of hundreds of protein substrates, leading to cell death.

One of the hallmarks of cancer is the ability of cancer cells to evade apoptosis, allowing for unchecked proliferation. As such, reactivation of apoptosis in cells with defective apoptotic pathways is a promising anticancer strategy. Compounds such as p53-MDM2 disruptors (Nutlins), Bcl-2 inhibitors (ABT-737), and inhibitors of XIAP (SM-164) all act directly on proteins in the apoptotic cascade, inducing apoptosis and leading to death of cancer cells.

Complementary to the strategies described above, the direct activation of procaspase-3 with a small molecule has potential for personalizing cancer therapy. Procaspase-3 levels are elevated in certain cancers, including lymphomas, leukemias, melanomas, pancreatic cancer, liver cancers, lung cancers, breast cancers, and colon cancers. Due to the elevated levels of procaspase-3 in cancer cells, the requirement of caspase-3 activation for apoptosis, and the relative downstream location of procaspase-3 in the apoptotic cascade, induction of apoptosis by the direct activation of procaspase-3 is being actively explored as a personalized anticancer strategy. Accordingly, there is a need for new compounds that modulate procaspase-3 activity, particularly compounds that activate procaspase-3 and that are metabolically stable enough to be effective clinical therapies.

SUMMARY

Procaspase-Activating Compound 1 (PAC-1) is an ortho-hydroxy N-acyl hydrazone that enhances the enzymatic activity of procaspase-3 in vitro and induces apoptosis in cancer cells. An analogue of PAC-1, called S-PAC-1, was evaluated in a veterinary clinical trial in pet dogs with lymphoma and found to have considerable potential as an anticancer agent. With the goal of identifying more potent compounds in this promising class of experimental therapeutics, a combinatorial library based on PAC-1 was created, and the compounds were evaluated for their ability to induce death of cancer cells in culture. The compounds were evaluated for their ability to induce apoptosis in cancer cells and for their metabolic stability. The newly identified compounds can provide therapeutics for treatment of the many cancers that have elevated expression levels of procaspase-3.

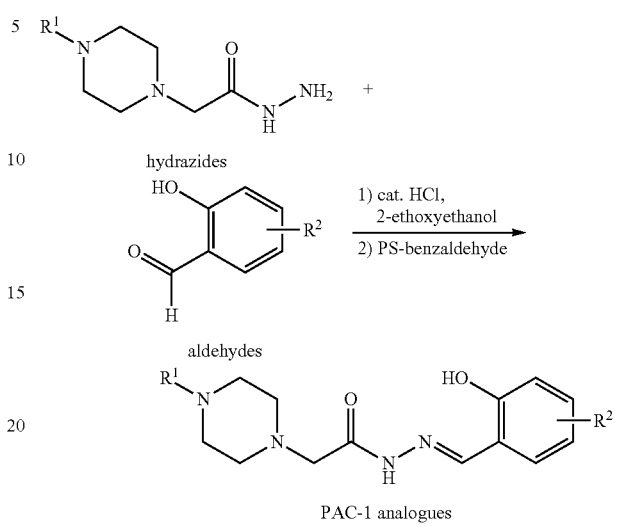

PAC-1 analogues

Compounds capable of activating enzymes that are often overexpressed in their inactive form in cancer cells have been discovered. The compounds can induce programmed cell death (apoptosis) in cancer cells, including those that have upregulated procaspase-3. Many cancers resist standard chemotherapy. The compounds described herein can take advantage of biological targets that may be upregulated in cancer cells and thus can be effective even in cells with defects in their apoptotic machinery. These compounds can also be successful in targeted cancer therapy by selectively killing cancer cells with comparably reduced adverse reactions to non-cancerous cells having lower levels of procaspase-3. These adverse reactions can include toxicity, particularly neurotoxicity.

Accordingly, the invention provides compounds of compound of Formula I:

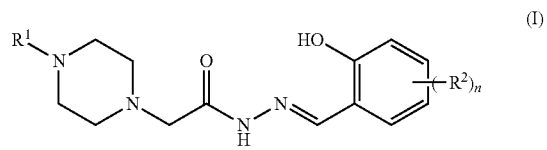

wherein
$R^1$ is an optionally substituted benzoyl, phenyl, (aryl)methylene, or (aryl)methine wherein the methine carbon is optionally substituted with phenyl;
n is 1, 2, 3, or 4; and
each $R^2$ is independently H, alkyl, alkoxy, hydroxy, carboxy, halo, amino, alkylamino, dialkylamino, trifluoromethyl, trifluoromethoxy, benzyl, benzyloxy, nitro, cyano (—CN), sulfonamide (—SO$_2$NH$_2$), 2-propenyl, acetylene, N-alkyl-triazole, or N-benzyl-triazole; or two $R^2$ groups form an ortho-fused benzo group;
or a pharmaceutically acceptable salt or solvate thereof.

In some embodiments, $R^1$ is benzoyl (Ph(C=O)—). In other embodiments, $R^1$ is a substituted benzoyl. The benzoyl group can be substituted with 1, 2, 3, or 4 $R^2$ groups. The variables $R^2$ can be ortho, meta, or para, or a combination thereof, to the carbonyl of the benzoyl group.

In some embodiments, n is 1 or 2. In other embodiments, n is 3 or 4. The variables $R^2$ can be ortho, meta, or para to the hydroxyl group of Formula I, or a combination thereof.

In some embodiments, $R^2$ is methyl, t-butyl, methoxy, hydroxy, fluoro, chloro, bromo, iodo, amino, ethylamino, diethylamino, trifluoromethyl, trifluoromethoxy, benzyl, benzyloxy, nitro, cyano, sulfonamide, 2-propenyl, acetylene, N-methyl-triazole, or N-benzyl-triazole. In various embodiments, n is 2 and two $R^2$ groups form an ortho-fused benzo group. In some embodiments, a substituent on an $R^1$ phenyl group can be a substituent $R^2$. In various embodiments, $R^2$ can independently be a substituent on an $R^1$ aryl group, including a benzoyl group, and such groups can have one to five $R^2$ substituents.

In some embodiments, n is 2 and each $R^2$ is t-butyl.

In some embodiments, n is 1 and $R^2$ is 2-propenyl.

In some embodiments, $R^1$ is a methoxy-benzyl; dimethoxy-benzyl; benzyloxy-benzyl; t-butyl-benzyl; naphthylmethylene; or ethyl-benzyl.

In certain specific embodiments, $R^1$ is 4-methoxy-benzyl; 2,5-dimethoxy-benzyl; 4-benzyloxy-benzyl; 4-t-butyl-benzyl; 2-naphthylmethylene; or 4-ethyl-benzyl.

In certain other specific embodiments, $R^1$ is:

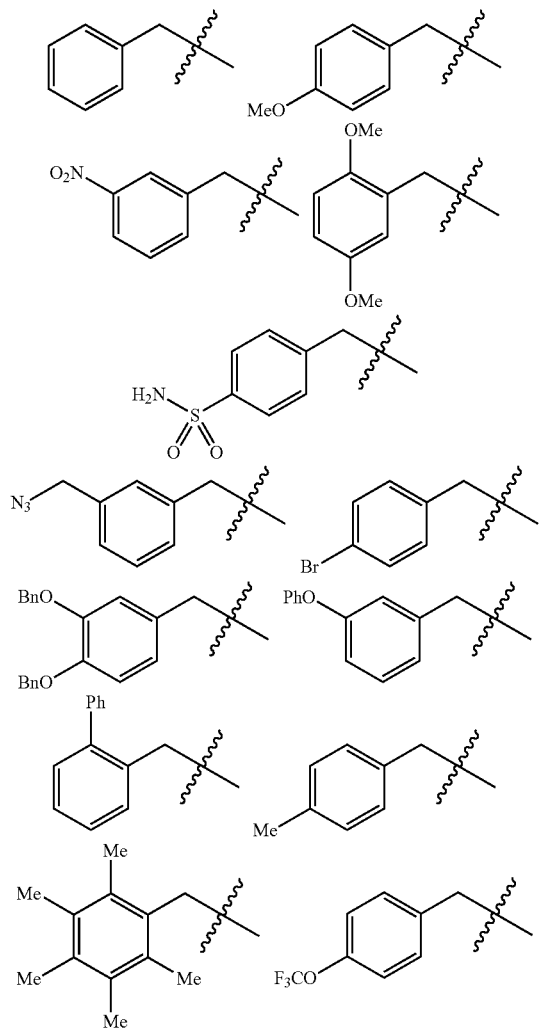

-continued

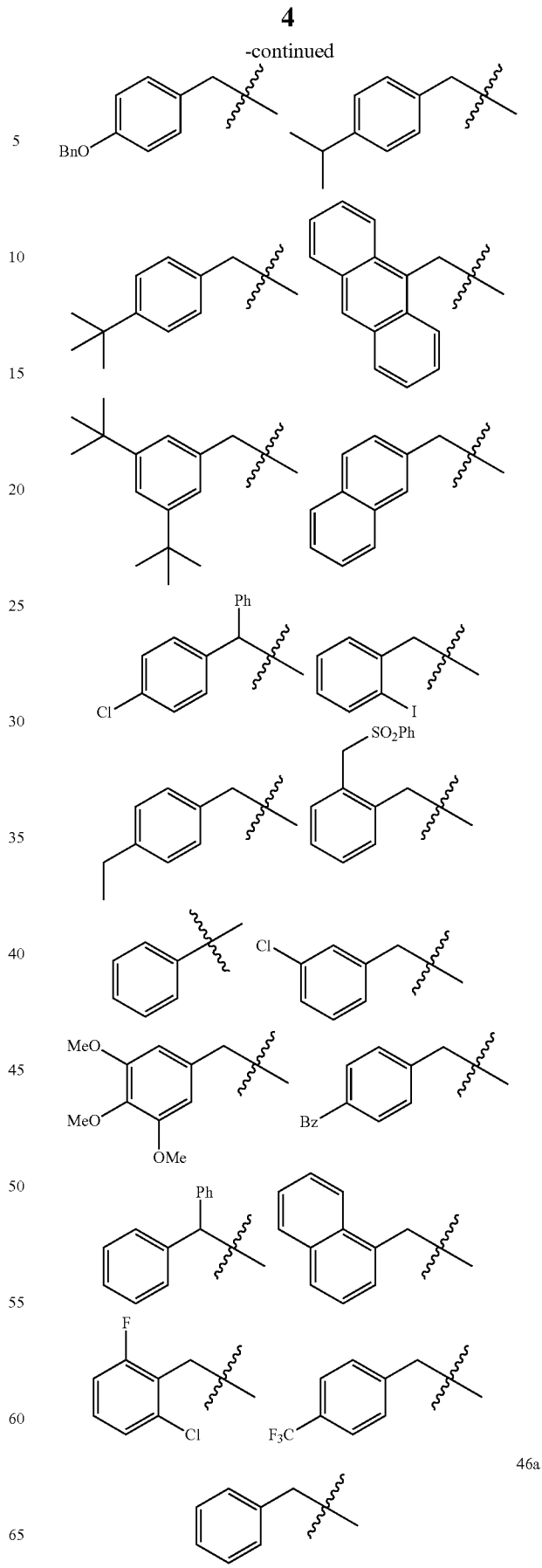

-continued

| | |
|---|---|
| 46b | 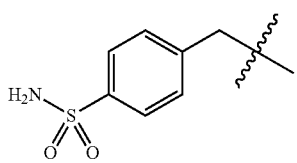 |
| 46c | 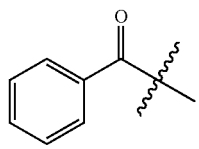 |
| 46d | 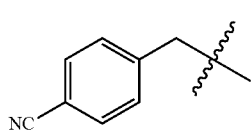 |
| 46e | 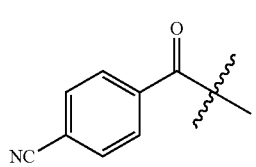 |
| 46f | 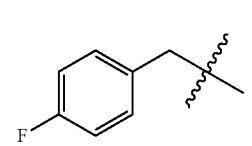 |
| 46g | 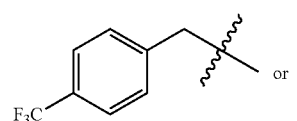 |
| 46h | 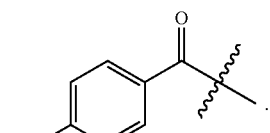 or |
| 46i | . |

In various specific embodiments, the compound is one or more of compounds 1-45 of Example 4, a compound of Table 1, or a pharmaceutically acceptable salt or solvate thereof. In other embodiments, the compound is a compound described herein wherein the methylene carbon attached to the distal piperazine nitrogen is substituted with an oxo group, for example:

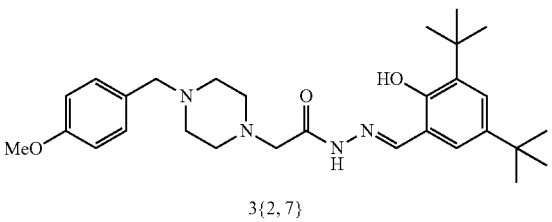

3{2, 7} provides support for:

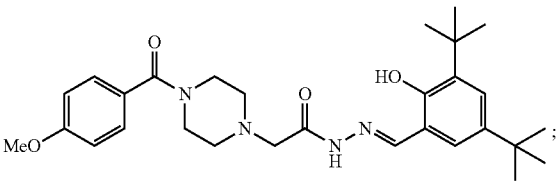

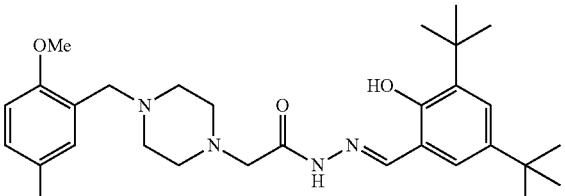

3{4, 7} provides support for:

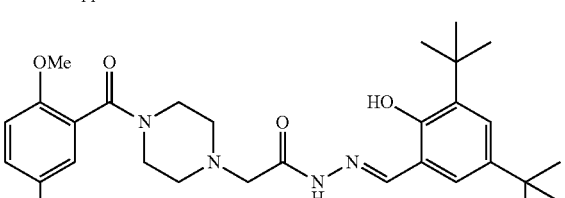

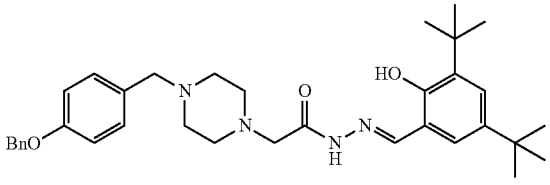

3{18, 7} provides support for:

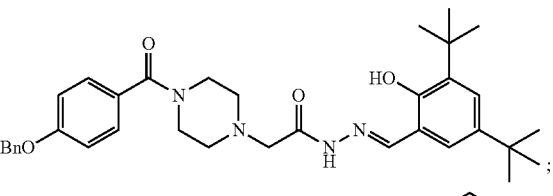

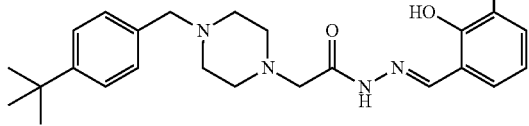

-continued provides support for:

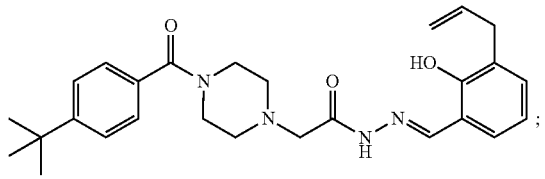

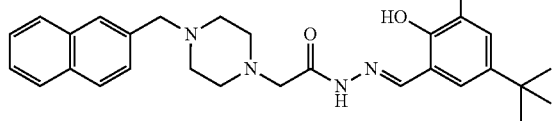

3{25, 7} provides support for:

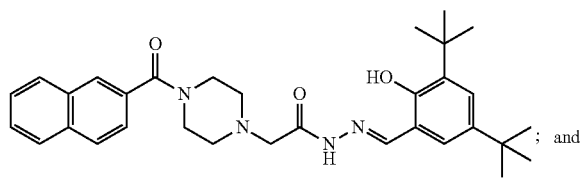

; and

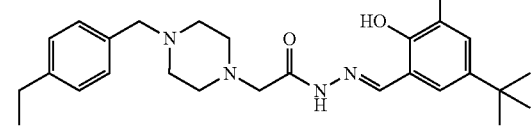

3{28, 7} provides support for:

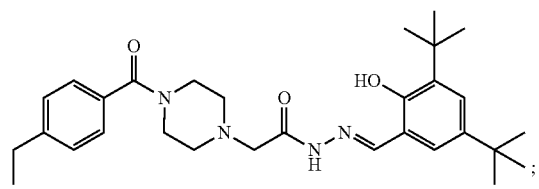

;

and the like, for each compound described or illustrated herein without an oxo group at the methylene carbon attached to the distal piperazine nitrogen. For example, in one embodiment, the compound is a compound of Formula (X):

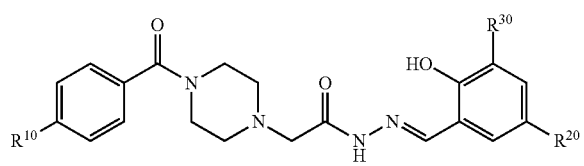

(X)

wherein
$R^{10}$ is H, F, Cl, Br, —$NO_2$, —CN, —$CF_3$, —$OCF_3$, or —$SO_2NH_2$;
$R^{20}$ is H, F, Cl, Br, —$NO_2$, —CN, —$CF_3$, —$OCF_3$, or —$SO_2NH_2$; and
$R^{30}$ is H, ($C_1$-$C_6$)alkyl, ($C_1$-$C_6$)alkenyl, or ($C_1$-$C_6$)alkoxy; or a pharmaceutically acceptable salt or solvate thereof.
In some embodiments, $R^{10}$ is H.
In some embodiments, $R^{10}$ is F, Cl, or Br.
In some embodiments, $R^{10}$ is —$NO_2$ or —CN.
In some embodiments, $R^{10}$ is —$CF_3$, —$OCF_3$, or —$SO_2NH_2$.
In some embodiments, $R^{20}$ is H. In some embodiments, $R^{20}$ is F. In some embodiments, $R^{20}$ is H or F.
In some embodiments, $R^{20}$ is F, Cl, or Br.
In some embodiments, $R^{20}$ is —$NO_2$ or —CN.
In some embodiments, $R^{20}$ is —$CF_3$, —$OCF_3$, or —$SO_2NH_2$.
In some embodiments, $R^{30}$ is H.
In some embodiments, $R^{30}$ is n-propyl.
In some embodiments, $R^{30}$ is 2-propenyl(allyl).
In some embodiments, $R^{10}$ can be $R^1$ as described above, and vice versa.
In some embodiments, $R^{20}$ can be $R^2$ as described above, and vice versa.
In some embodiments, $R^{30}$ can be $R^3$ as described above, and vice versa.

The invention also provides a pharmaceutical composition comprising a compound described herein and a pharmaceutically acceptable diluent, excipient, or carrier. In some embodiments, the compound induces death of cancer cells in culture.

The invention further provides a method of treating a cancer cell comprising (a) identifying a susceptibility to treatment of a cancer cell with a procaspase activator compound; and (b) exposing a cancer cell to an effective amount of the procaspase activator compound; wherein the procaspase activator compound is a compound described herein.

The invention additionally provides a method of inducing apoptosis in a cell comprising administering to a cell an effective amount of a compound described herein.

In some embodiments, the invention provides compounds and methods involving effective concentrations, such as about 10 nM to about 100 μM of the compound or formula. In some embodiments, the effective concentrations are from about 200 nM to about 5 μM. In another embodiment, the effective concentration is a value such as a 50% activity concentration in a direct procaspase activation assay, in a cell apoptosis induction assay, or in an animal clinical therapeutic assessment. In another embodiment, such value is less than about 200 μM. In various embodiments, the value is less than about 10 μM. In various embodiments, a compound can have significant metabolic stability. For example, at least about 30%, at least about 40%, at least about 50%, at least about 60%, at least about 70%, at least about 75%, at least about 80%, at least about 90%, or at least about 95% of a sample of the compound can remain after a 3-hour incubation in a liver microsome stability assay.

The invention therefore provides compounds, compositions, and methods of therapeutic treatment. In some embodiments, the inventions are applicable in the context of a variety of cancer diseases and cancer cell types such as breast, lymphoma, adrenal, renal, melanoma, leukemia, neuroblastoma, lung, brain, among others.

The invention provides the novel compounds described herein and the compounds of the Formulas described herein, intermediates for the synthesis of such compounds, as well as methods of preparing the compounds. The invention also provides compounds that are useful as intermediates for the synthesis of other useful compounds.

The also invention provides for the use of the compositions described herein for use in medical therapy. The medical therapy can be treating cancer, for example, lymphomas, leukemias, melanomas, pancreatic cancer, liver cancers, lung cancers, breast cancers, and colon cancers. The invention also provides for the use of a composition as described herein for the manufacture of a medicament to treat a disease in a mammal, e.g., cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
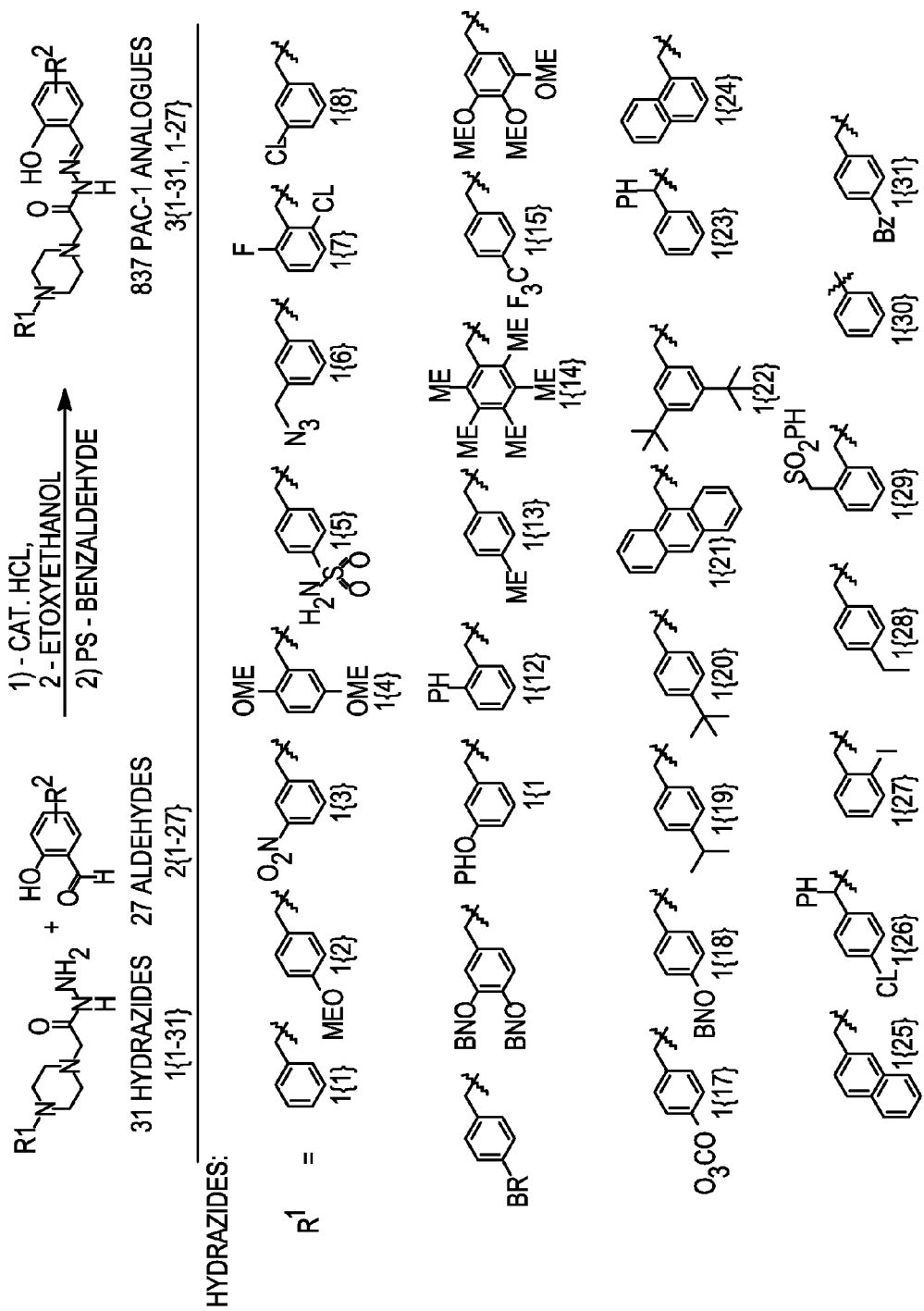
FIG. 1. Hydrazides used to construct a combinatorial library of PAC-1 analogues. Each $R^1$ benzyl hydrazide precursor can also be a corresponding $R^1$ benzoyl hydrazide precursor compound, in various embodiments.

In 2006, the discovery of Procaspase-Activating Compound 1 (PAC-1, Scheme A) was reported (Putt et al., *Nat Chem Biol* 2006, 2, 543-550). PAC-1 enhances the enzymatic activity of procaspase-3 in vitro, induces apoptotic cell death in cancer cells, and shows efficacy in multiple murine tumor models. Structure-activity relationship studies revealed that the activity of PAC-1 in vitro and in cell culture is dependent on the presence of the ortho-hydroxy N-acyl hydrazone moiety (Scheme A), a functional group known to participate in metal chelation. Indeed, zinc is a powerful inhibitor of procaspase-3 enzymatic activity, and the mechanism by which PAC-1 activates procaspase-3 in vitro is through chelation of inhibitory zinc from procaspase-3, which allows procaspase-3 to process itself to the active form. This same basic mechanism appears to be operational in cell culture as well: approximately 10% of cellular zinc is not bound tightly but exists as the "labile zinc pool". As zinc from the labile pool has been shown to co-localize with procaspase-3, it appears that PAC-1 chelation of this labile zinc inside the cells enhances procaspase-3 activity, leading to apoptosis.

Scheme A: PAC-1 and S-PAC-1, with the ortho-hydroxy N-acyl hydrazone motif, and corresponding benzoyl (Bz) derivatives.

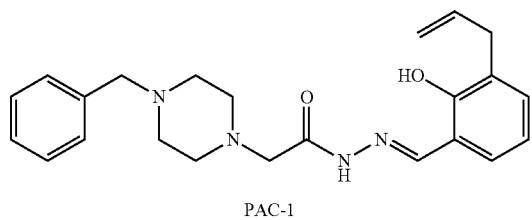

PAC-1

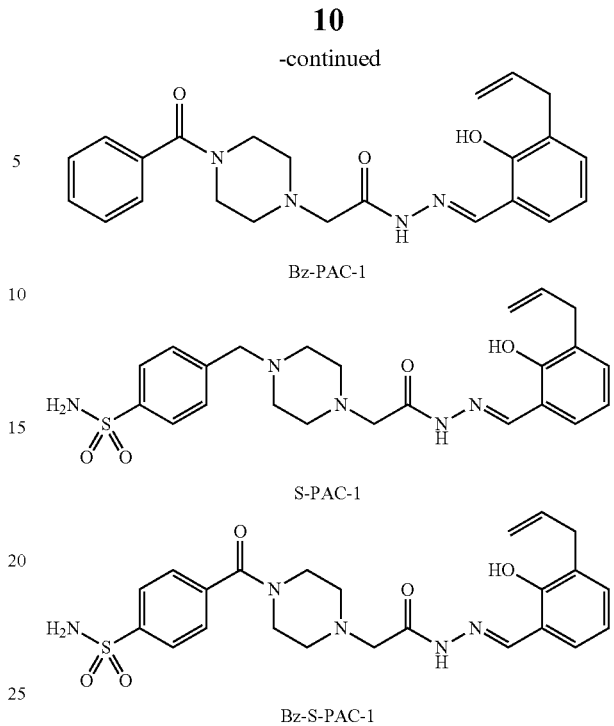

Bz-PAC-1

S-PAC-1

Bz-S-PAC-1

PAC-1 can be safely administered to mice and research dogs at doses that give serum concentrations of ~10 µM for 48 hours. A sulfonamide-containing derivative of PAC-1, called S-PAC-1 (Scheme A), can be safely administered at doses that provide very high serum concentrations in mice (~3.5 mM). Encouragingly, a veterinary clinical trial of S-PAC-1 (administered as a 24- or 72-hour continuous IV infusion) in pet dogs with spontaneously-occurring lymphoma revealed this compound to be safe in all veterinary patients and effective at reducing or stabilizing tumor growth in 4 out of 6 patients. This result provides proof-of-concept for the notion that procaspase-3 activation via small molecule chelation of labile zinc can be a safe and effective anticancer strategy. In the continued search for more potent derivatives of PAC-1, we report herein the synthesis of new PAC-1 analogues, the evaluation of these compounds for their ability to induce death of cancer cells in culture, and further characterization various compounds with heightened metabolic stability.

Design and Synthesis of Combinatorial Library Based on PAC-1.

A library of PAC-1 analogues was designed with the goal of identifying compounds capable of eliciting potent death of cancer cells in culture. As the maximal cytotoxicity of S-PAC-1 is not reached until at least 24 hours, and both PAC-1 and S-PAC-1 exhibit short half-lives of 1-2 hours in vivo, a secondary goal of this study was to identify PAC-1 analogues that could induce apoptosis more rapidly. Reported synthetic routes to PAC-1 and S-PAC-1, as well as other PAC-1 analogues, utilize the condensation of a hydrazide and an aldehyde as the final step in the synthetic scheme (U.S. Patent Publication No. 2007/0049602) (WO 2008/134474 (Hergenrother et al.)). This modular nature of the PAC-1 synthesis allows for a diverse array of functional groups to be conveniently incorporated into the PAC-1 scaffold without altering the core ortho-hydroxy N-acyl hydrazone motif essential for procaspase-3 activation and induction of apoptosis.

Figure 2:
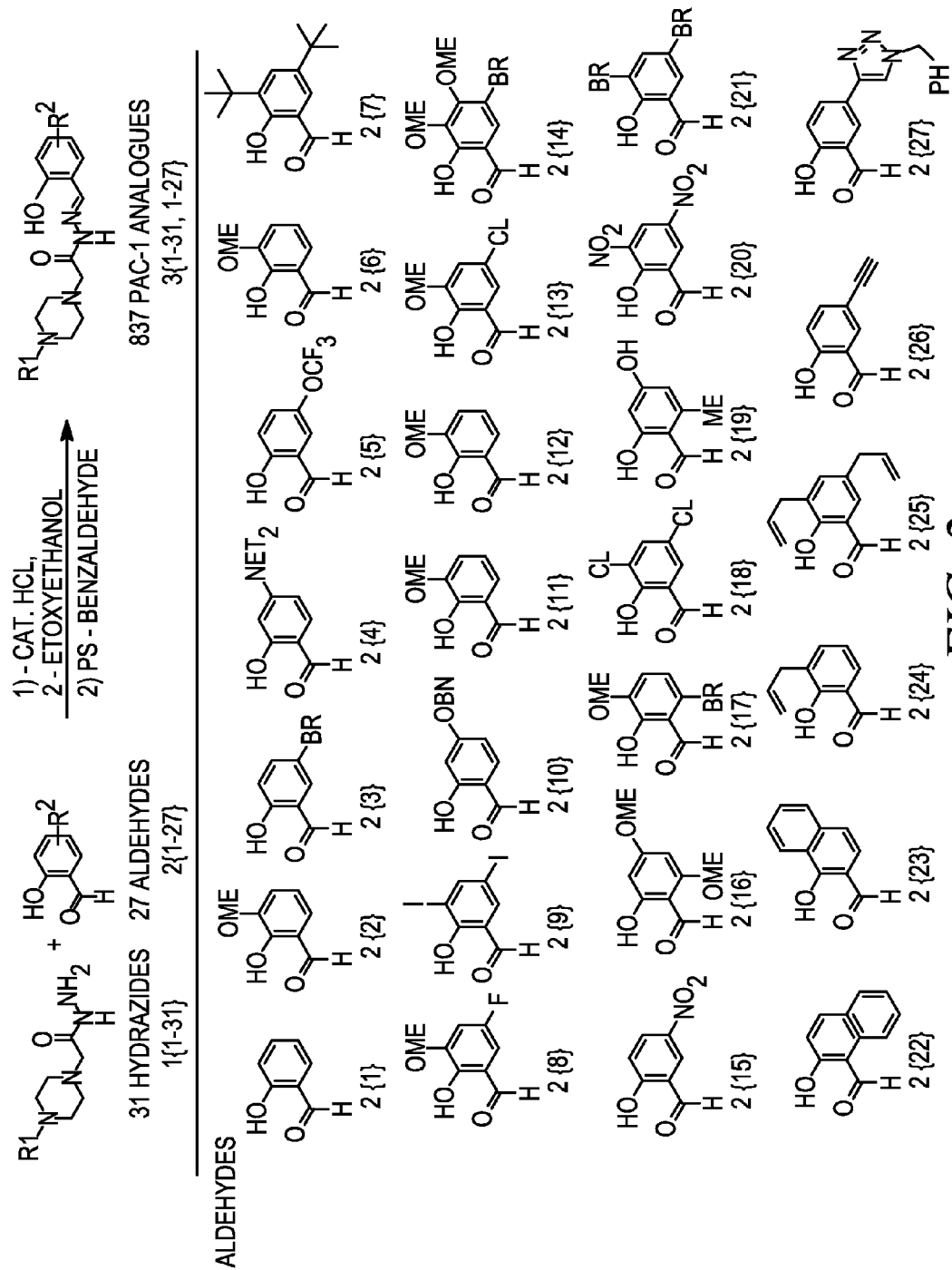
FIG. 2. Aldehydes used to a combinatorial library of PAC-1 analogues, according to certain embodiments.

As shown in FIGS. 1 and 2, 31 hydrazides (1{1-31}) and 27 aldehydes (2{1-27}) were selected for building the library of 837 PAC-1 analogues. The hydrazides were constructed from commercially available benzyl halide starting materials. The syntheses of hydrazides 1{1-6} have been reported previously (Putt et al., *Nat Chem Biol* 2006, 2, 543-550; Peterson et al., *J Med Chem* 2009, 52, 5721-5731; Peterson et al., *Cancer Res* 2010, 70, 7232-41). Hydrazides 1{7-27} were synthesized according to Scheme 1. Substituted benzyl halides 4 {7-27} first reacted with piperazine to form substituted benzylpiperazines 5{7-27}. A second alkylation of the piperazine ring with ethyl chloroacetate gave disubstituted piperazines 6 {7-27}, and the esters were then converted to hydrazides 1{7-27} by reaction with hydrazine.

Scheme 1: Synthesis of hydrazides 1{7-27}.

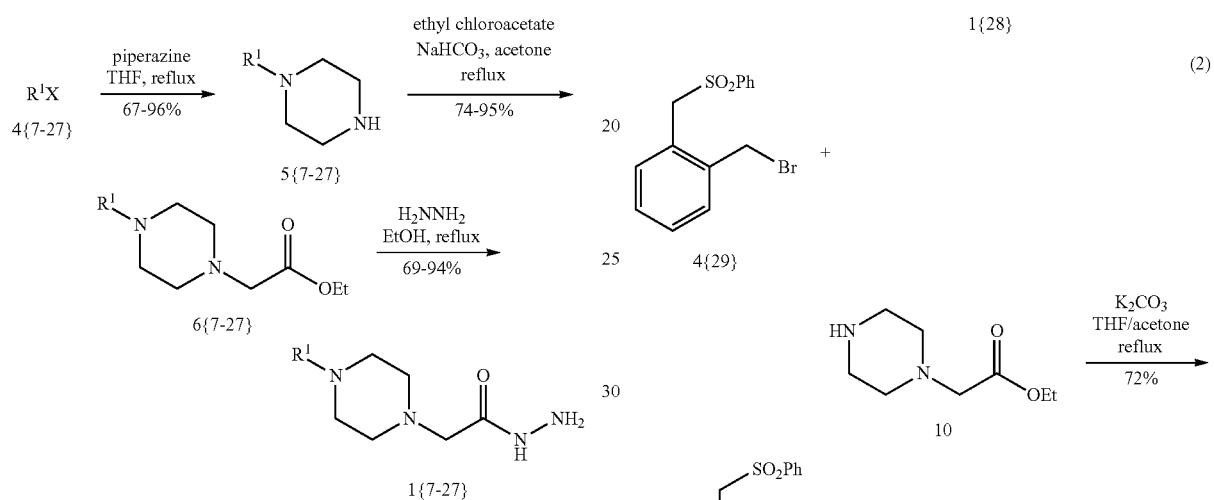

The synthetic routes toward hydrazides 1{28-31} are detailed in Scheme 2. Synthesis of hydrazide 1{28} began by the alkylation of piperazine with 4-vinylbenzyl chloride (7) to form monosubstituted piperazine 8 (Scheme 2, equation 1). A second alkylation with ethyl chloroacetate formed ester 9, and reaction with hydrazine formed the hydrazide and reduced the olefin, giving hydrazide 1{28}. The reduction of olefins with hydrazine typically involves the addition of an oxidizing agent (Miller, C. E., Hydrogenation with Diimide. *J Chem Educ* 1965, 42, 254), but the presence of atmospheric oxygen was sufficient to achieve this transformation.

Scheme 2: Synthesis of hydrazides 1{28-31}.

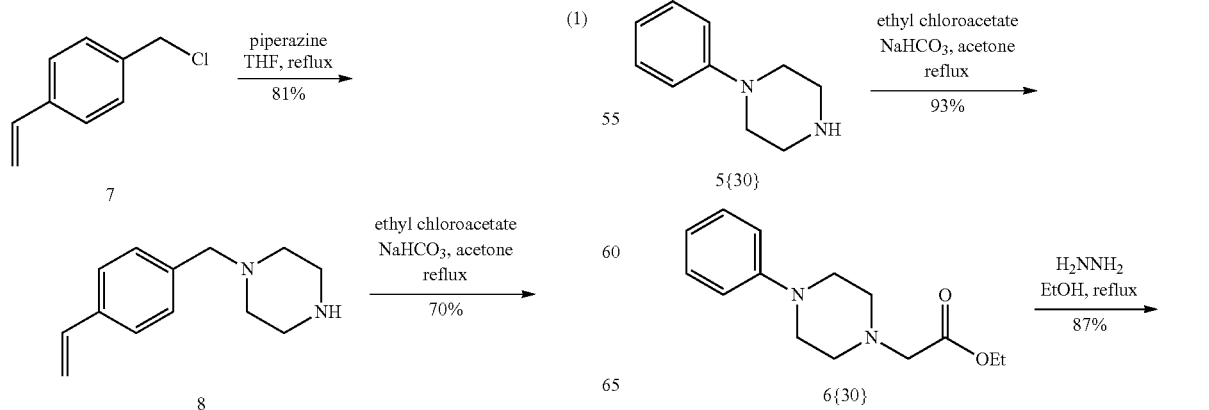

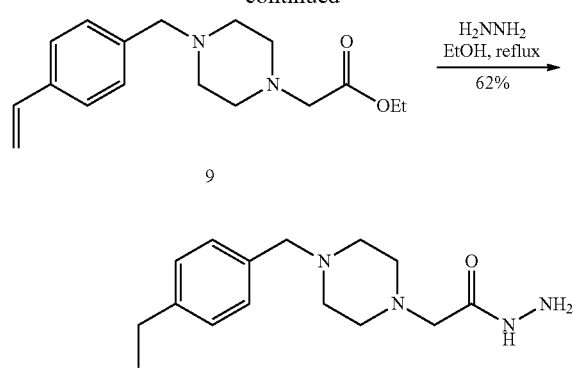

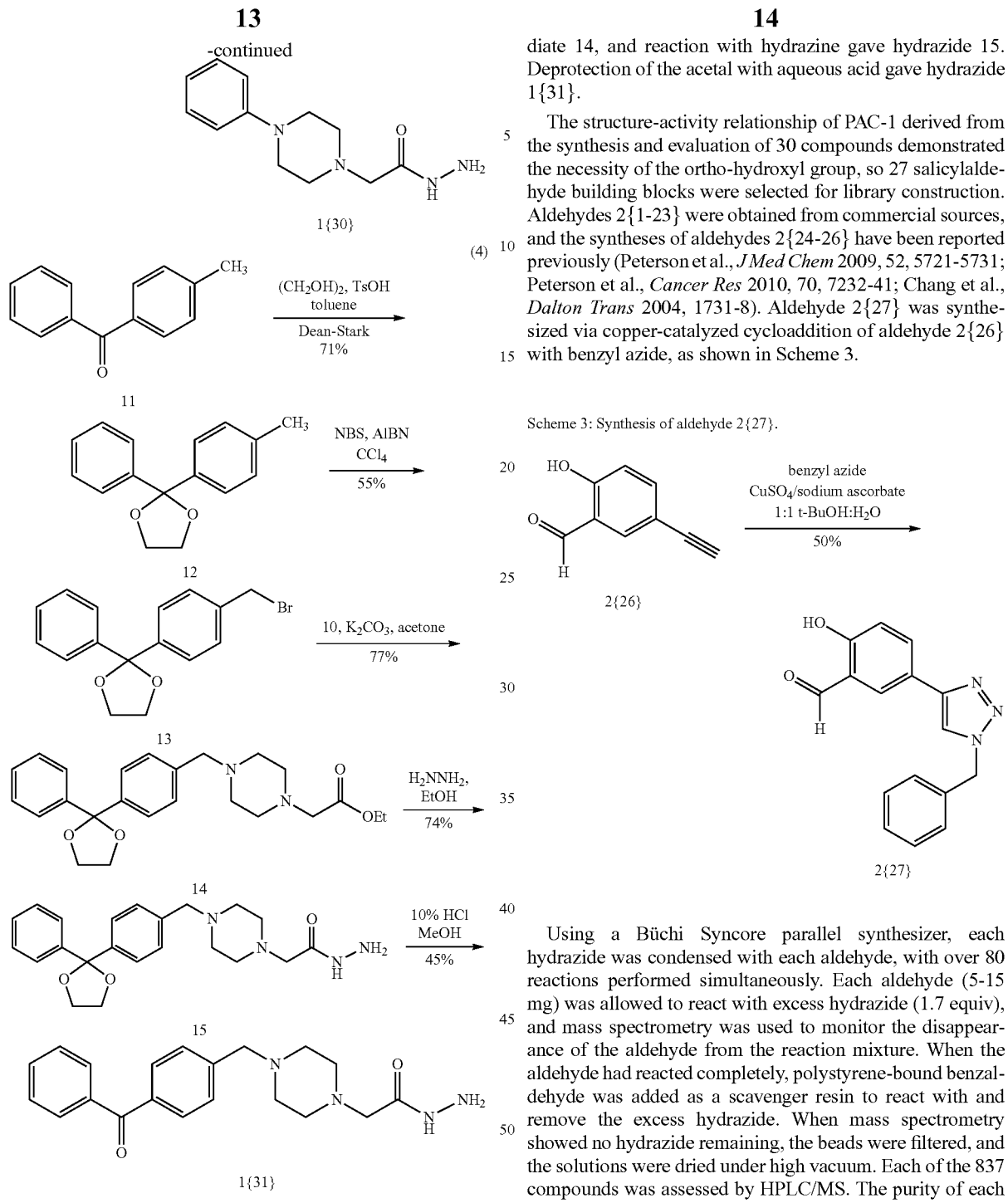

diate 14, and reaction with hydrazine gave hydrazide 15. Deprotection of the acetal with aqueous acid gave hydrazide 1{31}.

The structure-activity relationship of PAC-1 derived from the synthesis and evaluation of 30 compounds demonstrated the necessity of the ortho-hydroxyl group, so 27 salicylaldehyde building blocks were selected for library construction. Aldehydes 2{1-23} were obtained from commercial sources, and the syntheses of aldehydes 2{24-26} have been reported previously (Peterson et al., *J Med Chem* 2009, 52, 5721-5731; Peterson et al., *Cancer Res* 2010, 70, 7232-41; Chang et al., *Dalton Trans* 2004, 1731-8). Aldehyde 2{27} was synthesized via copper-catalyzed cycloaddition of aldehyde 2{26} with benzyl azide, as shown in Scheme 3.

Scheme 3: Synthesis of aldehyde 2{27}.

Using a Büchi Syncore parallel synthesizer, each hydrazide was condensed with each aldehyde, with over 80 reactions performed simultaneously. Each aldehyde (5-15 mg) was allowed to react with excess hydrazide (1.7 equiv), and mass spectrometry was used to monitor the disappearance of the aldehyde from the reaction mixture. When the aldehyde had reacted completely, polystyrene-bound benzaldehyde was added as a scavenger resin to react with and remove the excess hydrazide. When mass spectrometry showed no hydrazide remaining, the beads were filtered, and the solutions were dried under high vacuum. Each of the 837 compounds was assessed by HPLC/MS. The purity of each compound was about 74-100%, with an average purity of 91%.

Synthesis of hydrazide 1{29} (Scheme 2, equation 2) began with the reaction of ethyl 2-(piperazin-1-yl)acetate (10) with benzyl bromide 4 {29} to form intermediate 6 {29}. Reaction of 6 {29} with hydrazine then formed hydrazide 1{29}. Hydrazide 1 {30} (Scheme 2, equation 3) was synthesized beginning with the reaction of 1-phenylpiperazine (5{30}) with ethyl chloroacetate to give disubstituted piperazine 6{30}, and reaction with hydrazine formed hydrazide 1{30}. Hydrazide 1{31}, was synthesized by first protecting 4-methylbenzophenone (11) as the ethylene acetal (12), as shown in Scheme 2, equation 4. This compound was brominated under radical conditions to give benzyl bromide 13. Reaction with monosubstituted piperazine 10 gave interme- Evaluation of the PAC-1 Combinatorial Library.

With 837 PAC-1 analogues in hand, compounds were evaluated for their ability to induce apoptosis in cell culture. U-937 human lymphoma cells were exposed to the compounds for 24 hours at a concentration of 20 μM. Both PAC-1 and S-PAC-1 display moderate potency (~50% cell death) versus this cell line under these conditions. Apoptotic cell death was assessed by flow cytometry, using Annexin V-FITC/propidium iodide staining. Through this screening process, six compounds were identified and confirmed to induce >80% cell death under these conditions.

TABLE A
Six library compounds induce potent cell death of U-937 cells (human lymphoma) in both 24 and 72 hour experiments, with biomass quantified using the sulforhodamine B assay.
| | 72-hour IC$_{50}$ (μM) | % Cytotoxicity (24 hours at 7.5 μM) | Procaspase-3 (% Activity at 3.5 μM) |
|---|---|---|---|
| 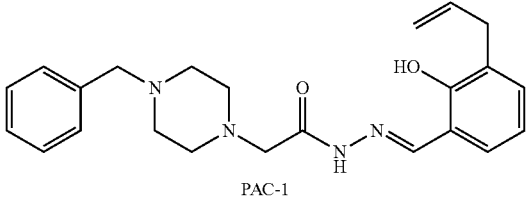 PAC-1 | 3.8 ± 0.4 | 21 | 42 ± 1.8 |
| 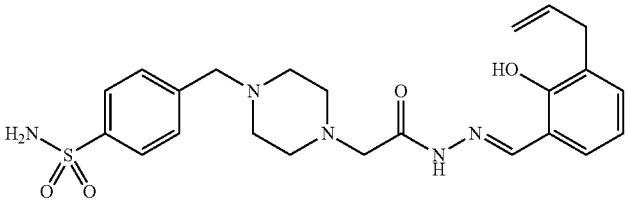 [SMILES: C=CCc1cccc(/C=N/NC(=O)CN2CCN(Cc3ccc(S(N)(=O)=O)cc3)CC2)c1O] S-PAC-1 | 4.4 ± 0.7 | 23 | 4 ± 0.6 |
| 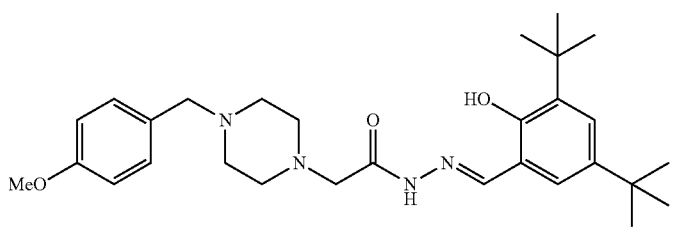 [SMILES: COc1ccc(CN2CCN(CC(=O)N/N=C/c3cc(C(C)(C)C)cc(C(C)(C)C)c3O)CC2)cc1] 3{2,7} | 1.8 ± 0.2 | 90 | 53 ± 4.1 |
| 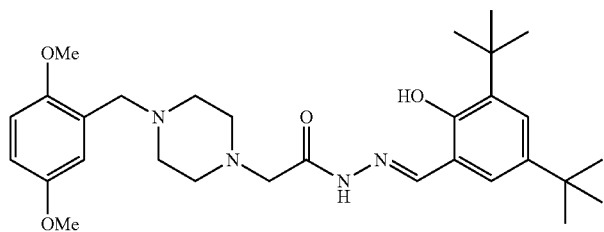 [SMILES: COc1ccc(OC)c(CN2CCN(CC(=O)N/N=C/c3cc(C(C)(C)C)cc(C(C)(C)C)c3O)CC2)c1] 3{4,7} | 1.6 ± 0.2 | 53 | 64 ± 2.5 |
| 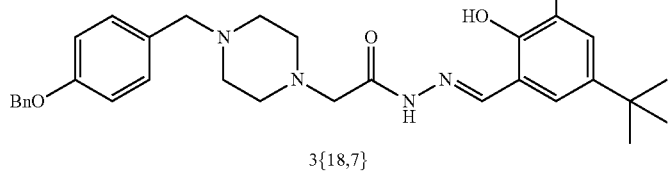 3{18,7} | 1.4 ± 0.2 | 97 | 36 ± 1.6 |
| 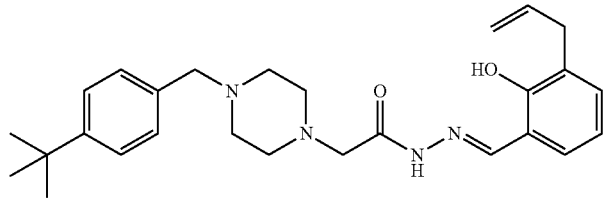 [SMILES: C=CCc1cccc(/C=N/NC(=O)CN2CCN(Cc3ccc(C(C)(C)C)cc3)CC2)c1O] 3{20,24} | 0.9 ± 0.03 | 83 | 82 ± 2.4 |

TABLE A-continued

Six library compounds induce potent cell death of U-937 cells (human lymphoma) in both 24 and 72 hour experiments, with biomass quantified using the sulforhodamine B assay.

| | 72-hour IC$_{50}$ (µM) | % Cytotoxicity (24 hours at 7.5 µM) | Procaspase-3 (% Activity at 3.5 µM) |
|---|---|---|---|
| 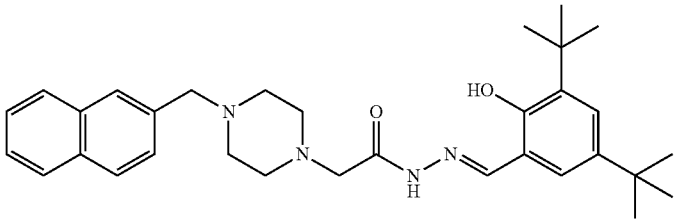 [SMILES: CC(C)(C)c1cc(/C=N/NC(=O)CN2CCN(Cc3ccc4ccccc4c3)CC2)c(O)c(C(C)(C)C)c1] 3{25,7} | 1.0 ± 0.04 | 50 | 69 ± 5.3 |
| 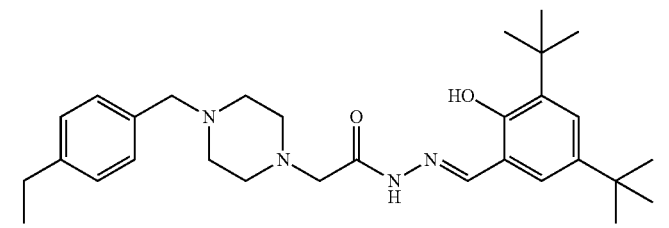 [SMILES: CCc1ccc(CN2CCN(CC(=O)N/N=C/c3cc(C(C)(C)C)cc(C(C)(C)C)c3O)CC2)cc1] 3{28,7} | 2.0 ± 0.2 | 70 | 60 ± 2.4 |

Cell Death Induction and Relief of Zinc-Mediated Inhibition of Procaspase-3 by Hit Compounds.

After re-synthesis of the hits (3 {2,7}, 3 {4,7}, 3{18,7}, 3 {20,24}, 3 {25,7}, and 3{28,7}), analytically pure samples of the compounds were evaluated in further biological assays. These structures and the biological results are shown in Table A, above. The compounds were evaluated, at a range of concentrations, for their ability to induce cell death in U-937 cells, as well as their ability to activate procaspase-3 in vitro. All six of these hits were found to be 2-4 fold more potent in cell culture than PAC-1 and S-PAC-1 in a 72-hour treatment.

In a second experiment, flow cytometry analysis with Annexin V-FITC/propidium iodide was performed on U-937 cells that were exposed to the compounds at a single concentration (7.5 µM) for 24 hours (Table A). Within 24 hours the majority of the compound treated cells were undergoing apoptosis (cells in the lower right quadrant of the histogram—Annexin V positive, propidium iodide negative), or were in a late apoptotic/necrotic stage (upper right quadrant—Annexin V positive, propidium iodide positive). The novel analogues were found to be more potent than PAC-1 under these 24 hour conditions.

The six confirmed hits were then evaluated in vitro for their ability to relieve zinc-mediated inhibition of procaspase-3 (Table A). In this experiment, procaspase-3 was incubated with ZnSO$_4$, conditions in which procaspase-3 has no enzymatic activity. All compounds were able to enhance procaspase-3 enzymatic activity under these conditions (as assessed by the cleavage of the colorimetric caspase-3 substrate Ac-DEVD-pNA, synthesized as previously reported (Peterson et al., Nat Protoc 2010, 5, 294-302)), and five of the six hit compounds showed greater activity than PAC-1 in this assay. These data indicate that the compounds enhance the activity of procaspase-3 in vitro through chelation of inhibitory zinc, and suggest that in the cell the compounds chelate zinc from the labile pool, allowing procaspase-3 to be processed to active caspase-3, leading to apoptotic cell death.

The direct modulation of apoptotic proteins is a practical anticancer strategy. PAC-1 and its derivative S-PAC-1, which chelate labile cellular zinc and induce apoptosis in cancer cells, have been effective in various preclinical anti-tumor models. However, derivatives that induce cell death more rapidly and more potently would be even more attractive as therapeutics. Using parallel synthesis and guided by the known SAR, we constructed 837 PAC-1 analogues and evaluated them for their cell death inducing properties. The six compounds shown in Table A emerged from this effort. These compounds are two- to four-fold more potent than PAC-1 at induction of cancer cell death in both 24-hour and 72-hour assays.

Given the general hydrophobicity of the hit compounds relative to PAC-1, the enhanced potency and enhanced rate of cell death may be driven by enhanced cell permeability. These qualities are likely to be advantageous as the compounds are moved forward in vivo. In addition, other members of this library will likely emerge as viable in vivo candidates as alternate properties (such as propensity to cross the blood-brain barrier, improved metabolic stability, improved solubility/formulation for in vivo studies, etc.) are examined. Thus, this library of 837 compounds will be a rich source from which to develop next-generation procaspase-3 activating compounds.

Additional Compounds and Analysis.

A high-throughput screen of approximately 20,000 compounds identified PAC-1 (1, Scheme A1) as a compound that enhanced the cleavage of procaspase-3 in vitro. The compound induces apoptotic cell death in a wide array of cancer cell lines in culture and shows anticancer efficacy in multiple murine tumor models.[1] Further study of the structure-activity relationships (SAR) identified the ortho-hydroxy-N-acylhydrazone as the key pharmacophore.[2-3] Several PAC-1 derivatives containing this motif have comparable activity in vitro and in cell culture, but derivatives with a modified core lose activity.[3] The ortho-hydroxy-N-acylhydrazone is known to chelate metals,[4] many of which are also known to inhibit procaspase and caspase enzymes.[2, 5-7] In particular, zinc from the labile zinc pool, which is bound loosely and does not play an essential role in the activity of these proteins, has been shown to colocalize with procaspase-3 and inhibit its enzymatic activity. The mechanism of action of PAC-1 likely involves the chelation of zinc from the labile pool, relieving the zinc-mediated inhibition of procaspase-3 and allowing the enzyme to process itself to the active form.[2-3]

Scheme A1. Structures of PAC-1 (1) and S-PAC-1 (2).

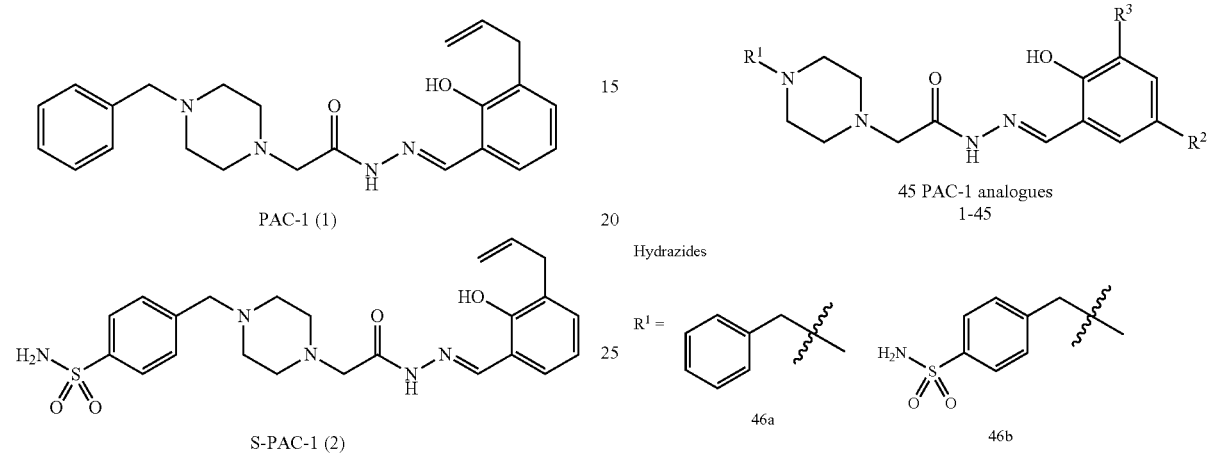

Pharmacokinetic studies with PAC-1 revealed that serum concentrations of approximately 10 µM can be achieved with minimal side effects.[8] A sulfonamide-containing derivative of PAC-1, called S-PAC-1 (2, Scheme A1), can be safely administered at doses of 350 mg/kg or higher, giving a peak plasma concentration of 3.5 mM.[9] The improved safety profile is due in large part to its decreased ability to cross the blood-brain barrier (BBB), as compared to PAC-1.[10] Encouragingly, S-PAC-1 was effective in reducing or stabilizing tumor growth in four out of six canine patients with spontaneously occurring lymphoma, and the compound was well tolerated in all six dogs.[9] This result demonstrates the potential for procaspase activation as a safe and effective anticancer strategy.

Results and Discussion.

Compound Synthesis.

Previous syntheses of PAC-1 and other derivatives involved the late-stage condensation of a hydrazide and an aldehyde to form the key ortho-hydroxy-N-acylhydrazone.[1, 3, 9, 11] This reaction has been useful for the generation of large numbers of derivatives from a comparatively small number of starting materials.[11] In this work, PAC-1 analogues 1-45 were synthesized by the condensation of nine hydrazides (46a-i) with five aldehydes (47a-e), as shown in Scheme A2.

Scheme A2. Building blocks used to construct library.

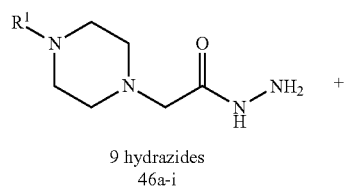

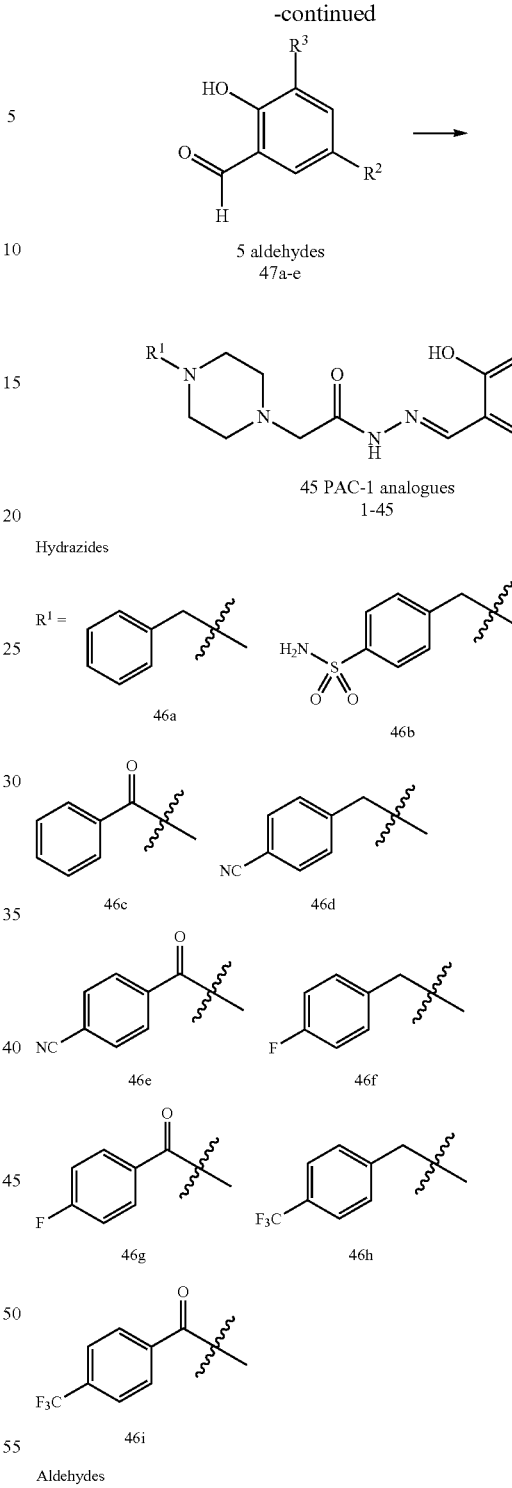

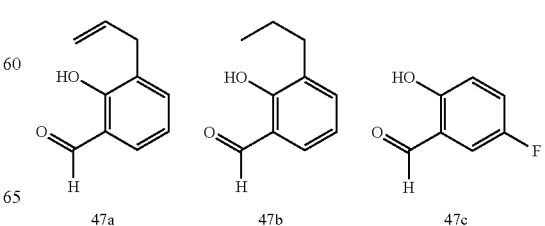

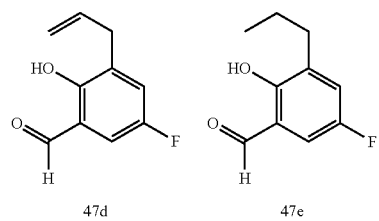

The hydrazides were synthesized according to Scheme A3a-c. The synthesis began with the alkylation of piperazine (48) with ethyl chloroacetate (49) to form monosubstituted piperazine 50. Compound 50 was then reacted with a substituted benzyl or benzoyl halide to give disubstituted piperazines 51a-i in high yields. Reaction of the esters with hydrazine then gave hydrazides 46a-i.

Scheme A3. Synthesis of PAC-1 analogues. (a) Synthesis of hydrazides (46a-i). (b) Synthesis of aldehydes (47a-e). (c) Condensation of hydrazides and aldehydes to form PAC-1 analogues (1-45).

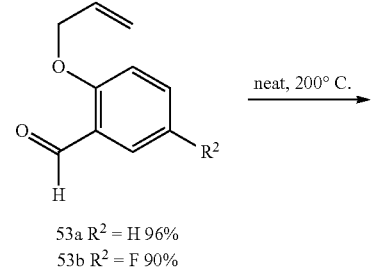
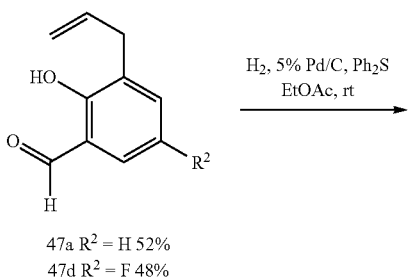
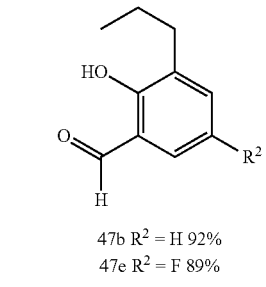
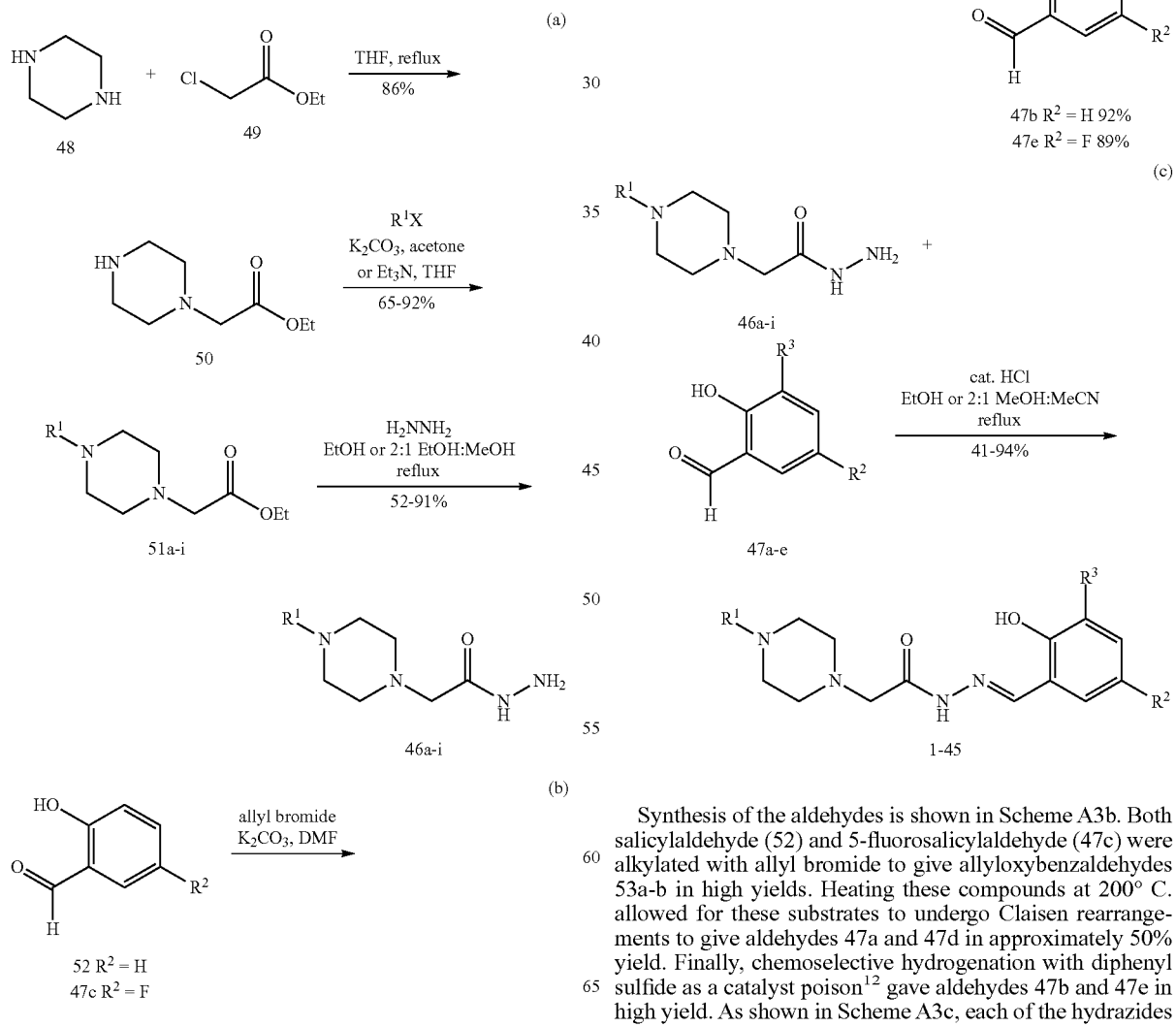

Figure 3:
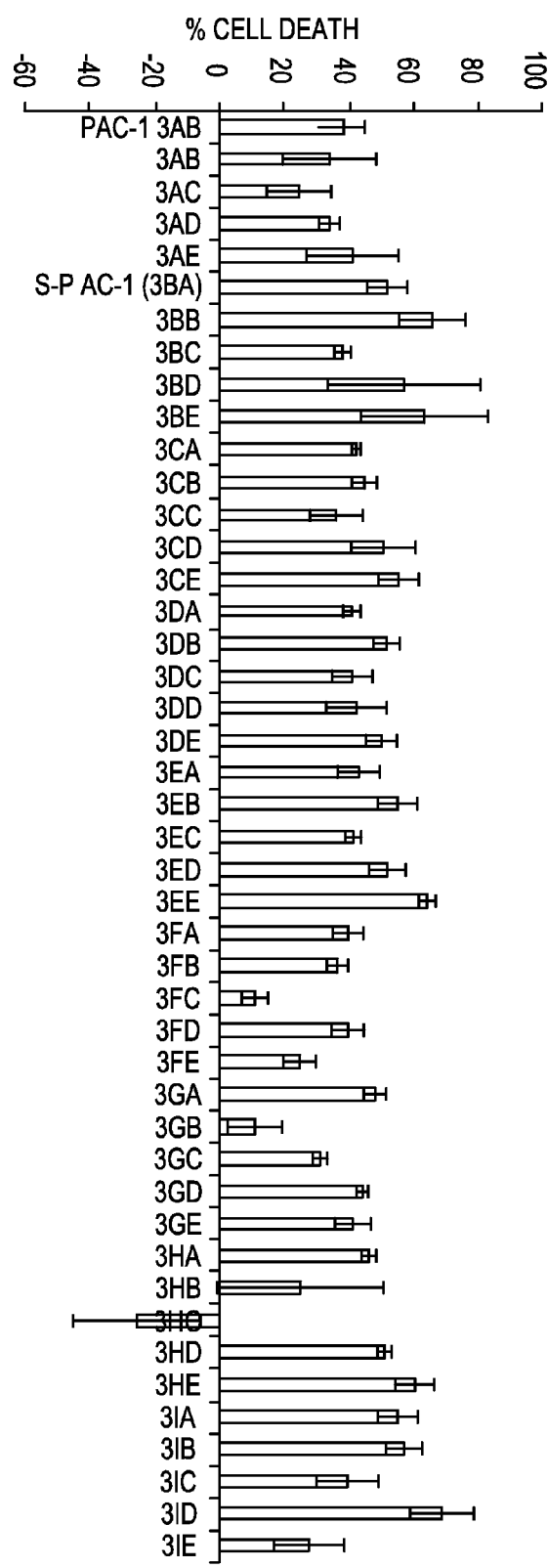
FIG. 3. Cell culture activity. U-937 cells (human lymphoma) treated with compounds at 25 µM for 24 hours. Cell viability assessed by Alamar blue assay. Error bars represent standard error from the mean (n=3).
Figure 4A:
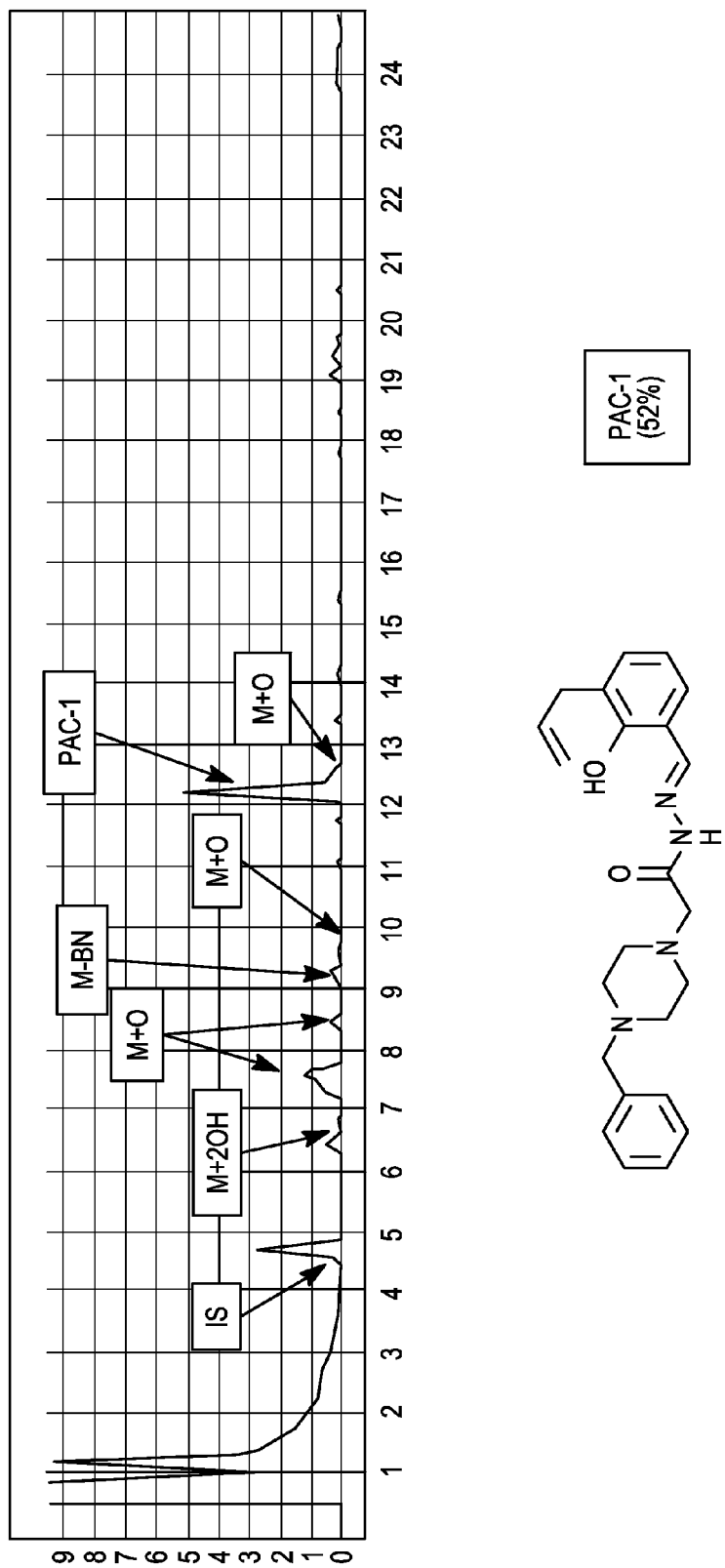
FIG. 4. Liver Microsome Stability Assay. Compounds (10 µM) incubated with liver microsomes for 3 h and quenched with MeCN containing internal standard, analyzed by LC/MS (280 nm).
Figure 4B:
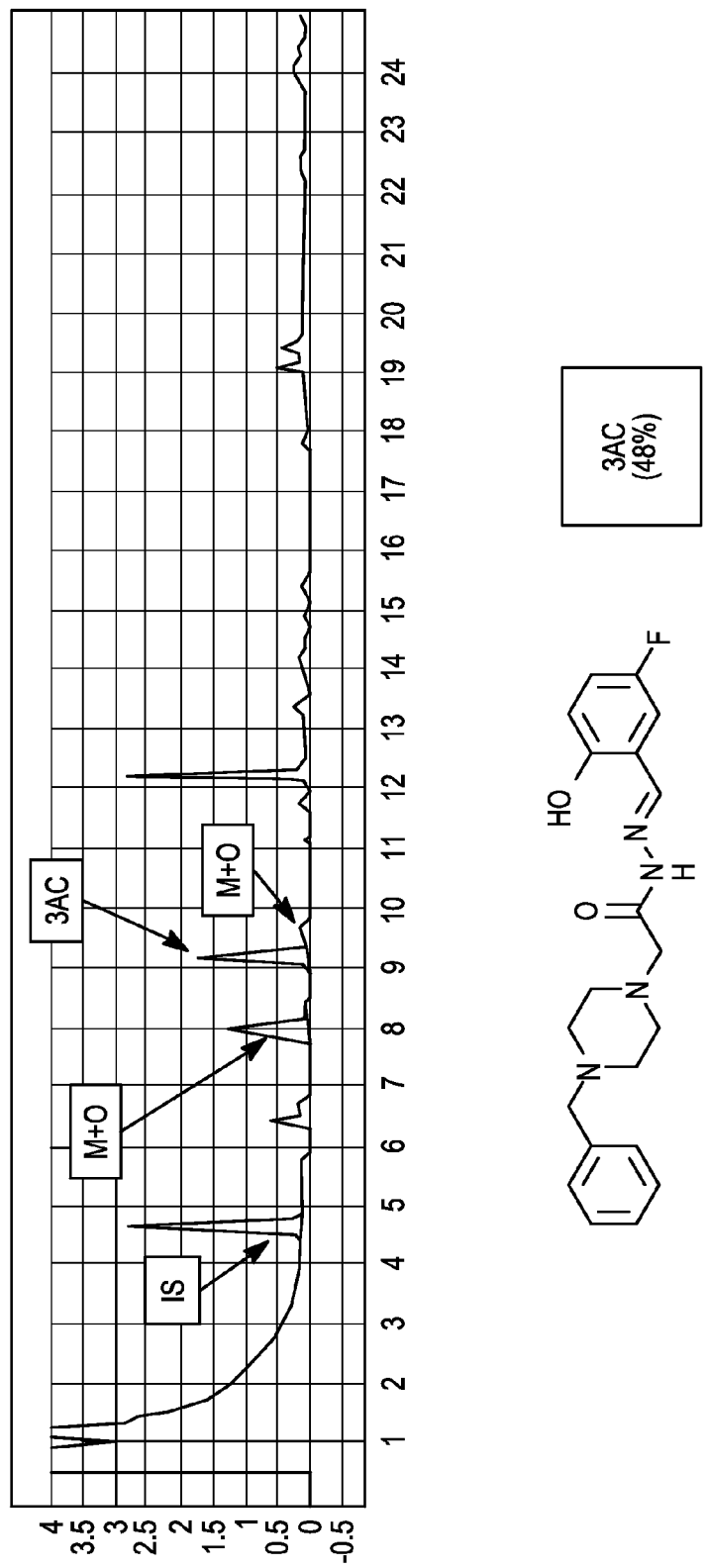
Figure 4C:
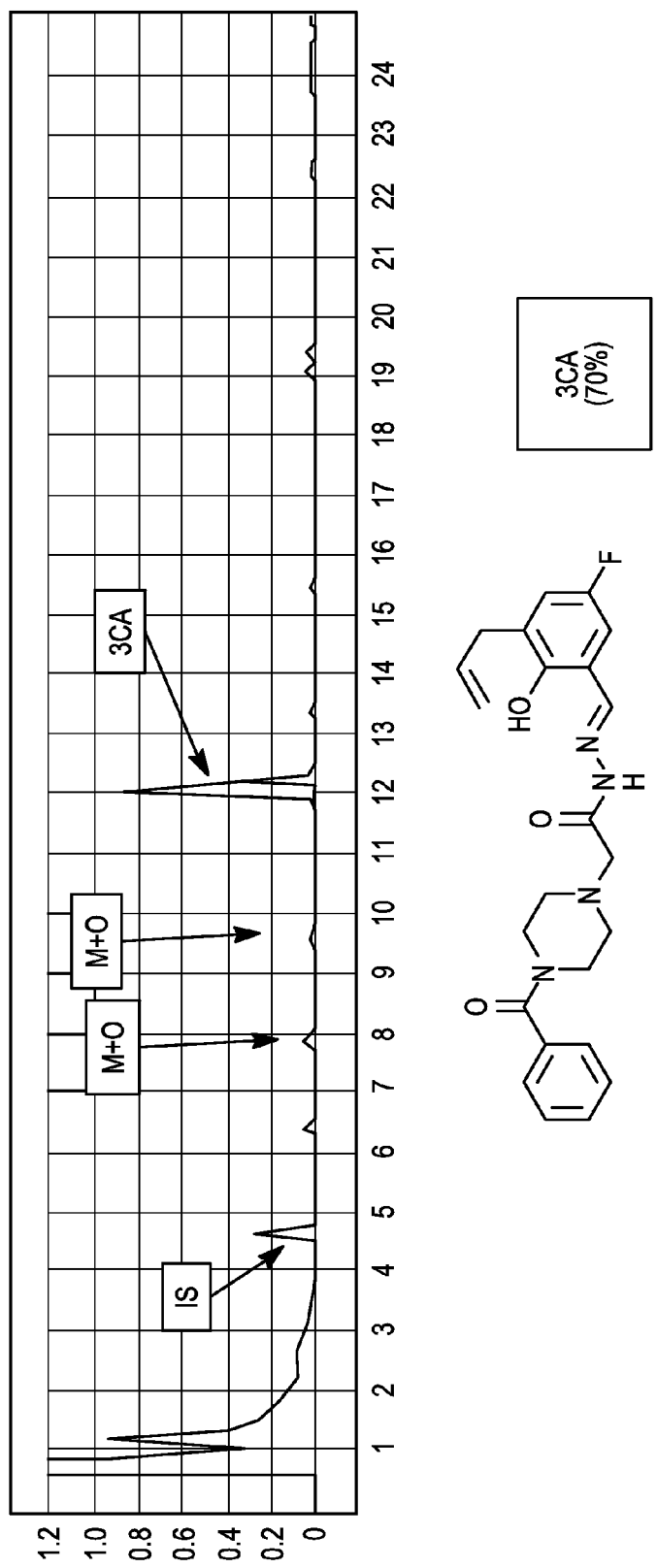
Figure 4D:
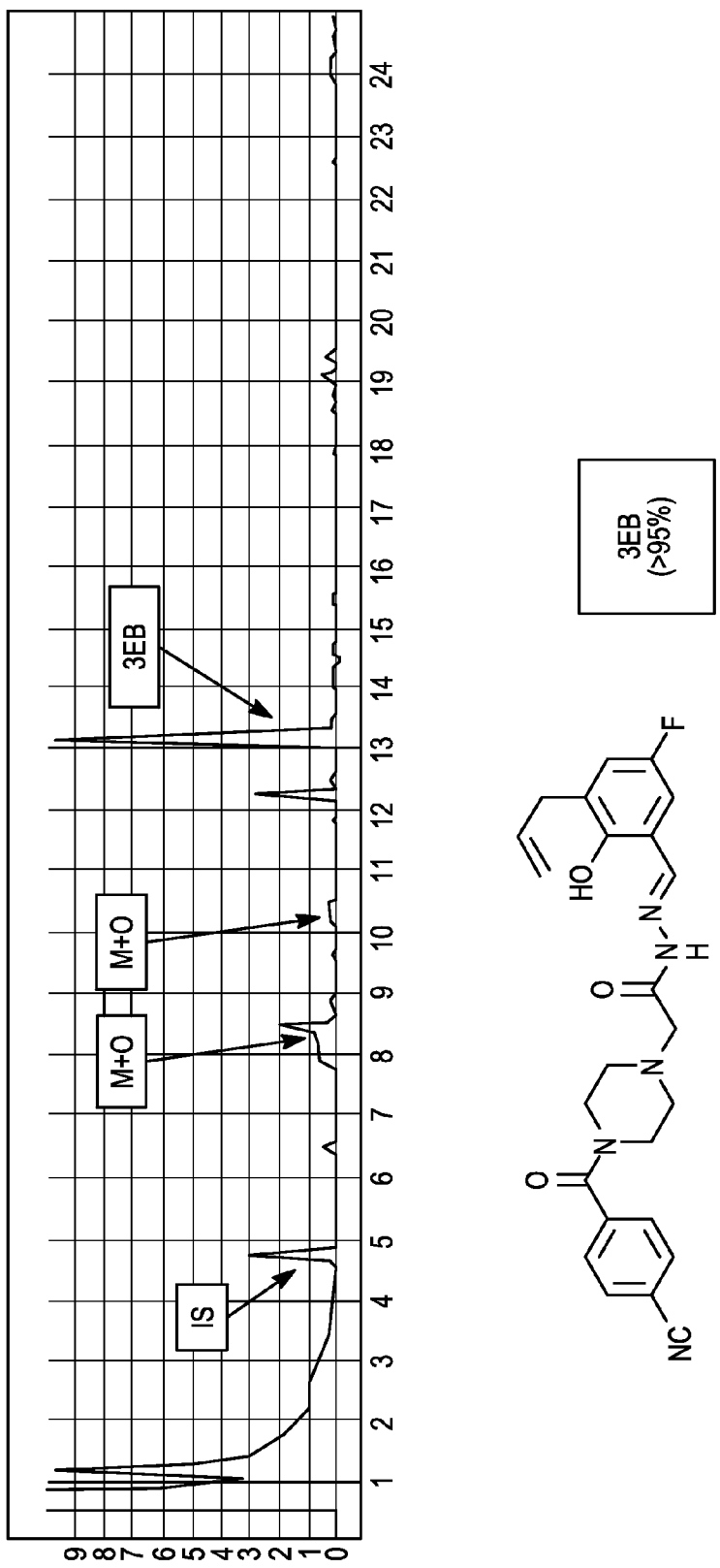
Figure 4E:
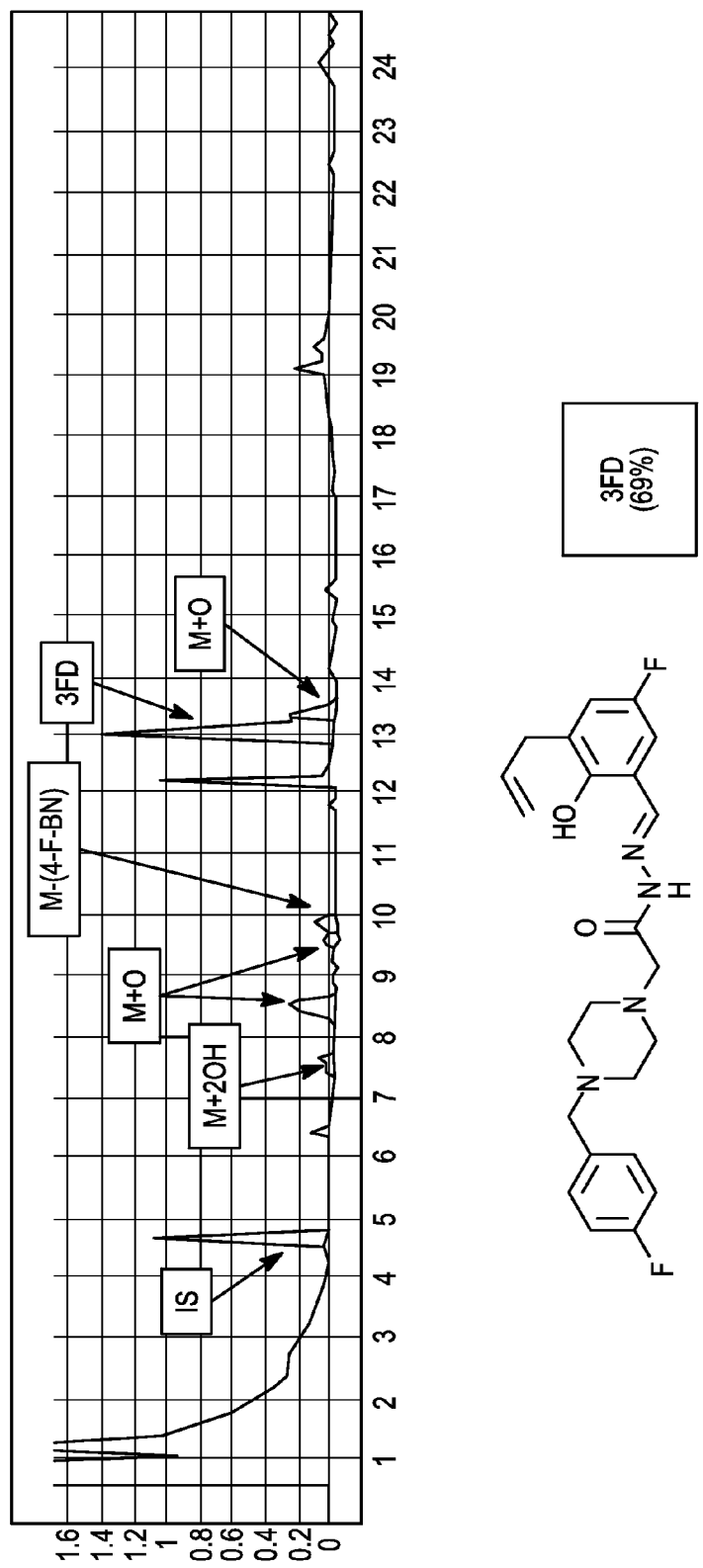
Figure 4F:
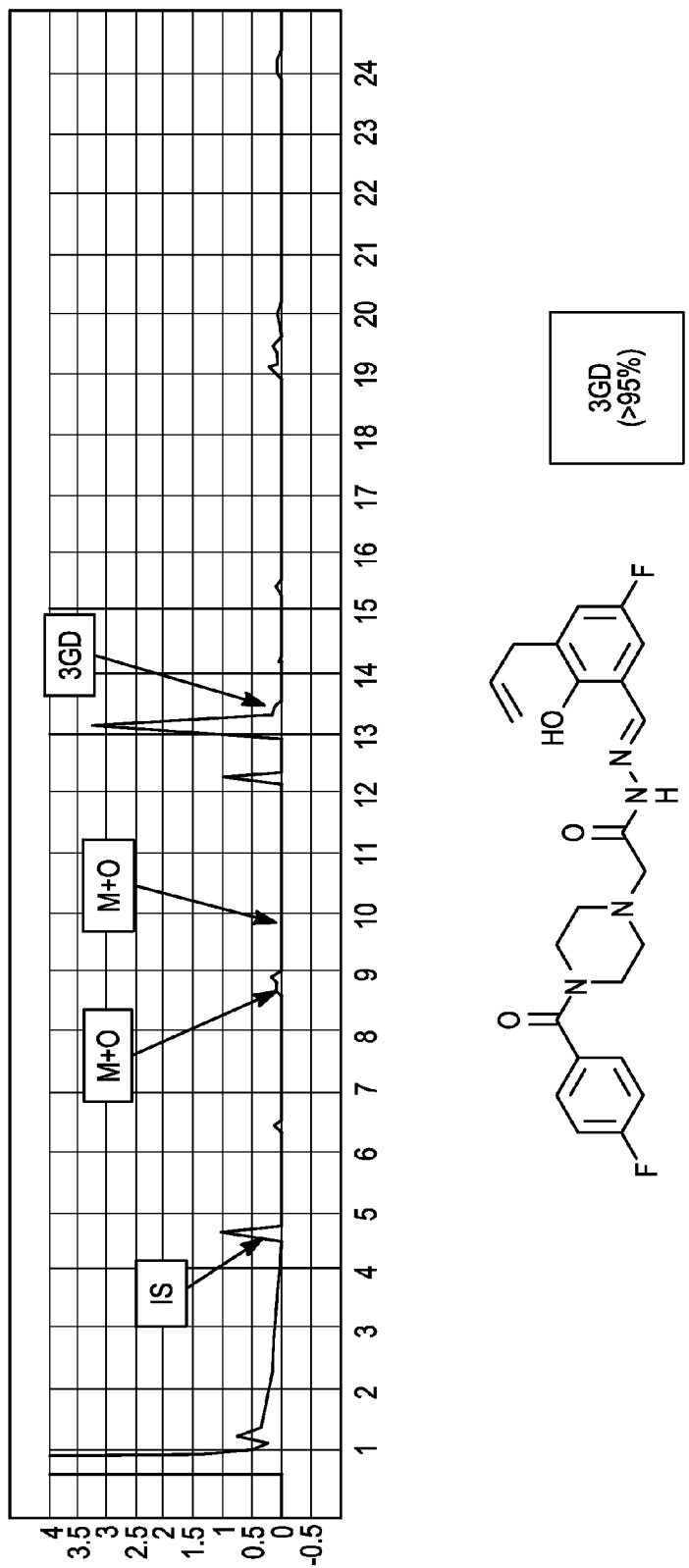
Figure 4G:
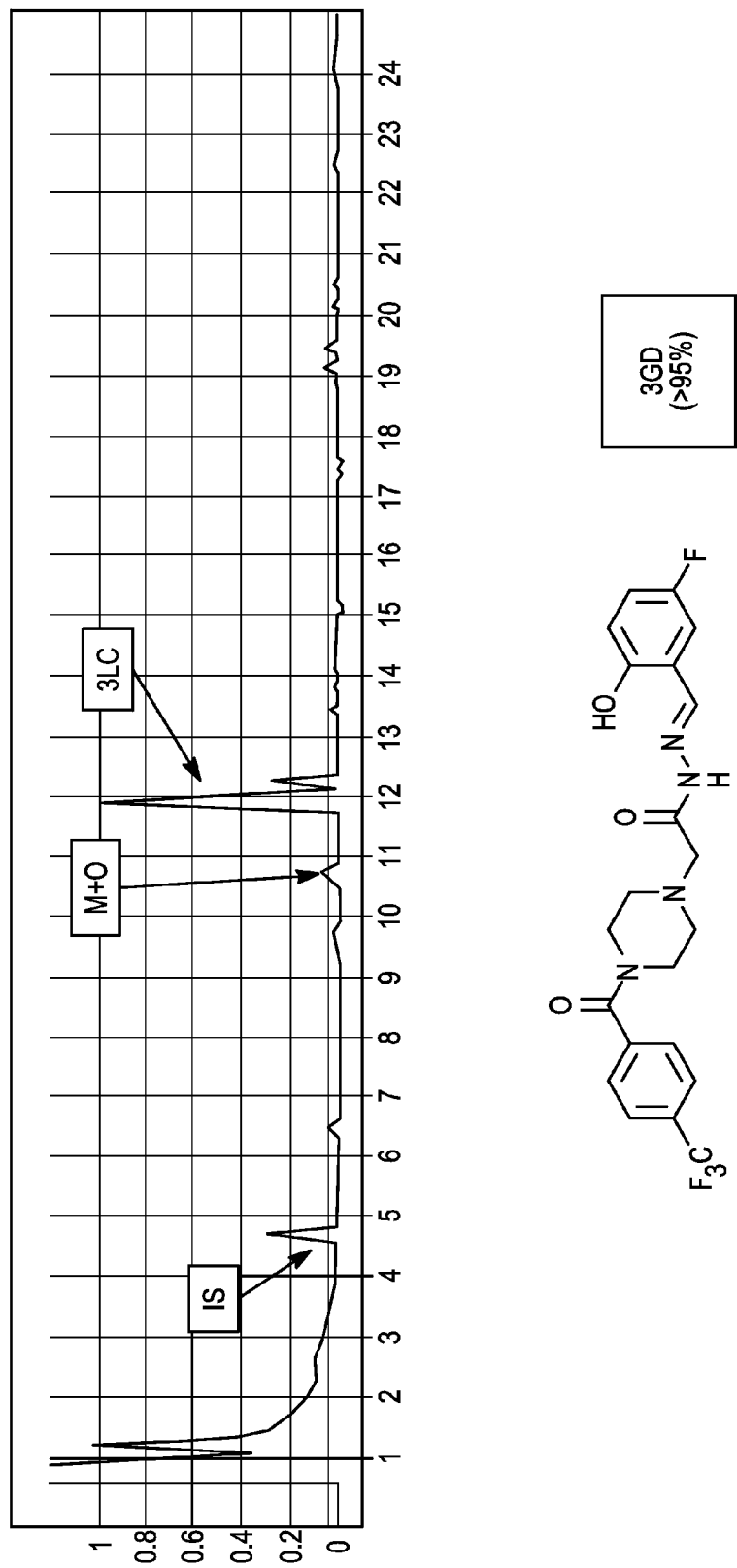

Synthesis of the aldehydes is shown in Scheme A3b. Both salicylaldehyde (52) and 5-fluorosalicylaldehyde (47c) were alkylated with allyl bromide to give allyloxybenzaldehydes 53a-b in high yields. Heating these compounds at 200° C. allowed for these substrates to undergo Claisen rearrangements to give aldehydes 47a and 47d in approximately 50% yield. Finally, chemoselective hydrogenation with diphenyl sulfide as a catalyst poison[12] gave aldehydes 47b and 47e in high yield. As shown in Scheme A3c, each of the hydrazides (46a-i) was condensed with each of the aldehydes (47a-e) in the presence of catalytic HCl to give PAC-1 derivatives 1-45, the structures of which are given in Table 1 (see also FIGS. 3 and 4).

LC/MS. The results of this assay are shown in Table 1. Compounds that contained benzoyl substituents were significantly more stable than analogous compounds containing benzyl

TABLE 1

Structures, experimental data, and predicted logBB values of PAC-1 analogues.

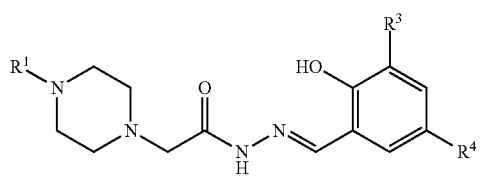

1-45

| compound | R$^1$ | R$^2$ | R$^3$ | U-937 72 h IC$_{50}$ (μM) | RLM 3 h % Stability | Predicted logBB | Mouse Toxicity |
|---|---|---|---|---|---|---|---|
| 1 (PAC-1) | Bn | H | All | 10.2 ± 0.3 | 38 ± 2 | −0.36 | 3 |
| 2 (S-PAC-1) | 4-SO$_2$NH$_2$—Bn | H | All | 8.9 ± 0.6 | 84 ± 0 | −1.45 | 0 |
| 3 | Bz | H | All | 12.1 ± 1.3 | 89 ± 4 | −0.72 | 3 |
| 4 | 4-CN—Bn | H | All | 13.7 ± 0.9 | 48 ± 2 | −0.73 | 1 |
| 5 | 4-CN—Bz | H | All | 13.1 ± 3.7 | 90 ± 4 | −1.09 | death >72 h |
| 6 | 4-F—Bn | H | All | 11.1 ± 2.1 | 31 ± 1 | −0.33 | 3 |
| 7 | 4-F—Bz | H | All | 10.2 ± 1.7 | 86 ± 2 | −0.69 | 2 |
| 8 | 4-CF$_3$—Bn | H | All | 15.3 ± 6.7 | 16 ± 1 | −0.22 | death <24 h |
| 9 | 4-CF$_3$—Bz | H | All | 6.6 ± 1.9 | 85 ± 6 | −0.57 | death <24 h* |
| 10 | Bn | H | n-Pr | 9.6 ± 2.1 | 30 ± 1 | −0.30 | 2 |
| 11 | 4-SO$_2$NH$_2$—Bn | H | n-Pr | 4.9 ± 0.4 | 61 ± 2 | −1.39 | — |
| 12 | Bz | H | n-Pr | 9.4 ± 1.3 | 71 ± 3 | −0.66 | — |
| 13 | 4-CN—Bn | H | n-Pr | 9.0 ± 1.2 | 30 ± 2 | −0.67 | — |
| 14 | 4-CN—Bz | H | n-Pr | 12.8 ± 2.7 | 61 ± 3 | −1.03 | — |
| 15 | 4-F—Bn | H | n-Pr | 10.0 ± 1.7 | 24 ± 2 | −0.27 | death <24 h |
| 16 | 4-F—Bz | H | n-Pr | 7.3 ± 0.9 | 69 ± 4 | −0.63 | — |
| 17 | 4-CF$_3$—Bn | H | n-Pr | 4.1 ± 0.4 | 15 ± 2 | −0.16 | death >72 h |
| 18 | 4-CF$_3$—Bz | H | n-Pr | 4.8 ± 1.2 | 64 ± 1 | −0.51 | death <24 h* |
| 19 | Bn | F | H | 17.0 ± 1.4 | 64 ± 4 | −0.49 | 3 |
| 20 | 4-SO$_2$NH$_2$—Bn | F | H | 19.6 ± 3.8 | 85 ± 6 | −1.57 | death >72 h |
| 21 | Bz | F | H | 15.7 ± 2.6 | 88 ± 1 | −0.84 | — |
| 22 | 4-CN—Bn | F | H | 13.5 ± 1.0 | 79 ± 4 | −0.86 | death <24 h |
| 23 | 4-CN—Bz | F | H | 15.3 ± 1.3 | 88 ± 4 | −1.21 | — |
| 24 | 4-F—Bn | F | H | 11.7 ± 1.4 | 62 ± 2 | −0.45 | 3 |
| 25 | 4-F—Bz | F | H | 15.3 ± 0.8 | 86 ± 2 | −0.81 | — |
| 26 | 4-CF$_3$—Bn | F | H | 4.7 ± 0.3 | 30 ± 5 | −0.34 | 3 |
| 27 | 4-CF$_3$—Bz | F | H | 8.7 ± 0.5 | 87 ± 3 | −0.70 | 2 |
| 28 | Bn | F | All | 9.5 ± 0.9 | 56 ± 1 | −0.33 | death <24 h |
| 29 | 4-SO$_2$NH$_2$—Bn | F | All | 9.8 ± 1.3 | 89 ± 3 | −1.42 | death >72 h |
| 30 | Bz | F | All | 8.6 ± 2.0 | 93 ± 7 | −0.69 | 2 |
| 31 | 4-CN—Bn | F | All | 12.7 ± 2.0 | 65 ± 2 | −0.70 | — |
| 32 | 4-CN—Bz | F | All | 10.1 ± 2.0 | 95 ± 4 | −1.06 | 1 |
| 33 | 4-F—Bn | F | All | 10.3 ± 4.1 | 57 ± 1 | −0.30 | — |
| 34 | 4-F—Bz | F | All | 8.5 ± 1.4 | 92 ± 3 | −0.65 | 3 |
| 35 | 4-CF$_3$—Bn | F | All | 3.4 ± 0.6 | 49 ± 3 | −0.19 | death <24 h* |
| 36 | 4-CF$_3$—Bz | F | All | 6.5 ± 0.6 | 90 ± 2 | −0.54 | 2 |
| 37 | Bn | F | n-Pr | 8.9 ± 1.2 | 49 ± 6 | −0.27 | death <24 h |
| 38 | 4-SO$_2$NH$_2$—Bn | F | n-Pr | 8.7 ± 0.4 | 62 ± 3 | −1.36 | — |
| 39 | Bz | F | n-Pr | 12.3 ± 1.0 | 86 ± 5 | −0.63 | 2 |
| 40 | 4-CN—Bn | F | n-Pr | 11.2 ± 0.9 | 49 ± 5 | −0.64 | — |
| 41 | 4-CN—Bz | F | n-Pr | 9.4 ± 1.2 | 66 ± 3 | −1.00 | 1 |
| 42 | 4-F—Bn | F | n-Pr | 7.5 ± 0.7 | 48 ± 1 | −0.24 | — |
| 43 | 4-F—Bz | F | n-Pr | 7.5 ± 1.4 | 67 ± 3 | −0.59 | 3 |
| 44 | 4-CF$_3$—Bn | F | n-Pr | 3.9 ± 0.6 | 40 ± 1 | −0.13 | death <24 h |
| 45 | 4-CF$_3$—Bz | F | n-Pr | 5.2 ± 0.6 | 64 ± 5 | −0.48 | death >72 h |

Evaluation of PAC-1 Analogues.

After the synthesis was complete, the biological activity of the compounds was evaluated. First, the 72-hour IC$_{50}$ values of the compounds against U-937 cells in culture were determined (Table 1). Encouragingly, each of the compounds was found to induce dose-dependent cell death under these conditions, and most of the compounds were approximately as potent as PAC-1 and S-PAC-1.

Next, the metabolic stability of the compounds was evaluated in rat liver microsomes. The compounds were evaluated for 3 hours at 10 μM, and the metabolites were observed by groups. Unexpectedly, the propyl-containing compounds were less stable than the allyl-containing compounds, although the dihydroxylated metabolites were not observed with the propyl compounds. In addition, S-PAC-1 was reasonably stable in the liver microsomes, despite the short in vivo half-life of the compound, suggesting that other clearance mechanisms play a greater role in elimination of S-PAC-1 from the body.

Finally, the predicted log BB value was calculated for each compound. This algorithm, which involves polar surface area and C log P, is used to predict the permeability of small molecules across the blood-brain barrier (BBB).[13] Compounds with more positive log BB values will have higher concentrations in the brain, while compounds with more negative log BB values will have higher concentrations in the blood. The values are shown in Table 1. As expected, the compounds containing more hydrophobic substituents are predicted to cross the BBB to a greater degree than those containing more polar substituents.

Assessment of Toxicity In Vivo.

With the goal of identifying a compound with improved tolerability, 32 of the 45 PAC-1 analogues were evaluated in mice. The results of the toxicity study are shown in Table 1. The level of toxicity was rated on a scale of 0 (no observable adverse effect) to 3 (severe toxicity, almost fatal). Many of the compounds were lethal to the mice, as the mice died either within 24 hours of treatment or greater than 72 hours post-treatment; these results are also noted.

Citations.

1. Putt, K. S.; Chen, G. W.; Pearson, J. M.; Sandhorst, J. S.; Hoagland, M. S.; Kwon, J. T.; Hwang, S. K.; Jin, H.; Churchwell, M. I.; Cho, M. H.; Doerge, D. R.; Helferich, W. G.; Hergenrother, P. J., Small-molecule activation of procaspase-3 to caspase-3 as a personalized anticancer strategy. *Nat. Chem. Biol.* 2006, 2, 543-550.
2. Peterson, Q. P.; Goode, D. R.; West, D. C.; Ramsey, K. N.; Lee, J. J. Y.; Hergenrother, P. J., PAC-1 Activates Procaspase-3 in Vitro through Relief of Zinc-Mediated Inhibition. *J. Mol. Biol.* 2009, 388, 144-158.
3. Peterson, Q. P.; Hsu, D. C.; Goode, D. R.; Novotny, C. J.; Totten, R. K.; Hergenrother, P. J., Procaspase-3 Activation as an Anti-Cancer Strategy: Structure-Activity Relationship of Procaspase-Activating Compound 1 (PAC-1) and Its Cellular Co-Localization with Caspase-3. *J. Med. Chem.* 2009, 52, 5721-5731.
4. Charkoudian, L. K.; Pham, D. M.; Franz, K. J., A prochelator triggered by hydrogen peroxide inhibits iron-promoted hydroxyl radical formation. *J. Am. Chem. Soc.* 2006, 128, 12424-12425.
5. Aiuchi, T.; Mihara, S.; Nakaya, M.; Masuda, Y.; Nakajo, S.; Nakaya, K, Zinc ions prevent processing of caspase-3 during apoptosis induced by geranylgeraniol in HL-60 cells. *J. Biochem.* 1998, 124, 300-303.
6. Chai, F.; Truong-Tran, A. Q.; Ho, L. H.; Zalewski, P. D., Regulation of caspase activation and apoptosis by cellular zinc fluxes and zinc deprivation: A review. *Immunol. Cell Biol.* 1999, 77, 272-278.
7. Perry, D. K.; Smyth, M. J.; Stennicke, H. R.; Salvesen, G. S.; Duriez, P.; Poirier, G. G.; Hannun, Y. A., Zinc is a potent inhibitor of the apoptotic protease, caspase-3. A novel target for zinc in the inhibition of apoptosis. *J. Biol. Chem.* 1997, 272, 18530-18533.
8. Lucas, P. W.; Schmit, J. M.; Peterson, Q. P.; West, D. C.; Hsu, D. C.; Novotny, C. J.; Dirikolu, L.; Churchwell, M. I.; Doerge, D. R.; Garrett, L. D.; Hergenrother, P. J.; Fan, T. M., Pharmacokinetics and derivation of an anticancer dosing regimen for PAC-1, a preferential small molecule activator of procaspase-3, in healthy dogs. *Invest. New Drugs* 2011, 29, 901-911.
9. Peterson, Q. P.; Hsu, D. C.; Novotny, C. J.; West, D. C.; Kim, D.; Schmit, J. M.; Dirikolu, L.; Hergenrother, P. J.; Fan, T. M., Discovery and canine preclinical assessment of a nontoxic procaspase-3-activating compound. *Cancer Res.* 2010, 70, 7232-7241.
10. West, D. C.; Qin, Y.; Peterson, Q. P.; Thomas, D. L.; Palchaudhuri, R.; Morrison, K. C.; Lucas, P. W.; Palmer, A. E.; Fan, T. M.; Hergenrother, P. J., Differential effects of procaspase-3 activating compounds in the induction of cancer cell death. *Mol. Pharmaceutics* 2012, 9, 1425-1434.
11. Hsu, D. C.; Roth, H. S.; West, D. C.; Botham, R. C.; Novotny, C. J.; Schmid, S. C.; Hergenrother, P. J., Parallel Synthesis and Biological Evaluation of 837 Analogues of Procaspase-Activating Compound 1 (PAC-1). *ACS Comb. Sci.* 2012, 14, 44-50.
12. Mori, A.; Miyakawa, Y.; Ohashi, E.; Haga, T.; Maegawa, T.; Sajiki, H., Pd/C-catalyzed chemoselective hydrogenation in the presence of diphenylsulfide. *Org. Lett.* 2006, 8, 3279-3281.
13. Clark, D. E., Rapid calculation of polar molecular surface area and its application to the prediction of transport phenomena. 2. Prediction of blood-brain bather penetration. *J. Pharm. Sci.* 1999, 88, 815-821.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect, such as activation or inhibition. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. In one embodiment, an effective amount refers to an amount of the active agent described herein that are effective, either alone or in combination with a pharmaceutical carrier, upon single- or multiple-dose administration to a cell or a subject, e.g., a patient, at inhibiting the growth or proliferation, inducing the killing, or preventing the growth of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. In some embodiments, the terms "treatment", "treat" or "treated" can refer to (i) prevention of tumor growth or regrowth of the tumor (prophylaxis), (ii) a reduction or elimination of symptoms or the disease of interest (therapy) or (iii) the elimination or destruction of the tumor (cure).

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. Additionally, the terms "induce," "inhibit," "potentiate," "elevate," "increase," "decrease," or the like denote quantitative differences between two states, and can refer to at least statistically significant differences between the two states. For example, "an amount effective to inhibit the growth of hyperproliferative cells" means that the rate of growth of the cells can be, in some embodiments, at least statistically significantly different from the untreated cells. Such terms can be applied herein to, for example, rates of proliferation.

The phrase "inhibiting the growth or proliferation" of the hyperproliferative cell, e.g. neoplastic cell, refers to the slowing, interrupting, arresting, or stopping its growth and metastasis, and does not necessarily indicate a total elimination of the neoplastic growth.

The term "cancer cell" encompasses definitions as broadly understood in the art. In one embodiment, the term refers to an abnormally regulated cell that can contribute to a clinical condition of cancer in a human or animal. In some embodiments, the term can refer to a cultured cell line or a cell within or derived from a human or animal body. A cancer cell can be of a wide variety of differentiated cell, tissue, or organ types as is understood in the art, and also as described herein.

Thus, the term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body.

The invention provides methods for treating cancer and cancerous conditions. The term "cancerous condition" relates to any condition where cells are in an abnormal state or condition that is characterized by rapid proliferation or neoplasia. A cancerous condition may be malignant or non-malignant (e.g. precancerous condition) in nature. To farther describe a "cancerous condition", the terms "hyperproliferative", "hyperplastic", "hyperplasia", "malignant", "neoplastic" and "neoplasia" can be used. These terms can be used interchangeably and are meant to include all types of hyperproliferative growth, hyperplastic growth, cancerous growths or oncogenic processes, metastatic tissues or malignantly transformed cells, tissues or organs, irrespective of histopathologic type, stage of invasiveness, or cancerous determination (e.g. malignant and nonmalignant).

The term "neoplasia" refers to new cell growth that results in a loss of responsiveness to normal growth controls, e.g., neoplastic cell growth. A "hyperplasia" refers to cells undergoing an abnormally high rate of growth. However, these terms can be used interchangeably, as their context will reveal, referring generally to cells experiencing abnormal cell growth rates. "Neoplasias" and "hyperplasias" include tumors, which may be either benign, premalignant, carcinoma in-situ, malignant, solid or non-solid.

Compounds described herein have been found to be particularly effective for treating cancers of the brain. Cancers of the brain include, but are not limited to, oligodendrogliomas and glioblastomas including glioblastoma multiforme (GBM). Tissues affected by the cancerous cells can be in the brain itself (e.g., the cranium or the central spinal canal) or in lymphatic tissue, in blood vessels, in the cranial nerves, in the brain envelopes (meninges), skull, pituitary gland, or pineal gland. Specific forms of brain cancer that can be treated include astrocytomas, chondromas, chondrosarcomas, chordomas, CNS (central nervous system) lymphomas, craniopharyngiomas, ependymomas, gangliogliomas, ganglioneuromas (also called gangliocytomas), gliomas, including astrocytomas, oligodendrogliomas, and ependymomas, hemangioblastomas (also called vascular tumors), primitive neuroectodermal tumors (PNET) such as medulloblastomas, meningiomas, and vestibular schwannomas (formerly known as acoustic neuroma/schwannoma).

The compounds described herein can also be used to treat metastatic tumors that invade the intracranial sphere from cancers originating in other organs of the body. These conditions are typically referred to as secondary brain tumors. Secondary brain tumors that can be treated with a compound described herein include metastatic tumors of the brain that originate from lung cancer, breast cancer, malignant melanoma, kidney cancer, colon cancer, and other carcinomas.

Other examples of cancerous conditions that are within the scope of the invention include, but are not limited to, neuroblastomas and osteogenic carcinomas (e.g. cancer of the bone or neoplastic growth of tissue in bone). Examples of malignant primary bone tumors that can be treated with a compound described herein include osteosarcomas, chondrosarcomas, Ewing's sarcoma, fibrosarcomas, and the like, and secondary bone tumors such as metastatic lesions that have spread from other organs, including carcinomas of the breast, lung, and prostate.

The terms alkyl, cycloalkyl, alkenyl, alkenyl, aryl, amino groups, alkoxy, halo, haloalkyl, heteroaryl, heterocycle, and ester are well known in the art and have their art-recognized definitions, such as described in U.S. Patent Publication No. 2012/0040995 (Hergenrother et al.).

For example, the term "alkyl" refers to a monoradical branched or unbranched saturated hydrocarbon chain preferably having from 1 to 22 carbon atoms and to cycloalkyl groups having one or more rings having 3 to 22 carbon atoms. Short alkyl groups are those having 1 to 6 carbon atoms including methyl, ethyl, propyl, butyl, pentyl and hexyl groups, including all isomers thereof. Long alkyl groups are those having 8-22 carbon atoms and preferably those having 12-22 carbon atoms as well as those having 12-20 and those having 16-18 carbon atoms.

Thus, the term "alkyl" can refer to a monoradical branched or unbranched saturated hydrocarbon chain preferably having from 1 to 22 carbon atoms. Short alkyl groups are those having 1 to 12 carbon atoms including methyl, ethyl, propyl, butyl, pentyl and hexyl groups, including all isomers thereof. Long alkyl groups are those having 12-22 carbon atoms. The group may be a terminal group or a bridging group.

Alkyl, heteroalkyl, aryl, heteroaryl, and heterocycle groups, and cyclic and/or unsaturated versions thereof, can be R groups of Formula I, and each group can be optionally substituted. Thus, in various embodiments, any one or more of the substituents below can be an R group (e.g., $R^1$, $R^2$, $R^2$, $R^{10}$, $R^{20}$, $R^{30}$, etc.) of a group or formula described herein. The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and cyano. Additionally, suitable substituent groups can be, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O⁻, —S(=O)$_2$OH, —S(=O)$_2$R, —OS(=O)$_2$R, —S(=O)$_2$NR, —S(=O)R, —OP(=O)O$_2$RR, —P(=O)O$_2$RR, —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle (alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on a substituted group, such as an R group (e.g., $R^1$, $R^2$, $R^2$, $R^{10}$, $R^{20}$, $R^{30}$, etc.) of a group or formula described herein.

The term "cycloalkyl" refers to cyclic alkyl groups of from 3 to 22 carbon atoms having a single cyclic ring or multiple condensed rings. Cycloalkyl groups include those having 3-8 member rings and those having 5 and 6 member rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like.

The term "alkenyl" refers to a monoradical of a branched or unbranched unsaturated hydrocarbon group preferably having from 2 to 22 carbon atoms and to cycloalkenyl groups having one or more rings having 3 to 22 carbon atoms wherein at least one ring contains a double bond. Alkenyl groups may contain one or more double bonds (C=C) which may be conjugated. Preferred alkenyl groups are those having 1 or 2 double bonds. Short alkenyl groups are those having 2 to 6 carbon atoms including ethylene (vinyl) propylene, butylene, pentylene and hexylene groups, including all isomers thereof. Long alkenyl groups are those having 8-22 carbon atoms and preferably those having 12-22 carbon atoms as well as those having 12-20 carbon atoms and those having 16-18 carbon atoms. The term "cycloalkenyl" refers to cyclic alkenyl groups of from 3 to 22 carbon atoms having a single cyclic ring or multiple condensed rings in which at least one ring contains a double bond (C=C). Cycloalkenyl groups include, by way of example, single ring structures such as cyclopropenyl, cyclobutenyl, cyclopentenyl, cyclooctenyl, cylcooctadienyl and cyclooctatrienyl. The term allyl refers to the alkenyl group $CH_2$—$CH$=$CH_2$.

The term "alkynyl" refers to a monoradical of an unsaturated hydrocarbon preferably having from 2 to 22 carbon atoms and having one or more triple bonds (C C). Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms.

The term "aryl" refers to a group containing an unsaturated aromatic carbocyclic group of from 6 to 22 carbon atoms having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Aryls include phenyl, naphthyl and the like. Aryl groups may contain portions that are alkyl, alkenyl or akynyl in addition to the the unsaturated aromatic ring(s). The term "alkaryl" refers to the aryl groups containing alkyl portions, i.e., -alkylene-aryl and -substituted alkylene-aryly. Such alkaryl groups are exemplified by benzyl (—$CH_2$-phenyl), phenethyl and the like.

Alkyl, alkenyl, alkynyl and aryl groups are optionally substituted as described herein (the term(s) can include substituted variations) and may contain 1-8 non-hydrogen substituents dependent upon the number of carbon atoms in the group and the degree of unsaturation of the group. All such variable as described herein can be unsubstituted (in which any variables groups that can be hydrogen are hydrogen) or substituted with one or more non-hydrogen substituents selected from halogen, including fluorine, chlorine, bromine or iodine, C1-C3 haloalkyl, hydroxyl (OH), thiol (HS—), C1-C6 alkyl, C1-C3 alkyl, C1-C6 alkoxy, C1-C3 alkoxy, phenyl, benzyl, alkenyl, C2-C4 alkenyl, alkynyl, C2-C4 alkynyl, —$NH_2$, —NR'H, —NR'R", R'CO—, R'R"NCO—, R'CO—NH—, or R'CO—NR'—, where R' and R" are C1-C6 alkyl, C1-C3 alkyl or phenyl.

The term "amino" refers to the group —$NH_2$ or to the group NR' R" where each R' and R" is independently selected from the group consisting of hydrogen, alkyl or aryl groups.

Haloalkyl" refers to alkyl as defined herein substituted by one or more halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 2 to 22 carbon atoms having 1 to 4 heteroatoms selected from oxygen, nitrogen and sulfur within at least one ring (if there is more than one ring). Heteroaryl groups may be optionally substituted. Heteroaryl groups include among others those having 5 and 6-member rings and those having one or two nitrogens in the ring, those having one or two oxygens in the ring as well as those having one or two sulfurs in the ring.

The term "heterocycle" or "heterocyclic" refers to a monoradical saturated or unsaturated group having a single ring or multiple condensed rings, from 2-22 carbon atoms and from 1 to 6 hetero atoms, preferably 1 to 4 heteroatoms, selected from nitrogen, sulfur, phosphorus, and/or oxygen within at least one ring. Heterocyclic groups may be substituted. Rings preferably have 3-10 members and more specifically have 5 or 6 members.

The term "ester" refers to chemical entities as understood in the art and in particular can include groups of the form (RCO—).

The compounds of this invention include all novel stereochemical isomers arising from the substitution of disclosed compounds.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antitumor agents and have higher potency and/or reduced toxicity as compared to PAC-1. Compounds of the invention can be more potent and less toxic than PAC-1, and/or avoid a potential site of catabolic metabolism encountered with PAC-1, i.e., they have a different metabolic profile than PAC-1.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

General Procedure for the Synthesis of PAC-1 Analogues

To a 16×150 mm test tube were added hydrazide (1.7 equiv), aldehyde (1.0 equiv), 2-ethoxyethanol (1 mL), and 1.2 M HCl (10 mol %). The tubes were shaken on a Büchi Syncore parallel synthesizer at 110° C. until all aldehyde had reacted (as monitored by ESI-MS). The reaction mixture was cooled to room temperature (~23° C.), and polystyrene-benzaldehyde (3.5 equiv) was added. The reaction mixture was shaken at 25-80° C. until no hydrazide remained (as monitored by ESI-MS). The reaction mixture was cooled to room temperature, and the resin was filtered and washed with 2-ethoxyethanol. The filtrate was dried under high vacuum to afford the PAC-1 analogue.

Example 2

Parallel Synthesis of PAC-1 Analogues

Reactions requiring anhydrous conditions were conducted under a positive atmosphere of nitrogen or argon in oven-dried glassware. Standard syringe techniques were used for anhydrous addition of liquids. Unless otherwise noted, all starting materials, solvents, and reagents were acquired from commercial suppliers and used without further purification. Flash chromatography was performed using 230-400 mesh silica gel. Compounds 1{1}, 1{2}, 1{3}, 1{4}, 1{5}, 1{6}, 2{24}, 2{25}, 2{26}, and PAC-1 were synthesized as previously reported.

Compound Analysis.

NMR experiments were recorded either in $CDCl_3$ (Sigma), $CD_3OD$ (Sigma) or $(CD_3)_2CO$ (Sigma) on a Varian Unity 400 MHz or 500 MHz spectrometer with residual undeuterated solvent as the internal reference for $^1$H-NMR and $^{13}$C-NMR experiments and 1% $CFCl_3/CDCl_3$ as the external reference for $^{19}$F-NMR experiments. Chemical shift, δ (ppm); coupling constants, J (Hz); multiplicity (s=singlet, d=doublet, t=triplet, q=quartet, m=multiplet, br=broad); and integration are reported. High-resolution mass spectral data was recorded on a Micromass Q-Tof Ultima hybrid quadrupole/time-of-flight ESI mass spectrometer at the University of Illinois Mass Spectrometry Laboratory.

General Procedure A: Synthesis of 1-benzylpiperazines.

Anhydrous piperazine (6.0 equiv.) was suspended in THF (0.45 M benzyl halide). The mixture was heated to reflux until piperazine fully dissolved. Upon dissolution, the substituted benzyl halide (1.0 equiv.) was added to the reaction mixture. A white solid immediately formed. The reaction mixture was stirred at reflux for 2.5 hours. The mixture was cooled to room temperature. The solid was filtered and washed with THF and EtOAc. The combined filtrates were concentrated to 10% of the original volume. The concentrate was poured into a separatory funnel with 5% brine/$H_2O$ made basic (pH>12) with KOH. The aqueous layer was extracted with DCM and EtOAc. The organic layers were combined, dried over $Na_2SO_4$, and concentrated. The crude product was purified by silica gel column chromatography to yield pure 1-benzylpiperazine.

General Procedure B: Synthesis of Ethyl Esters.

The substituted 1-benzylpiperazine (1.0 equiv.) was dissolved in acetone (0.5 M), and chloroform was added to some reaction mixtures as needed to fully dissolve the 1-benzylpiperazine. $NaHCO_3$ (1.25 equiv.) was added, and the mixture was stirred at room temperature. Ethyl chloroacetate (1.1 equiv.) was then added dropwise. The reaction mixture was stirred overnight at reflux. The reaction mixture was cooled to room temperature. The solid was filtered and washed with acetone. The filtrate was concentrated. The crude product was purified by silica gel column chromatography to yield pure ethyl ester.

General Procedure C: Synthesis of Hydrazides.

The substituted ethyl 2-(4-benzylpiperazin-1-yl)acetate (1.0 equiv.) was dissolved in EtOH (0.5 M). The solution was stirred, and anhydrous hydrazine (3.0-4.0 equiv.) was added dropwise. The reaction mixture was stirred at reflux overnight. The reaction mixture was cooled to room temperature and concentrated. The concentrate was transferred to a separatory funnel containing 1:1 brine:$H_2O$ made basic (pH>12) with KOH. The aqueous layer was extracted with DCM (3×) and EtOAc (1×). The combined organic layers were dried over $MgSO_4$ and concentrated. The crude product was purified by silica gel column chromatography or recrystallization to yield pure hydrazide.

The corresponding 1-benzoylpiperazines can be prepared by analogous methods, for example, as described and illustrated herein, using appropriate optionally substituted benzoyl halides or benzoic acids, and amide forming conditions such as an amine base (e.g., $Et_3N$) or EDC-HCl and DMAP.

Various useful preparatory methods are described in U.S. Patent Publication Nos. 2011/0257398 (Hergenrother et al.), 2012/0040995 (Hergenrother et al.), and 2013/0096133 (Hergenrother et al.). The invention is also directed to compounds described in the aforementioned publications where the piperazine nitrogen distal to the hydrazide moiety is connected to a carbonyl as opposed to a methylene.

Scheme B. Starting materials used for synthesis of hydrazides.

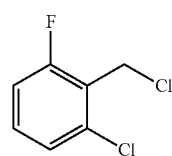

4{7}

-continued
| | |
|---|---|
| 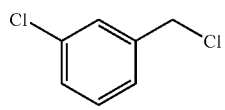 | 4{8} |
| 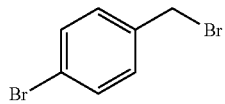 | 4{9} |
| 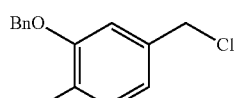 | 4{10} |
| 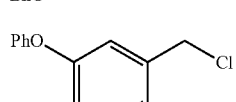 | 4{11} |
| 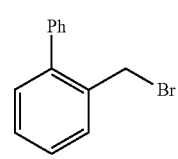 | 4{12} |
| 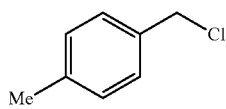 | 4{13} |
| 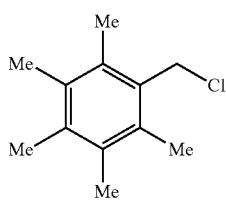 | 4{14} |
| 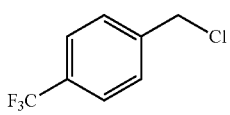 | 4{15} |
| 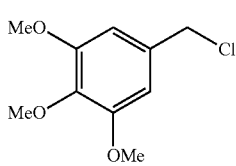 | 4{16} |
| 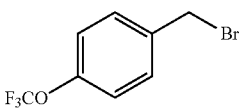 | 4{17} |
| 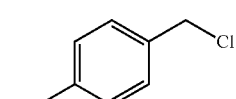 | 4{18} |
| 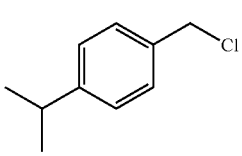 | 4{19} |
-continued
| | |
|---|---|
| 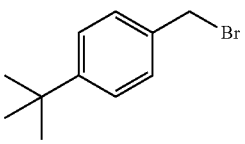 | 4{20} |
| 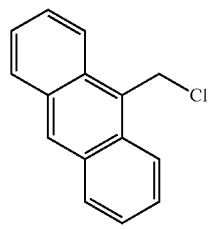 | 4{21} |
| 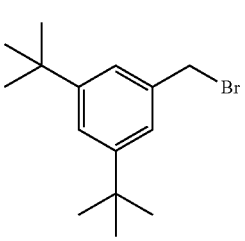 | 4{22} |
| 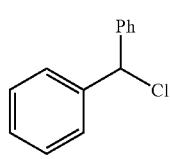 | 4{23} |
| 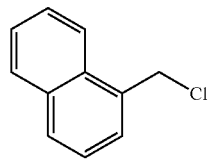 | 4{24} |
| 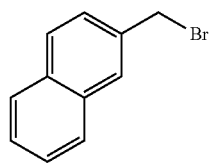 | 4{25} |
| 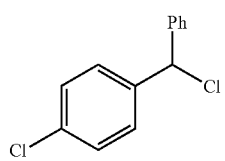 | 4{26} |
| 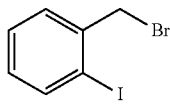 | 4{27} |

One example of a general synthetic procedure is described below.

1-(4-(tert-butyl)benzyl)piperazine (5 {20})

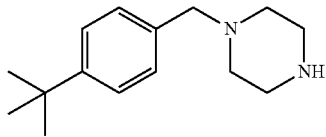 [SMILES: CC(C)(C)c1ccc(CN2CCNCC2)cc1]

Synthesized according to General Procedure A: 4-tert-butylbenzyl bromide (4 {20}, 4.05 mL, 22.0 mmol, 1 equiv.), piperazine (11.4 g, 132.1 mmol, 6 equiv.), THF (48.1 mL). Purification with flash column chromatography on silica gel (4:1 EtOAc:MeOH) afforded 5{20} (3.75 g, 73%) as a beige solid. $^1$H-NMR (500 MHz, CDCl$_3$): δ 7.30 (d, 2H, J=8.5 Hz), 7.22 (d, 2H, J=8.5 Hz), 3.44 (s, 2H), 2.85 (t, 4H, J=5.0 Hz), 2.38 (br s, 4H), 1.54 (br s, 1H), 1.29 (s, 9H). $^{13}$C-NMR (125 MHz, CDCl$_3$): δ 149.6, 134.7, 128.7, 124.8, 63.1, 54.3, 45.9, 34.2, 31.2.

Ethyl 2-(4-(4-(tert-butyl)benzyl)piperazin-1-yl)acetate (6{20})

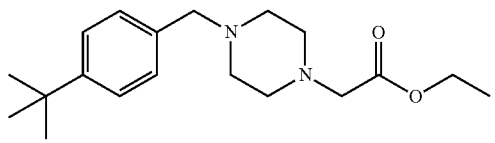 [SMILES: CCOC(=O)CN1CCN(Cc2ccc(C(C)(C)C)cc2)CC1]

Synthesized according to General Procedure B: 5{20} (3.46 g, 14.9 mmol, 1 equiv.), ethyl chloroacetate (1.8 mL, 16.4 mmol, 1.1 equiv.), NaHCO$_3$ (1.56 g, 18.6 mmol, 1.25 equiv.), acetone (29.8 mL), chloroform (10 mL). Purification with flash column chromatography on silica gel (1:1 hexanes:EtOAc) afforded 6{20} (4.25 g, 90%) as an orange oil. $^1$H-NMR (500 MHz, CDCl$_3$): δ 7.31 (d, 2H, J=8.5 Hz), 7.21 (d, 2H, J=8.5 Hz), 4.16 (q, 2H, J=7.0 Hz), 3.48 (s, 2H), 3.18 (s, 2H), 2.58 (br s, 4H), 2.51 (br s, 4H), 1.29 (s, 9H), 1.24 (t, 3H, J=7.0 Hz). $^{13}$C-NMR (125 MHz, CDCl$_3$): δ 170.1, 149.7, 134.7, 128.8, 124.9, 62.5, 60.4, 59.4, 53.0, 52.6, 34.3, 31.3, 14.1.

2-(4-(4-(tert-butyl)benzyl)piperazin-1-yl)acetohydrazide (1{20})

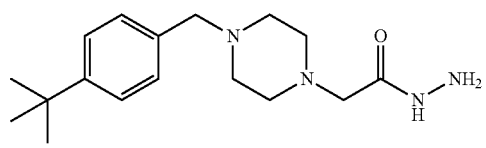 [SMILES: CC(C)(C)c1ccc(CN2CCN(CC(=O)NN)CC2)cc1]

Synthesized according to General Procedure C: 6{20} (4.12 g, 12.9 mmol, 1 equiv.), anhydrous hydrazine (1.2 mL, 38.8 mmol, 3 equiv.), ethanol (26.0 mL). Purification by silica gel column chromatography (4:1 EtOAc:MeOH) afforded 1{20} (3.36 g, 84%) as a beige solid. $^1$H-NMR (500 MHz, CDCl$_3$): δ 8.17 (br s, 1H), 7.31 (d, 2H, J=8.5 Hz), 7.20 (d, 2H, J=8.5 Hz), 3.85 (br s, 2H), 3.46 (s, 2H), 3.05 (s, 2H), 2.52 (br s, 4H), 2.45 (br s, 4H), 1.30 (s, 9H). $^{13}$C-NMR (125 MHz, CDCl$_3$): δ 170.4, 149.9, 134.5, 128.7, 125.0, 62.4, 60.5, 53.5, 52.9, 34.3, 31.3.

N'-(3-allyl-2-hydroxybenzylidene)-2-(4-(4-(tert-butyl)benzyl)piperazin-1-yl)acetohydrazide (3{20,24})

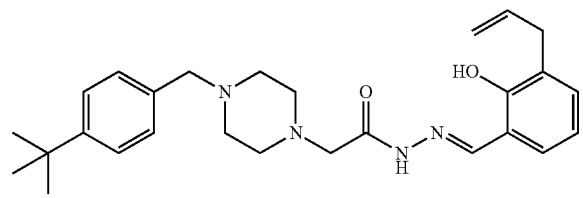 [SMILES: C=CCc1cccc(/C=N/NC(=O)CN2CCN(Cc3ccc(C(C)(C)C)cc3)CC2)c1O]

To a stirred solution of hydrazide 1{20} (100 mg, 0.33 mmol, 1.0 equiv.) and aldehyde 2{24} (53.5 mg, 0.33 mmol, 1.0 equiv.) in EtOH (2.2 mL, 0.15 M) was added 1.2 M HCl (7 mol %). The reaction mixture was stirred at reflux overnight. The reaction mixture was cooled to room temperature and concentrated. The crude product was purified by silica gel column chromatography (gradient, 0-10% MeOH/EtOAc) to yield 3{20,24} (102.0 mg, 0.23 mmol, 68.9%) as a light brown solid. $^1$H-NMR (500 MHz, CDCl$_3$): δ 11.31 (br s, 1H), 10.09 (br s, 1H), 8.38 (s, 1H), 7.36 (d, 2H, J=8.5 Hz), 7.25 (d, 2H, J=8.5 Hz), 7.19 (d, 1H, J=7.5 Hz), 7.08 (dd, 1H, J=1.5, 7.5 Hz), 6.85 (t, 1H, J=7.5 Hz), 6.04 (tdd, 1H, J=6.5, 10.0, 16.5 Hz), 5.12-5.06 (m, 2H), 3.52 (s, 2H), 3.47 (d, 2H, J=6.5 Hz), 3.20 (s, 2H), 2.63 (br s, 4H), 2.54 (br s, 4H), 1.33 (s, 9H). $^{13}$C-NMR (125 MHz, CDCl$_3$): δ 165.8, 156.3, 151.1, 150.0, 136.4, 134.6, 132.2, 129.1, 128.7, 128.1, 125.1, 118.9, 116.8, 115.6, 62.5, 60.9, 53.6, 53.0, 34.4, 33.8, 31.3. HRMS (ESI): 449.2915 (M+1); calcd. for C$_{27}$H$_{37}$N$_4$O$_2$: 449.2917.

Example 3

Biological Evaluation of Analogues of PAC-1

Materials.

All reagents were obtained from Fisher unless otherwise indicated. All buffers were made with MilliQ purified water. Ac-DEVD-pNA was synthesized as previously described.[5] Luria broth (LB) was obtained from EMD. Doxorubicin was obtained from Sigma. Caspase Activity Buffer contains 50 mM HEPES, 300 mM NaCl, 1.5 mM TCEP, 0.01% TritonX-100 and is Chelex® treated. Ni NTA Binding Buffer contains 50 mM Tris (pH 8.0), 300 mM NaCl, and 10 mM imidazole. Ni NTA Wash Buffer contains 50 mM Tris (pH 8.0), 300 mM NaCl, and 50 mM imidazole. Ni NTA Elution Buffer contains 50 mM Tris (pH 8.0), 300 mM NaCl, and 500 mM imidazole. Annexin V Binding Buffer contains 10 mM HEPES pH 7.4, 140 mM NaCl, 2.5 mM CaCl2, 0.1% BSA. The C-terminal 6×His-tagged procaspase-3 proteins were expressed as described below.

Cell Culture.

U-937 cells were obtained from the American Type Culture Collection and maintained at low passage number. Cultures were maintained in RPMI 1640 supplemented with 10% fetal bovine serum and 1% penicillin-streptomycin and grown at 37° C. and 5% CO$_2$.

Cell Death Assay for Initial Screen.

Compound (2 μL of a 10 mM DMSO solution) was added in singlet by direct addition to a well containing 998 μL U-937 cells (1×10⁶) in RPMI 1640 media (10% FBS) at a final compound concentration of 20 μM. After incubation at 37° C. for 24 h, the cells were transferred to flow cytometry tubes, washed, and resuspended in Annexin V binding buffer. The cells were double stained with FITC-Annexin V and propidium iodide and a cell population of at least 10,000 events was collected by the LSR II flow cytometer. Percent viable cells (Annexin V—negative, propidium iodide—negative) were determined using FCS Express software.

72 Hour $IC_{50}$ Cell Death Assay.

U-937 human lymphoma cells were plated into the wells of 96 well plate at a density of 15,000 cells per well in 99 μL of RPMI 1640 growth media with 10% FBS and 1% pen-strep. To each well was added 1 μL of compound stock solutions in DMSO at varying concentrations such that the cells were treated with concentrations between 0 μM and 100 μM compound. Each concentration was tested in quintuplicate per plate. In each plate 5 wells received 20 μM doxorubicin as a positive death control and 5 wells received 1 μL of DMSO as a negative control. The plates were then incubated at 37° C. and 5% CO2 for 72 hours.

After the 72 hour incubation period, the plates were analyzed using a Sulforhodamine B assay (Vichai and Kirtikara, Nat Protoc 2006, 1, 1112-1116). Specifically, to each well of the plate 25 μL of a 50% (w/v) solution of trichloroacetic acid in H₂O was added and the plates were incubated for 4 hours at 4° C. The plates were then washed gently with water five times. The plates were allowed to air dry after which 100 μL of a 0.057% (w/v) Sulforhodamine B in a 1% (v/v) acetic acid solution was added to each well for 30 minutes at room temperature. The plates were gently washed 5 times with 1% (v/v) acetic acid and air dried. 200 μL of 10 mM Tris base (pH 10.4) was added to each well and the plates were placed on an orbital shaker for thirty minutes. The level of SRB was quantified fluorometrically at excitation and emission wavelengths 488 and 585 nm, respectively, on a Molecular Devices plate reader and the percent cell death calculated and normalized to the positive control (100% cell death) and the negative control (0% cell death). The percent cell death was averaged for each compound concentration and plotted as a function of compound concentration. The data were fit to a logistical dose response curve using Table curve 2D and the $IC_{50}$ value was calculated. The experiment was repeated three times and the average of the calculated $IC_{50}$ values was reported. The standard error of the mean (SEM) was determined and reported for the triplicate experiments.

Induction of Apoptosis by Hit Compounds.

U-937 Cells (1 mL of 6×10⁵ cells/mL) were treated with 10 μL of 750 μM DMSO solutions of the compounds to achieve a final concentration of 7.5 μM. The cells were incubated at 37° C. for 24 hours. The cells were harvested via centrifugation (200 g for 5 minutes), washed with PBS (2 mL), and resuspended in 450 μL Annexin V Binding Buffer. To each sample was added 3.5 μL of FITC conjugated Annexin V stain (Southern Biotech) and 3.5 μL of propidium iodide (Sigma) to a final concentration of 50 μg/mL. Cell populations were analyzed on a Benton Dickinson LSR II cell flow cytometer.

Recombinant Expression and Purification of Procaspase-3.

Techniques adapted from Hergenrother and coworkers (Putt et al., Nat Chem Biol 2006, 2, 543-550). A 20 mL volume of an overnight culture of Rosetta E. coli containing the procaspase-3 (wild-type) expression plasmid was seeded into 2 L of LB media containing ampicillin. The culture was grown to an OD600=1.0, at which point protein expression was induced via addition of IPTG (to 1 mM); the culture was allowed to grow for 30 additional minutes. Cells were then harvested (10 minute spins at 10,000×g and re-suspended in NTA binding buffer (300 mM NaCl, 50 mM Tris, 10 mM imidazole, pH 8.0). The cells were lysed on ice via sonication. The cell lysate was then spun at 35,000×g for 35 mM The supernatant was decanted and 1 mL of nickel-NTA resin was added. The cell lysate was incubated for 45 minutes at 4° C. The resin was loaded on a column, washed with 10 mL NTA binding buffer followed by 10 mL NTA wash buffer (300 mM NaCl, 50 mM Tris, 50 mM imidazole, pH 8.0). The proteins were eluted in 0.5 mL fractions with 10 mL of NTA elution buffer (300 mM NaCl, 50 mM Tris, 500 mM imidazole, pH 8.0). Fractions containing protein were pooled and further purified to remove any contaminating zinc by applying the protein to a PD-10 column (GE Healthcare) charged with Caspase Activity Buffer that had been treated with Chelex® resin. The resulting concentration was determined using the Edelhoch method and the molar absorptivity of procaspase-3 of 26150 $M^{-1}$ $cm^{-1}$. Protein stocks were flash-frozen in liquid nitrogen and stored at −80° C.

Procaspase-3 Activity Assay.

In a 384-well plate recombinantly expressed, zinc-free procaspase-3 (wild type, at 1 μM) in Caspase Activity Buffer (50 mM HEPES, 300 mM NaCl, 1.5 mM TCEP, 0.01% TritonX-100) was incubated at 37° C. in the presence of 3.5 μM $ZnSO_4$ and the basal activity was assessed via the addition of Ac-DEVD-pNA (final concentration in well of 200 μM). The absorbance at 405 nm was monitored with a SpectraMax plate reader (Molecular Devices). After the basal activity was determined, DMSO, PAC-1 and analogues were added to each sample to a final concentration of 25 μM. Activity of each treatment was assessed at 5, 20, 40 and 60 minutes via 5-minute kinetic reads. The slope of each data set was used to determine the activity of the protein. Activity was normalized to a percent activity at each time point using a zinc-free sample and a zinc-inhibited sample treated with DMSO.

Example 4

Compound Preparation

Materials and Methods.
General

All reactions requiring anhydrous conditions were conducted under a positive atmosphere of nitrogen or argon in oven-dried glassware.

Standard syringe techniques were used for anhydrous addition of liquids. Unless otherwise noted, all starting materials, solvents, and reagents were acquired from commercial suppliers and used without further purification. Flash chromatography was performed using 230-400 mesh silica gel. Syntheses of 46a,[1] 46b,[2] 46h,[3] 47a,[2] 50,[2] PAC-1 (1),[1] and S-PAC-1 (2)[2] have been described previously.

Compound Analysis.

NMR experiments were recorded either in $CDCl_3$ (Sigma or Cambridge), $CD_3OD$ (Sigma), or $(CD_3)_2CO$ (Sigma or Cambridge) on a Varian Unity 500 MHz spectrometer with residual undeuterated solvent as the internal reference for ¹H-NMR and ¹³C-NMR, and $C_6F_6$ as the internal reference for ¹⁹F-NMR. Chemical shift, δ (ppm); coupling constants, J (Hz); multiplicity (s=singlet, d=doublet, t=triplet, q=quartet, quint=quintet, sext=sextet, m=multiplet, br=broad); and integration are reported. High-resolution mass spectral data was recorded on a Micromass Q-Tof Ultima hybrid quadrupole/time-of-flight ESI mass spectrometer or a Micromass 70-VSE at the University of Illinois Mass Spectrometry Laboratory.

General Procedure A: Synthesis of Dialkylated Piperazines.

To a round-bottom flask were added benzyl halide (1.0 equiv.), K$_2$CO$_3$ (3.0 equiv.), and acetone (0.2 M). The mixture was stirred, and 50 (1.5 equiv.) was added. The reaction mixture was stirred at reflux overnight. The reaction mixture was cooled to room temperature. The solid was filtered and washed with acetone. The filtrate was concentrated, and the product was purified by silica gel column chromatography.

General Procedure B: Synthesis of Amides.

To an oven-dried round-bottom flask were added 50 (1.0 equiv.), anhydrous tetrahydrofuran (0.2 M), and freshly distilled Et$_3$N (2.0 equiv.). The solution was stirred at 0° C. under N$_2$, and the benzoyl chloride (1.0 equiv.) was added. The reaction mixture was stirred overnight at room temperature under N$_2$. The reaction mixture was diluted with EtOAc and washed with sat. NaHCO$_3$ (2×), H$_2$O, and brine. The organic layer was dried over MgSO$_4$, filtered, and concentrated. The product was purified by silica gel column chromatography.

General Procedure C: Synthesis of Hydrazides.

To a round-bottom flask were added ethyl ester (1.0 equiv.) and EtOH or 2:1 EtOH:MeOH (0.5 M). The solution was stirred, and anhydrous hydrazine (4.0 equiv.) was added dropwise. The reaction mixture was stirred at reflux overnight. The reaction mixture was cooled to room temperature and concentrated. The resulting residue was partitioned between CH$_2$Cl$_2$/1:1 brine:0.1 M KOH. The layers were separated, and the aqueous layer was extracted with CH$_2$Cl$_2$ (2×). The combined organic layers were dried over MgSO$_4$, filtered, and concentrated. Purification by silica gel column chromatography or recrystallization yielded pure hydrazide.

Ethyl 2-(4-benzoylpiperazin-1-yl)acetate (51c)

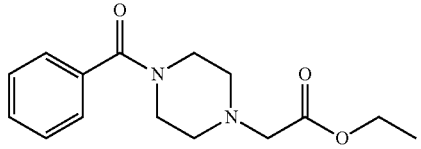 [SMILES: CCOC(=O)CN1CCN(C(=O)c2ccccc2)CC1]

Synthesized according to General Procedure B: 50 (2.45 g, 14.2 mmol, 1.0 equiv.), anhydrous tetrahydrofuran (70 mL, 0.2 M), freshly distilled Et$_3$N (4.0 mL, 28.4 mmol, 2.0 equiv.), benzoyl chloride (54c, 2.0 g, 1.7 mL, 1.0 equiv.). Purification by silica-gel column chromatography (50-100% EtOAc/hexanes) afforded 51c (2.87 g, 73.1%) as a pale yellow oil. $^1$H-NMR (500 MHz, CDCl$_3$) δ 7.41-7.38 (m, 5H), 4.19 (q, 2H, J=7.0 Hz), 3.85 (br s, 2H), 3.48 (br s, 2H), 3.25 (s, 2H), 2.68 (br s), 2.54 (br s, 2H), 1.27 (t, 3H, J=7.0 Hz). $^{13}$C-NMR (125 MHz, CDCl$_3$) δ 170.5, 170.2, 135.9, 129.9, 128.7, 127.3, 61.0, 59.4, 53.3 (br), 52.8 (br), 47.8 (br), 42.1 (br), 14.4. HRMS (ESI): 277.1552 (M+1); calcd. for C$_{15}$H$_{21}$N$_2$O$_3$: 277.1552.

2-(4-benzoylpiperazin-1-yl)acetohydrazide (46c)

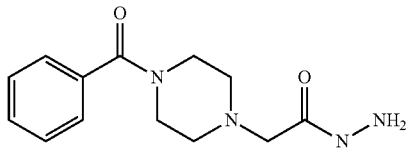

Synthesized according to General Procedure C: 51c (2.87 g, 10.4 mmol, 1.0 equiv.), anhydrous hydrazine (1.31 mL, 41.6 mmol, 4.0 equiv.), EtOH (20 mL, 0.5 M). 46c (1.41 g, 51.5%) was obtained as a white solid after extraction without further purification. $^1$H-NMR (500 MHz, CDCl$_3$) δ 8.10 (s, 1H), 7.39-7.34 (m, 5H), 3.84 (br s, 2H), 3.77 (br s, 2H), 3.43 (br s, 2H), 3.08 (s, 2H), 2.56 (br s, 2H), 2.44 (br s, 2H). $^{13}$C-NMR (125 MHz, CDCl$_3$) δ 170.5, 169.9, 135.5, 130.0, 128.7, 127.1, 60.6, 53.9 (br), 53.4 (br), 47.7 (br), 42.2 (br). HRMS (ESI): 263.1513 (M+1); calcd. for C$_{13}$H$_{19}$N$_4$O$_2$: 263.1508.

Ethyl 2-(4-(4-cyanobenzyl)piperazin-1-yl)acetate (51d)

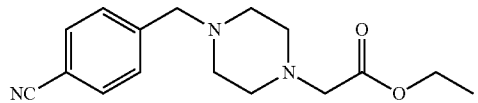 [SMILES: CCOC(=O)CN1CCN(Cc2ccc(C#N)cc2)CC1]

Synthesized according to General Procedure A: 4-(bromomethyl)benzonitrile (54d, 2.0 g, 10.2 mmol, 1.0 equiv.), 50 (2.64 g, 15.3 mmol, 1.5 equiv.), K$_2$CO$_3$ (4.22 g, 30.6 mmol, 3.0 equiv.), acetone (50 mL, 0.2 M). Purification by silica gel column chromatography (50-100% EtOAc/hexanes) afforded 51d (2.71 g, 92.3%) as a yellow solid. $^1$H-NMR (500 MHz, CDCl$_3$) δ 7.60 (d, 2H, J=8.0 Hz), 7.44 (d, 2H, J=8.0 Hz), 4.18 (q, 2H, J=7.0 Hz), 3.55 (s, 2H), 3.20 (s, 2H), 2.61 (br s, 4H), 2.51 (br s, 4H), 1.26 (t, 3H, J=7.0 Hz). $^{13}$C-NMR (125 MHz, CDCl$_3$) δ 170.4, 144.4, 132.3, 129.7, 119.2, 111.0, 62.5, 60.8, 59.6, 53.1, 53.1, 14.4. HRMS (ESI): 288.1718 (M+1); calcd. for C$_{16}$H$_{22}$N$_3$O$_2$: 288.1712.

2-(4-(4-cyanobenzyl)piperazin-1-yl)acetohydrazide (46d)

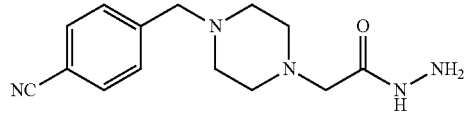 [SMILES: N#Cc1ccc(CN2CCN(CC(=O)NN)CC2)cc1]

Synthesized according to General Procedure C: 51d (2.71 g, 9.43 mmol, 1.0 equiv.), anhydrous hydrazine (1.18 mL, 37.7 mmol, 4.0 equiv.), EtOH (19 mL, 0.5 M). 46d (1.73 g, 67.1%) was obtained as an off-white solid after extraction without further purification. $^1$H-NMR (500 MHz, CDCl$_3$) δ 8.10 (br s, 1H), 7.60 (d, 2H, J=8.0 Hz), 7.43 (d, 2H, J=8.5 Hz), 3.84 (br d, 2H, J=5.0 Hz), 3.55 (s, 2H), 3.08 (s, 2H), 2.55 (br s, 4H), 2.46 (br s, 4H). $^{13}$C-NMR (125 MHz, CDCl$_3$) δ 170.6, 144.1, 132.4, 129.6, 119.1, 111.2, 62.5, 60.8, 53.8, 53.3. HRMS (ESI): 274.1673 (M+1); calcd. for C$_{14}$H$_{20}$N$_5$O: 274.1668.

Ethyl 2-(4-(4-cyanobenzoyl)piperazin-1-yl)acetate (51e)

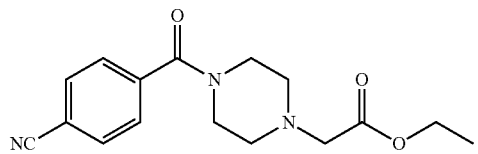 [SMILES: CCOC(=O)CN1CCN(C(=O)c2ccc(C#N)cc2)CC1]

Synthesized according to General Procedure B: 50 (5.20 g, 30.2 mmol, 1.0 equiv.), anhydrous tetrahydrofuran (150 mL, 0.2 M), freshly distilled Et₃N (8.4 mL, 60.4 mmol, 2.0 equiv.), 4-cyanobenzoyl chloride (54e, 5.0 g, 30.2 mmol, 1.0 equiv.). Purification by silica gel column chromatography (0-10% MeOH/EtOAc) afforded 51e (5.95 g, 65.4%) as a white solid. $^1$H-NMR (500 MHz, CDCl₃) δ 7.68 (d, 2H, J=8.0 Hz), 7.47 (d, 2H, J=8.0 Hz), 4.14 (q, 2H, J=7.0 Hz), 3.80 (br s, 2H), 3.37 (br s, 2H), 3.23 (s, 2H), 2.67 (br s, 2H), 2.53 (br s, 2H), 1.23 (t, 3H, J=7.0 Hz). $^{13}$C-NMR (125 MHz, CDCl₃) δ 170.0, 168.3, 140.1, 132.5, 127.9, 118.2, 113.6, 60.9, 59.0, 52.9, 52.3, 47.5, 42.1, 14.3. HRMS (ESI): 302.1501 (M+1); calcd. for $C_{16}H_{20}N_3O_3$: 302.1505.

2-(4-(4-cyanobenzoyl)piperazin-1-yl)acetohydrazide (46e)

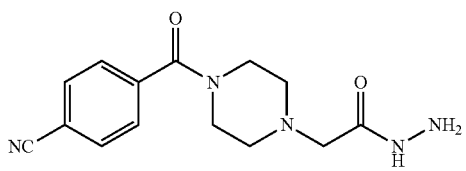 [SMILES: N#Cc1ccc(C(=O)N2CCN(CC(=O)NN)CC2)cc1]

Synthesized according to General Procedure C with modification as noted: 51e (5.59 g, 18.6 mmol, 1.0 equiv.), anhydrous hydrazine (2.4 mL, 74.4 mmol, 4.0 equiv.), EtOH (35 mL, 0.5 M). After extraction with CH₂Cl₂, the aqueous layer was extracted with EtOAc (3×). 46e (2.98 g, 55.8%) was obtained as an off-white solid after extraction without further purification. $^1$H-NMR (500 MHz, CDCl₃) δ 8.02 (br s, 1H), 7.70 (d, 2H, J=8.5 Hz), 7.48 (d, 2H, J=8.5 Hz), 3.86 (br d, 2H, J=3.5 Hz), 3.78 (br s, 2H), 3.37 (br s, 2H), 3.11 (s, 2H), 2.60 (br s, 2H), 2.46 (br s, 2H). $^{13}$C-NMR (125 MHz, CDCl₃) δ 169.8, 168.4, 139.8, 132.6, 127.9, 118.1, 113.8, 60.6, 53.8 (br), 53.3 (br), 47.6 (br), 42.2 (br). HRMS (ESI): 288.1464 (M+1); calcd. for $C_{14}H_{18}N_5O_2$: 288.1461.

Ethyl 2-(4-(4-fluorobenzyl)piperazin-1-yl)acetate (51f)

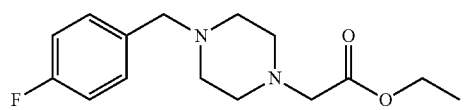 [SMILES: CCOC(=O)CN1CCN(Cc2ccc(F)cc2)CC1]

Synthesized according to General Procedure A: 4-fluorobenzyl chloride (54f, 2.5 g, 2.1 mL, 17.3 mmol, 1.0 equiv.), 50 (4.48 g, 26.0 mmol, 1.5 equiv.), K₂CO₃ (7.19 g, 52.0 mmol, 3.0 equiv.), acetone (90 mL, 0.2 M). Purification by silica gel column chromatography (gradient, 50-100% EtOAc/hexanes) afforded 51f (3.66 g, 75.4%) as a yellow oil. $^1$H-NMR (500 MHz, CDCl₃) δ 7.24-7.20 (m, 2H), 6.95-6.91 (m, 2H), 4.13 (q, 2H, J=7.0 Hz), 3.42 (s, 2H), 3.15 (s, 2H), 2.55 (br s, 4H), 2.46 (br s, 4H), 1.21 (t, 3H, J=7.0 Hz). $^{13}$C-NMR (125 MHz, CDCl₃) δ 170.3, 162.0 (d, $J_{C-F}$=243.5 Hz), 133.9, 130.6 (d, $J_{C-F}$=8.0 Hz), 115.0 (d, $J_{C-F}$=21.0 Hz), 62.2, 60.6, 59.6, 53.1, 52.8, 14.3. $^{19}$F-NMR (470 MHz, CDCl₃) δ –119.1. HRMS (ESI): 281.1659 (M+1); calcd. for $C_{15}H_{22}FN_2O_2$: 281.1665.

2-(4-(4-fluorobenzyl)piperazin-1-yl)acetohydrazide (46f)

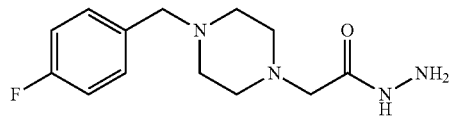 [SMILES: NNC(=O)CN1CCN(Cc2ccc(F)cc2)CC1]

Synthesized according to General Procedure C: 51f (3.0 g, 10.7 mmol, 1.0 equiv.), anhydrous hydrazine (1.4 mL, 42.8 mmol, 4.0 equiv.), EtOH (20 mL, 0.5 M). 46f (2.59 g, 91.1%) was obtained as a white solid after extraction without further purification. $^1$H-NMR (500 MHz, CDCl₃) δ 8.15 (br s, 1H), 7.22-7.19 (m, 2H), 6.95-6.91 (m, 2H), 3.84 (br s, 2H), 3.40 (s, 2H), 3.01 (s, 2H), 2.47 (br s, 4H), 2.39 (br s, 4H). $^{13}$C-NMR (125 MHz, CDCl₃) δ 170.5, 162.0 (d, $J_{C-F}$=243.6 Hz), 133.7 (d, $J_{C-F}$=2.8 Hz), 130.6 (d, $J_{C-F}$=8.3 Hz), 115.1 (d, $J_{C-F}$=21.1 Hz), 62.0, 60.6, 53.7, 53.0. $^{19}$F-NMR (470 MHz, CDCl₃) δ –118.9. HRMS (ESI): 267.1630 (M+1); calcd. for $C_{13}H_{20}FN_4O$: 267.1621.

Ethyl 2-(4-(4-fluorobenzoyl)piperazin-1-yl)acetate (51g)

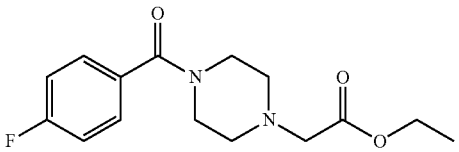 [SMILES: CCOC(=O)CN1CCN(C(=O)c2ccc(F)cc2)CC1]

Synthesized according to General Procedure B: 50 (2.58 g, 15.0 mmol, 1.0 equiv.), anhydrous tetrahydrofuran (30 mL, 0.5 M), freshly distilled Et₃N (4.2 mL, 30.0 mmol, 2.0 equiv.), 4-fluorobenzoyl chloride (54 g, 1.8 mL, 15.0 mmol, 1.0 equiv.). Purification by silica gel column chromatography (50-100% EtOAc/hexanes) afforded 51g (3.74 g, 84.7%) as a pale yellow oil. $^1$H-NMR (500 MHz, CDCl₃) δ $^1$H-NMR (500 MHz, CDCl₃) δ 7.38-7.34 (m, 2H), 7.06-7.01 (m, 2H), 4.13 (q, 2H, J=7.0 Hz), 3.77 (br s, 2H), 3.43 (br s, 2H), 3.21 (s, 2H), 2.61 (br s, 2H), 2.52 (br s, 2H), 1.22 (t, 3H, J=7.0 Hz). $^{13}$C-NMR (125 MHz, CDCl₃) δ 170.0, 169.4, 163.5 (d, $J_{C-F}$=248.1 Hz), 131.8, 129.5 (d, $J_{C-F}$=8.3 Hz), 115.6 (d, $J_{C-F}$=22.0 Hz), 60.8, 59.1, 52.8 (br), 47.8 (br), 42.2 (br), 14.3. $^{19}$F-NMR (470 MHz, CDCl₃) δ –113.4. HRMS (ESI): 295.1457 (M+1); calcd. for $C_{15}H_{20}FN_2O_3$: 295.1458.

2-(4-(4-fluorobenzoyl)piperazin-1-yl)acetohydrazide (46g)

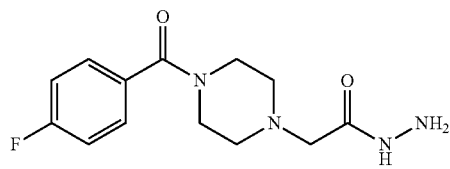 [SMILES: NNC(=O)CN1CCN(C(=O)c2ccc(F)cc2)CC1]

Synthesized according to General Procedure C: 51g (3.73 g, 12.7 mmol, 1.0 equiv.), anhydrous hydrazine (1.6 mL, 50.8 mmol, 4.0 equiv.), EtOH (25 mL, 0.5 M). 46g (2.28 g, 64.1%) was obtained as a white solid after extraction without further purification. ¹H-NMR (500 MHz, CDCl₃) δ ¹H-NMR (500 MHz, CDCl₃) δ 8.09 (br s, 1H), 7.37-7.33 (m, 2H), 7.06-7.02 (m, 2H), 3.85 (br s, 2H), 3.70 (br s, 2H), 3.42 (br s, 2H), 3.06 (s, 2H), 2.48 (br s, 4H). ¹³C-NMR (125 MHz, CDCl₃) δ 169.8, 169.5, 163.5 (d, $J_{C-F}$=249.1 Hz), 131.5 (d, $J_{C-F}$=2.8 Hz), 129.4 (d, $J_{C-F}$=9.1 Hz), 115.7 (d, $J_{C-F}$=22.0 Hz), 60.6, 53.5 (br), 47.7 (br), 42.3 (br). ¹⁹F-NMR (470 MHz, CDCl₃) δ −113.1. HRMS (ESI): 281.1409 (M+1); calcd. for $C_{13}H_{18}FN_4O_2$: 281.1414.

Ethyl 2-(4-(4-(trifluoromethyl)benzoyl)piperazin-1-yl)acetate (51i)

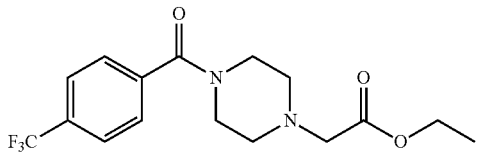 [SMILES: CCOC(=O)CN1CCN(C(=O)c2ccc(C(F)(F)F)cc2)CC1]

Synthesized according to General Procedure B: 50 (2.58 g, 15.0 mmol, 1.0 equiv.), anhydrous tetrahydrofuran (30 mL, 0.5 M), freshly distilled Et₃N (4.2 mL, 30.0 mmol, 2.0 equiv.), 4-(trifluoroemthyl)benzoyl chloride (54i, 2.2 mL, 15.0 mmol, 1.0 equiv.). Purification by silica-gel column chromatography (50-100% EtOAc/hexanes) afforded 51i (4.01 g, 77.5%) as a yellow oil. ¹H-NMR (500 MHz, CDCl₃) δ 7.65 (d, 2H, J=8.0 Hz), 7.49 (d, 2H, J=8.0 Hz), 4.16 (q, 2H, J=7.0 Hz), 3.82 (br s, 2H), 3.41 (br s, 2H), 3.24 (s, 2H), 2.68 (br s, 2H), 2.54 (br s, 2H), 1.24 (t, 3H, J=7.0 Hz). ¹³C-NMR (125 MHz, CDCl₃) δ170.1, 168.9, 139.4 131.8 (q, $J_{C-F}$=32.6 Hz), 127.6, 125.7 (q, $J_{C-F}$=3.8 Hz), 123.8 (q, $J_{C-F}$=271.0 Hz), 60.9, 59.1, 53.0 (br), 52.5 (br), 47.6 (br), 42.2 (br), 14.3. ¹⁹F-NMR (470 MHz, CDCl₃) δ −66.0. HRMS (ESI): 345.1430 (M+1); calcd. for $C_{16}H_{20}F_3N_2O_3$: 345.1426.

2-(4-(4-(trifluoromethyl)benzoyl)piperazin-1-yl) acetohydrazide (46i)

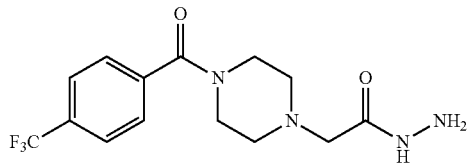 [SMILES: NNC(=O)CN1CCN(C(=O)c2ccc(C(F)(F)F)cc2)CC1]

Synthesized according to General Procedure C: 51i (4.00 g, 11.6 mmol, 1.0 equiv.), anhydrous hydrazine (1.5 mL, 46.4 mmol, 4.0 equiv.), EtOH (25 mL, 0.5 M). 46i (2.35 g, 61.4%) was obtained as a white solid after extraction without further purification. ¹H-NMR (500 MHz, CDCl₃) δ 8.09 (br s, 1H), 7.62 (d, 2H, J=8.0 Hz), 7.45 (d, 2H, J=8.0 Hz), 3.88 (br s, 2H) 3.75 (br s, 2H), 3.35 (br s, 2H), 3.07 (s, 2H), 2.56 (br s, 2H), 2.42 (br s, 2H). ¹³C-NMR (125 MHz, CDCl₃) δ169.8, 168.9, 139.1 131.8 (q, $J_{C-F}$=32.1 Hz), 127.5, 125.7 (q, $J_{C-F}$=3.6 Hz), 123.7 (q, $J_{C-F}$=271.1 Hz), 60.5, 53.7 (br), 53.2 (br), 47.6 (br), 42.2 (br). ¹⁹F-NMR (470 MHz, CDCl₃) δ −66.0. HRMS (ESI): 331.1374 (M+1); calcd. for $C_{14}H_{18}F_3N_4O_2$: 331.1382.

3-propylsalicylaldehyde (47b)

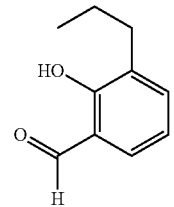

To a round-bottom flask were added aldehyde 47a (1.62 g, 10.0 mmol, 1.0 equiv.), 5% Pd/C (324 mg, 20 wt % of 47a), diphenyl sulfide (17 µL, 0.10 mmol, 0.010 equiv.), and EtOAc (40 mL, 0.25 M). The reaction mixture was stirred overnight at room temperature under an atmosphere of H₂ (balloon pressure). The reaction mixture was filtered through Celite and washed thoroughly with EtOAc. The filtrate was concentrated to afford aldehyde 47b (1.50 g, 91.7%) as a yellow oil. ¹H-NMR (500 MHz, CDCl₃) δ 11.27 (s, 1H), 9.88 (s, 1H), 7.41-7.38 (m, 2H), 6.95 (t, 1H, J=7.5 Hz), 2.64 (t, 2H, J=7.5 Hz), 1.65 (sext, 2H, J=7.5 Hz), 0.96 (t, 3H, J=7.5 Hz). ¹³C-NMR (125 MHz, CDCl₃) δ 197.0, 160.0, 137.4, 131.7, 131.4, 120.4, 119.6, 31.3, 22.7, 14.1. HRMS (EI): 164.08383 (M⁺); calcd. for $C_{10}H_{12}O_2$: 164.08373.

2-(allyloxy)-5-fluorobenzaldehyde (53b)

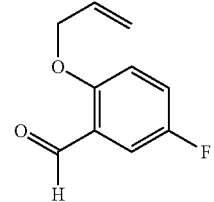

To a round bottom flask were added 5-fluorosalicylaldehyde (47c, 4.0 g, 28.5 mmol, 1.0 equiv.), potassium carbonate (4.92 g, 35.6 mmol, 1.25 equiv.), and DMF (20 mL). Allyl bromide (3.7 mL, 42.8 mmol, 1.5 equiv.) was added slowly to the mixture. The reaction mixture was stirred overnight at room temperature. The reaction mixture was diluted with water (50 mL) and extracted with ethyl acetate (3×50 mL). The combined organic layers were washed with water (2×25 mL), 0.1M KOH (2×25 mL), water (2×25 mL), and brine (2×25 mL), dried over MgSO₄, filtered, and concentrated to yield 53b (4.64 g, 90.2%) as a pale yellow liquid. ¹H-NMR (500 MHz, CDCl₃) δ 10.47 (d, 1H, J=3.0 Hz), 7.50 (dd, 1H, J=3.0, 8.0 Hz), 7.23 (ddd, 1H, J=3.0, 7.5, 11.0 Hz), 6.95 (dd, 1H, J=4.0, 9.0 Hz), 6.06 (tdd, 1H, J=5.0, 10.5, 17.5 Hz), 5.44 (qd, 1H, J=1.5, 17.0 Hz), 5.34 (ddd, 1H, J=1.5, 2.5, 10.5 Hz), 4.64 (td, 2H, J=1.5, 5.0 Hz). ¹³C-NMR (125 MHz, CDCl₃) δ 188.8, 157.4 (d, $J_{C-F}$=1.9 Hz), 157.2 (d, $J_{C-F}$=240.5 Hz), 132.4, 126.1 (d, $J_{C-F}$=5.9 Hz), 122.6 (d, $J_{C-F}$=23.8 Hz), 118.5, 114.8 (d, $J_{C-F}$=7.1 Hz), 114.2 (d, $J_{C-F}$=23.1 Hz), 70.1. ¹⁹F-NMR (470 MHz, CDCl₃) δ −125.5. HRMS (EI): 180.05789 (M⁺); calcd. for $C_{10}H_9FO_2$: 180.05866.

3-allyl-5-fluorosalicylaldehyde (47d)

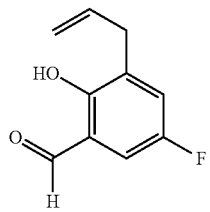

53b (4.64 g, 25.8 mmol) was heated neat overnight at 200° C. The crude product was purified by silica gel column chromatography (hexanes) to yield 47d (2.24 g, 48.3%) as a bright yellow oil. $^1$H-NMR (500 MHz, CDCl$_3$) δ 11.10 (s, 1H), 9.83 (s, 1H), 7.17 (dd, 1H, J=3.0, 9.0 Hz), 7.11 (dd, 1H, J=3.0, 7.5 Hz) 5.96 (tdd, 1H, J=6.5, 10.0, 17.0 Hz), 5.16-5.14 (m, 1H), 5.12 (qd, 1H, J=1.5, 11.0 Hz), 3.42 (d, 2H, J=6.5 Hz). $^{13}$C-NMR (125 MHz, CDCl$_3$) δ 195.9 (d, $J_{C-F}$=2.5 Hz), 156.0 (d, $J_{C-F}$=1.0 Hz), 155.7 (d, $J_{C-F}$=238.8 Hz), 135.1, 131.6 (d, $J_{C-F}$=6.4 Hz), 124.8 (d, $J_{C-F}$=23.6 Hz), 119.8 (d, $J_{C-F}$=6.4 Hz), 117.3, 116.0 (d, $J_{C-F}$=22.3 Hz), 33.2. $^{19}$F-NMR (470 MHz, CDCl$_3$) δ −126.9. HRMS (EI): 180.05761 (M$^+$); calcd. for C$_{10}$H$_9$FO$_2$: 180.05866.

5-fluoro-2-hydroxy-3-propylbenzaldehyde (47e)

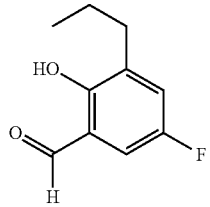

To a round-bottom flask were added aldehyde 47d (1.10 g, 6.11 mmol, 1.0 equiv.), 5% Pd/C (220 mg, 20 wt % of 47d), diphenyl sulfide (10 μL, 0.061 mmol, 0.010 equiv.), and EtOAc (25 mL, 0.25 M). The reaction mixture was stirred overnight at room temperature under an atmosphere of H$_2$ (balloon pressure). The reaction mixture was filtered through Celite and washed thoroughly with EtOAc. The filtrate was concentrated to afford aldehyde 47e (991 mg, 89.3%) as a yellow oil. $^1$H-NMR (500 MHz, CDCl$_3$) δ 11.06 (br s, 1H), 9.80 (s, 1H), 7.12 (dd, 1H, J=3.0, 9.0 Hz), 7.06 (dd, 1H, J=3.0, 7.5 Hz), 2.62 (t, 2H, J=7.5 Hz), 1.63 (sext, 2H, J=7.5 Hz), 0.96 (t, 3H, J=7.5 Hz). $^{13}$C-NMR (125 MHz, CDCl$_3$) δ 195.9 (d, $J_{C-F}$=2.5 Hz), 156.3 (d, $J_{C-F}$=1.0 Hz), 155.5 (d, $J_{C-F}$=238.1 Hz), 133.9 (d, $J_{C-F}$=6.3 Hz), 124.7 (d, $J_{C-F}$=23.1 Hz), 119.6 (d, $J_{C-F}$=6.5 Hz), 115.4 (d, $J_{C-F}$=22.4 Hz), 31.2, 22.4, 14.0. $^{19}$F-NMR (470 MHz, CDCl$_3$) δ −127.3. HRMS (EI): 182.07392 (M$^+$); calcd. for C$_{10}$H$_{11}$FO$_2$: 182.07431.

General Procedure D: Synthesis of PAC-1 Analogues

To a 16×150 mm test tube were added hydrazide (1.0 equiv.), aldehyde (1.0 equiv.), EtOH or 2:1 MeOH:MeCN (0.15 M), and 1.2 M HCl (7 mol%). The reaction mixture was shaken overnight at reflux on a Büchi Syncore parallel synthesizer. The reaction mixture was cooled to room temperature, concentrated, and purified by silica gel column chromatography or recrystallization to yield pure PAC-1 analogue.

N'-(3-allyl-2-hydroxybenzylidene)-2-(4-benzoylpiperazin-1-yl)acetohydrazide (3)

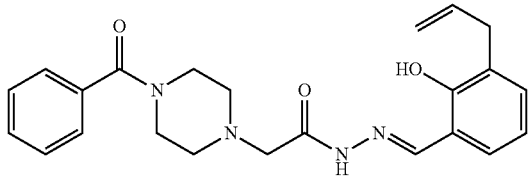 [SMILES: C=CCc1cccc(/C=N/NC(=O)CN2CCN(C(=O)c3ccccc3)CC2)c1O]

Synthesized according to General Procedure D, but in a round-bottom flask: 46c (262 mg, 1.0 mmol, 1.0 equiv.), 47a (162 mg, 1.0 mmol, 1.0 equiv.), 1.2 M HCl (58 μL, 0.070 mmol, 0.070 equiv.), EtOH (7 mL, 0.15 M). Purification by silica gel column chromatography (gradient, 0-10% MeOH/EtOAc) yielded 3 (284 mg, 69.8%) as a white solid. $^1$H-NMR (500 MHz, CDCl$_3$) δ 11.19 (s, 1H), 9.94 (br s, 1H), 8.45 (s, 1H), 7.46-7.41 (m, 5H), 7.20 (d, 1H, J=6.5 Hz), 7.08 (dd, 1H, J=1.5, 7.5 Hz), 6.85 (t, 1H, J=7.0 Hz), 6.03 (tdd, 1H, J=6.5, 10.0, 16.5 Hz), 5.10-5.05 (m, 2H), 3.88 (br s, 2H), 3.58 (s, 2H), 3.52 (br s, 2H), 3.45 (d, 2H, J=6.5 Hz), 3.25 (s, 2H), 2.68 (br s, 2H), 2.61 (br s, 2H). $^{13}$C-NMR (125 MHz, CDCl$_3$) δ 170.6, 165.4, 156.4, 151.6, 136.5, 135.4, 132.5, 130.2, 129.3, 128.8, 128.3, 127.1, 119.2, 116.9, 115.8, 61.0, 53.7, 53.1, 47.6, 42.1, 33.9. HRMS (ESI): 407.2077 (M+1); calcd. for C$_{23}$H$_{27}$N$_4$O$_3$: 407.2083.

N'-(3-allyl-2-hydroxybenzylidene)-2-(4-(4-cyanobenzyl)piperazin-1-yl)acetohydrazide (4)

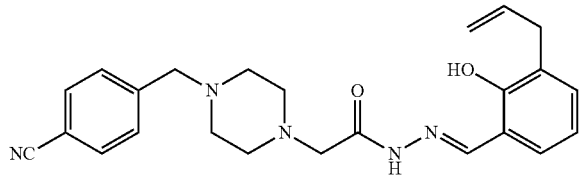 [SMILES: C=CCc1cccc(/C=N/NC(=O)CN2CCN(Cc3ccc(C#N)cc3)CC2)c1O]

Synthesized according to General Procedure D: 46d (273 mg, 1.0 mmol, 1.0 equiv.), 47a (162 mg, 1.0 mmol, 1.0 equiv.), 1.2 M HCl (58 μL, 0.070 mmol, 0.070 equiv.), EtOH (7 mL, 0.15 M). Purification by silica gel column chromatography (gradient, 0-15% MeOH/EtOAc) yielded 4 (367 mg, 87.7%) as a white solid. $^1$H-NMR (500 MHz, CDCl$_3$) δ 11.25 (br s, 1H), 9.99 (br s, 1H), 8.40 (s, 1H), 7.61 (d, 2H, J=8.0 Hz), 7.44 (d, 2H, J=8.0 Hz), 7.18 (dd, 1H, J=1.5, 7.5 Hz), 7.07 (dd, 1H, J=1.5, 7.5 Hz), 6.84 (t, 1H, J=7.5 Hz), 6.02 (tdd, 1H, J=6.5, 10.0, 16.5 Hz), 5.11-5.04 (m, 2H), 3.58 (s, 2H), 3.44 (d, 2H, J=7.0 Hz), 3.19 (s, 2H), 2.63 (br s, 4H), 2.53 (br s, 4H). $^{13}$C-NMR (125 MHz, CDCl$_3$) δ 165.9, 156.5, 151.5, 144.0, 136.6, 132.5, 132.4, 129.6, 129.3, 128.4, 119.2, 119.1, 117.0, 115.8, 111.2, 62.4, 61.1, 53.8, 53.2, 34.0. HRMS (ESI): 418.2242 (M+1); calcd. for $C_{24}H_{28}N_5O_2$: 418.2243.

N'-(3-allyl-2-hydroxybenzylidene)-2-(4-(4-cyanobenzoyl)piperazin-1-yl)acetohydrazide (5)

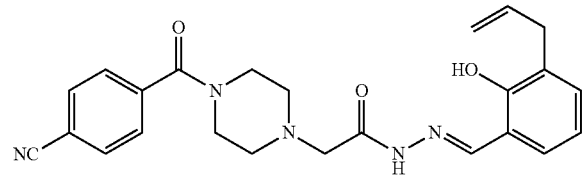 [SMILES: C=CCc1cccc(/C=N/NC(=O)CN2CCN(C(=O)c3ccc(C#N)cc3)CC2)c1O]

Synthesized according to General Procedure D: 46e (287 mg, 1.0 mmol, 1.0 equiv.), 47a (162 mg, 1.0 mmol, 1.0 equiv.), 1.2 M HCl (58 μL, 0.070 mmol, 0.070 equiv.), EtOH (7 mL, 0.15 M). Purification by silica gel column chromatography (gradient, 0-10% MeOH/EtOAc) yielded 5 (378 mg, 87.6%) as a light yellow solid. $^1$H-NMR (500 MHz, CDCl$_3$) δ 11.23 (br s, 1H), 9.98 (br s, 1H), 8.32 (s, 1H), 7.69 (d, 2H, J=8.5 Hz), 7.48 (d, 2H, J=8.0 Hz), 7.17 (d, 1H, J=7.0 Hz), 6.99 (dd, 1H, J=1.5, 8.0 Hz), 6.81 (t, 1H, J=7.5 Hz), 5.98 (tdd, 1H, J=6.5, 10.0, 17.0), 5.08-5.02 (m, 2H), 3.85 (br s, 2H), 3.42-3.39 (m, 4H), 3.23 (s, 2H), 2.68 (br s, 2H), 2.86 (br s, 4H). $^{13}$C-NMR (125 MHz, CDCl$_3$) δ 168.4, 165.3, 156.4, 151.7, 139.7, 136.5, 132.6, 132.6, 129.4, 128.2, 127.9, 119.3, 118.1, 116.8, 115.9, 113.8, 60.9, 53.7 (br), 53.3 (br), 47.5 (br), 42.1 (br), 33.9. HRMS (ESI): 432.2034 (M+1); calcd. for $C_{24}H_{26}N_5O_3$: 432.2036.

N'-(3-allyl-2-hydroxybenzylidene)-2-(4-(4-fluorobenzyl)piperazin-1-yl)acetohydrazide (6)

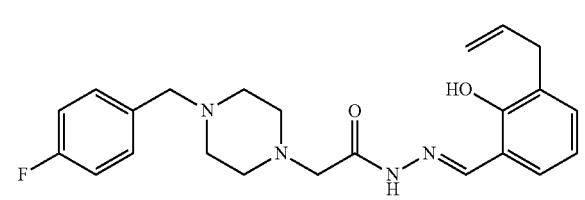 [SMILES: C=CCc1cccc(/C=N/NC(=O)CN2CCN(Cc3ccc(F)cc3)CC2)c1O]

Synthesized according to General Procedure D: H11 (133 mg, 0.50 mmol, 1.0 equiv.), 47a (81 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-10% MeOH/EtOAc) followed by precipitation from Et$_2$O yielded 6 (182 mg, 89.0%) as a white solid. $^1$H-NMR (500 MHz, CDCl$_3$) δ 11.26 (br s, 1H), 10.02 (br s, 1H), 8.41 (s, 1H), 7.29-7.26 (m, 2H), 7.19 (dd, 1H, J=1.5, 7.5 Hz), 7.08 (dd, 1H, J=1.5, 8.0 Hz), 7.02-6.99 (m, 2H), 6.85 (t, 1H, J=7.5 Hz), 6.03 (tdd, 1H, J=6.5, 10.0, 16.5 Hz), 5.11-5.04 (m, 2H), 3.50 (s, 2H), 3.45 (d, 2H, J=6.5 Hz), 3.19 (s, 2H), 2.62 (br s, 4H), 2.51 (br s, 4H). $^{13}$C-NMR (125 MHz, CDCl$_3$) δ 166.0, 162.2 (d, $J_{C-F}$=243.9 Hz), 156.6, 151.5, 136.7, 133.7 (d, $J_{C-F}$=3.1 Hz), 132.5, 130.7 (d, $J_{C-F}$=7.8 Hz), 129.3, 128.4, 119.2, 117.0, 115.8, 115.3 (d, $J_{C-F}$=21.0 Hz), 62.2, 61.2, 53.9, 53.1, 34.0. $^{19}$F-NMR (470 MHz, CDCl$_3$) δ −118.8. HRMS (ESI): 411.2203 (M+1); calcd. for $C_{23}H_{28}FN_4O_2$: 411.2196.

N'-(3-allyl-2-hydroxybenzylidene)-2-(4-(4-fluorobenzoyl)piperazin-1-yl)acetohydrazide (7)

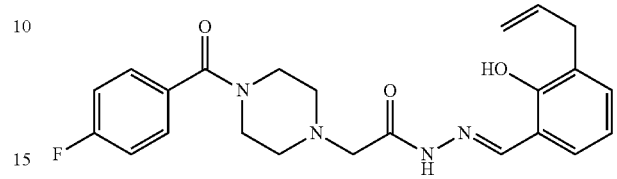

Synthesized according to General Procedure D: H12 (140 mg, 0.50 mmol, 1.0 equiv.), 47a (81 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-10% MeOH/EtOAc) yielded 7 (171 mg, 80.5%) as a white solid. $^1$H-NMR (500 MHz, CDCl$_3$) δ 11.19 (br s, 1H), 9.91 (br s, 1H), 8.43 (s, 1H), 7.43-7.40 (m, 2H), 7.19 (dd, 1H, J=1.0, 7.5 Hz), 7.12-7.09 (m, 2H), 7.06 (dd, 1H, J=1.5, 8.0 Hz), 6.85 (t, 1H, J=7.5 Hz), 6.02 (tdd, 1H, J=6.5, 10.0, 16.5 Hz), 5.10-5.04 (m, 2H), 3.69 (br s, 4H), 3.44 (d, 2H, J=6.5 Hz), 3.24 (s, 2H), 2.64 (br s, 4H). $^{13}$C-NMR (125 MHz, CDCl$_3$) δ 169.6, 165.4, 163.6 (d, $J_{C-F}$=249.1 Hz), 156.4, 151.6, 136.5, 132.5, 131.4 (d, $J_{C-F}$=3.4 Hz), 129.5 (d, $J_{C-F}$=8.4 Hz), 129.3, 128.2, 119.2, 116.8, 115.8, 115.8 (d, $J_{C-F}$=21.5 Hz), 60.9, 53.6 (br), 47.7 (br), 42.3 (br), 33.9. $^{19}$F-NMR (470 MHz, CDCl$_3$) δ −112.8. HRMS (ESI): 425.1989 (M+1); calcd. for $C_{23}H_{26}FN_4O_3$: 425.1989.

N'-(3-allyl-2-hydroxybenzylidene)-2-(4-(4-(trifluoromethyl)benzyl)piperazin-1-yl)acetohydrazide (8)

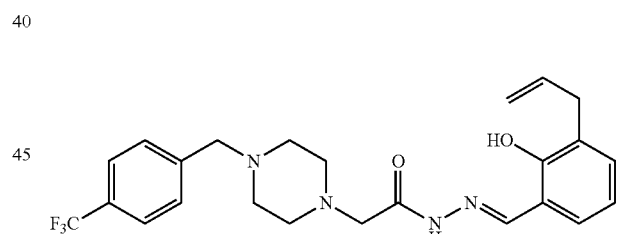

Synthesized according to General Procedure D: H13 (158 mg, 0.50 mmol, 1.0 equiv.), 47a (81 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 8 (125 mg, 54.4%) as a white solid. $^1$H-NMR (500 MHz, CDCl$_3$) δ 11.32 (br s, 1H), 10.11 (br s, 1H), 8.33 (s, 1H), 7.56 (d, 2H, J=8.5 Hz), 7.43 (d, 2H, J=8.0 Hz), 7.17 (dd, 1H, J=1.5, 7.5 Hz), 7.04 (dd, 1H, J=1.5, 8.0 Hz), 6.83 (t, 1H, J=7.5 Hz), 6.02 (tdd, 1H, J=6.5, 10.0, 16.5 Hz), 5.10-5.04 (m, 2H), 3.57 (s, 2H), 3.44 (d, 2H, J=7.0 Hz), 3.19 (s, 2H), 2.63 (br s, 4H), 2.53 (br s, 4H). $^{13}$C-NMR (125 MHz, CDCl$_3$) δ 166.0, 156.4, 151.2, 142.4, 136.6, 132.4, 129.5 (q, $J_{C-F}$=32.0 Hz), 129.3, 129.3, 128.3, 125.3 (q, $J_{C-F}$=3.8 Hz), 123.9 (q, $J_{C-F}$=270.6 Hz), 119.2, 117.0, 115.8, 62.3, 61.0, 53.7, 53.1, 34.0. $^{19}$F-NMR (470

MHz, CDCl$_3$) δ −65.4. HRMS (ESI): 461.2160 (M+1); calcd. for C$_{24}$H$_{28}$F$_3$N$_4$O$_2$: 461.2164.

N'-(3-allyl-2-hydroxybenzylidene)-2-(4-(4-(trifluoromethyl)benzoyl)piperazin-1-yl)acetohydrazide (9)

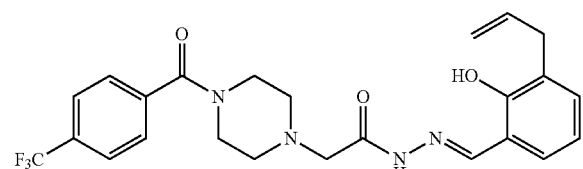

Synthesized according to General Procedure D: H14 (165 mg, 0.50 mmol, 1.0 equiv.), 47a (81 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 9 (211 mg, 89.1%) as a white solid. $^1$H-NMR (500 MHz, CDCl$_3$) δ 11.28 (br s, 1H), 10.13 (br s, 1H), 8.27 (s, 1H), 7.65 (d, 2H, J=8.0 Hz), 7.48 (d, 2H, J=8.0 Hz), 7.15 (d, 1H, J=8.0 Hz), 6.94 (d, 2H, J=7.0 Hz), 6.79 (t, 1H, J=7.5 Hz), 5.97 (tdd, 1H, J=6.5, 10.0, 17.0 Hz), 5.05-5.00 (m, 2H), 3.86 (br s, 2H), 3.43 (br s, 2H), 3.39 (d, 2H, J=6.5 Hz), 3.21 (s, 2H), 2.66 (br s, 2H), 2.58 (br s, 2H). $^{13}$C-NMR (125 MHz, CDCl$_3$) δ 169.0, 165.4, 156.3, 151.5, 139.0, 136.4, 132.5, 131.9 (q, J$_{C-F}$=32.6 Hz), 129.3, 128.2, 127.5, 125.8 (q, J$_{C-F}$=3.5 Hz), 123.7 (q, J$_{C-F}$=271.1 Hz), 119.3, 116.8, 115.8, 60.8, 53.5 (br), 47.5 (br), 42.0 (br), 33.8. $^{19}$F-NMR (470 MHz, CDCl$_3$) δ −66.0. HRMS (ESI): 475.1964 (M+1); calcd. for C$_{24}$H$_{26}$F$_3$N$_4$O$_3$: 475.1957.

2-(4-benzylpiperazin-1-yl)-N'-(2-hydroxy-3-propylbenzylidene)acetohydrazide (10)

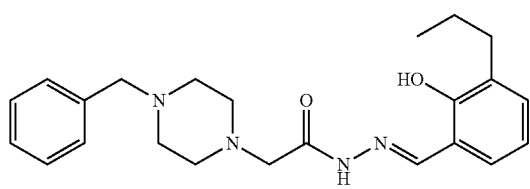 [SMILES: CCCc1cccc(/C=N/NC(=O)CN2CCN(Cc3ccccc3)CC2)c1O]

Synthesized according to General Procedure D, but in a round-bottom flask: 46a (248 mg, 1.0 mmol, 1.0 equiv.), 47b (164 mg, 1.0 mmol, 1.0 equiv.), 1.2 M HCl (58 μL, 0.070 mmol, 0.070 equiv.), EtOH (7 mL, 0.15 M). Purification by silica gel column chromatography (gradient, 0-20% MeOH/EtOAc) yielded 10 (345 mg, 87.3%) as an off-white solid. $^1$H-NMR (500 MHz, CDCl$_3$) δ 11.30 (s, 1H), 10.12 (br s, 1H), 8.31 (s, 1H), 7.35-7.30 (m, 4H), 7.30-7.25 (m, 1H), 7.17 (d, 1H, J=7.5 Hz), 7.03 (d, 1H, J=7.5 Hz), 6.82 (t, 1H, J=7.5 Hz), 3.54 (s, 2H), 3.19 (s, 2H), 2.67 (t, 2H, J=7.5 Hz), 2.62 (br s, 4H), 2.54 (br s, 4H), 1.67 (sext, 2H, J=7.5 Hz), 0.97 (t, 3H, J=7.5 Hz). $^{13}$C-NMR (125 MHz, CDCl$_3$) δ 165.9, 156.7, 151.2, 137.9, 132.5, 130.7, 129.2, 128.8, 128.4, 127.3, 118.9, 116.8, 62.9, 61.0, 53.7, 53.0, 32.0, 22.7, 14.2. HRMS (ESI): 395.2436 (M+1); calcd. for C$_{23}$H$_{31}$N$_4$O$_2$: 395.2447.

4-((4-(2-(2-(2-hydroxy-3-propylbenzylidene)hydrazinyl)-2-oxoethyl)piperazin-1-yl)methyl)benzenesulfonamide (11)

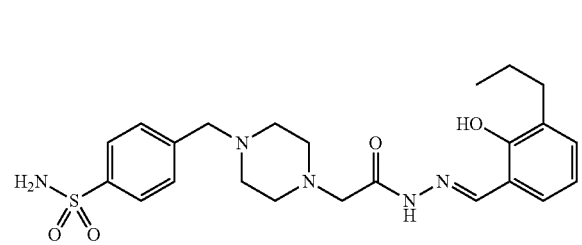 [SMILES: CCCc1cccc(/C=N/NC(=O)CN2CCN(Cc3ccc(S(N)(=O)=O)cc3)CC2)c1O]

Synthesized according to General Procedure D: H2 (164 mg, 0.50 mmol, 1.0 equiv.), 47b (82 mg, 0.50 mmol, 1.0 equiv.), 1.2 M HCl (29 μL, 0.035 mmol, 0.070 equiv.), 2:1 MeOH:MeCN (3 mL, 0.15 M). Purification by silica gel column chromatography (gradient, 0-20% MeOH/EtOAc) yielded 11 (211 mg, 89.0%) as a white solid. $^1$H-NMR (500 MHz, (CD$_3$)$_2$CO) δ 11.78 (s, 1H), 10.76 (br s, 1H), 8.48 (s, 1H), 7.84 (d, 2H, J=8.5 Hz), 7.51 (d, 2H, J=8.5 Hz), 7.17 (d, 1H, J=7.0 Hz), 7.14 (dd, 1H, J=1.5, 8.0 Hz), 6.82 (t, 1H, J=7.5 Hz), 6.54 (br s, 2H), 3.59 (s, 2H), 3.17 (s, 2H), 2.64-2.59 (m, 6H), 2.52 (br s, 4H), 1.63 (sext, 2H, J=7.5 Hz), 0.93 (t, 3H, J=7.5 Hz). $^{13}$C-NMR (125 MHz, (CD$_3$)$_2$CO) δ 166.3, 157.3, 150.9, 144.0, 143.8, 132.7, 130.8, 129.9, 129.6, 126.9, 119.6, 118.3, 62.6, 61.7, 54.3, 53.6, 32.5, 23.4, 14.2. HRMS (ESI): 474.2175 (M+1); calcd. for C$_{23}$H$_{32}$N$_5$O$_4$S: 474.2175.

2-(4-benzoylpiperazin-1-yl)-N'-(2-hydroxy-3-propylbenzylidene)acetohydrazide (12)

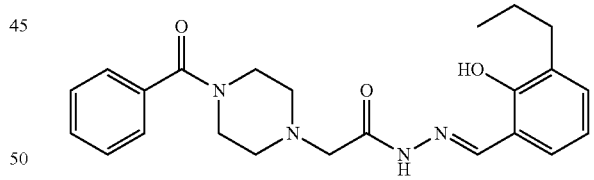

Synthesized according to General Procedure H3 (131 mg, 0.50 mmol, 1.0 equiv.), 47b (82 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 50-100% EtOAc/hexanes, then 5% MeOH/EtOAc) yielded 12 (174 mg, 85.5%) as a white solid. $^1$H-NMR (500 MHz, CDCl$_3$) δ 11.29 (s, 1H), 10.29 (br s, 1H), 8.23 (s, 1H), 7.41-7.34 (m, 5H), 7.13 (dd, 1H, J=1.5, 7.5 Hz), 6.90 (dd, 1H, J=1.5, 7.5 Hz), 6.76 (t, 1H, J=7.5 Hz), 3.80 (br s, 2H), 3.47 (br s, 2H), 3.18 (s, 2H), 2.71-2.52 (m, 6H, Ar—CH$_2$—CH$_2$), 1.61 (sext, 2H, J=7.5 Hz), 0.91 (t, 3H, J=7.5 Hz). $^{13}$C-NMR (125 MHz, CDCl$_3$) δ 170.5, 165.5, 156.6, 151.5, 135.3, 132.5, 130.6, 130.1, 128.8, 128.7, 127.0, 118.9, 116.7, 60.8, 53.6

2-(4-(4-cyanobenzyl)piperazin-1-yl)-N'-(2-hydroxy-3-propylbenzylidene)acetohydrazide (13)

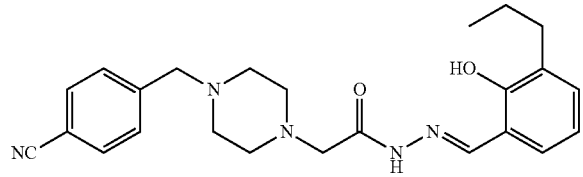 [SMILES: CCCc1cccc(/C=N/NC(=O)CN2CCN(Cc3ccc(C#N)cc3)CC2)c1O]

Synthesized according to General Procedure D: H9 (273 mg, 1.0 mmol, 1.0 equiv.), 47b (164 mg, 1.0 mmol, 1.0 equiv.), 1.2 M HCl (58 μL, 0.070 mmol, 0.070 equiv.), EtOH (7 mL, 0.15 M). Purification by silica gel column chromatography (gradient, 0-15% MeOH/EtOAc) yielded 13 (373 mg, 88.8%) as a white solid. $^1$H-NMR (500 MHz, CDCl$_3$) δ 11.19 (br s, 1H), 9.99 (br s, 1H), 8.37 (s, 1H), 7.60 (d, 2H, J=8.0 Hz), 7.44 (d, 2H, J=7.5 Hz), 7.16 (dd, 1H, J=1.5, 7.5 Hz), 7.04 (dd, 1H, J=1.5, 7.5 Hz), 6.82 (t, 1H, J=7.5 Hz), 3.58 (s, 2H), 3.19 (s, 2H), 2.66-2.63 (m, 6H), 2.52 (br s, 4H), 1.64 (sext, 2H, J=7.5 Hz), 0.95 (t, 3H, J=7.5 Hz). $^{13}$C-NMR (125 MHz, CDCl$_3$) δ 165.8, 156.8, 151.6, 144.0, 132.7, 132.3, 130.8, 129.6, 128.9, 119.1, 119.0, 116.8, 111.2, 62.4, 61.1, 53.8, 53.2, 32.0, 22.8, 14.2. HRMS (ESI): 420.2396 (M+1); calcd. for C$_{24}$H$_{30}$N$_5$O$_2$: 420.2400.

2-(4-(4-cyanobenzoyl)piperazin-1-yl)-N'-(2-hydroxy-3-propylbenzylidene)acetohydrazide (14)

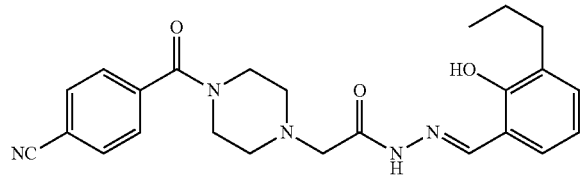 [SMILES: CCCc1cccc(/C=N/NC(=O)CN2CCN(C(=O)c3ccc(C#N)cc3)CC2)c1O]

Synthesized according to General Procedure D: H10 (287 mg, 1.0 mmol, 1.0 equiv.), 47b (164 mg, 1.0 mmol, 1.0 equiv.), 1.2 M HCl (58 μL, 0.070 mmol, 0.070 equiv.), EtOH (7 mL, 0.15 M). Purification by silica gel column chromatography (gradient, 0-15% MeOH/EtOAc) yielded 14 (377 mg, 86.9%) as a light yellow solid. $^1$H-NMR (500 MHz, CDCl$_3$) δ 11.15 (br s, 1H), 9.92 (br s, 1H), 8.32 (s, 1H), 7.71 (d, 2H, J=8.0 Hz), 7.49 (d, 2H, J=7.5 Hz), 7.16 (d, 1H, J=7.0 Hz), 6.98 (dd, 1H, J=1.5, 7.5 Hz), 6.80 (t, 1H, J=7.5 Hz), 3.86 (br s, 2H), 3.44 (br s, 2H), 3.24 (s, 2H), 2.70 (br s, 2H), 2.64-2.57 (m, 4H), 1.62 (sext, 2H, J=7.5 Hz), 0.93 (t, 3H, J=7.5 Hz). $^{13}$C-NMR (125 MHz, CDCl$_3$) δ 168.5, 165.2, 156.7, 152.0, 139.8, 132.9, 132.7, 130.8, 129.0, 127.9, 119.1, 118.1, 116.7, 113.9, 61.0, 53.5 (br), 47.5 (br), 42.1 (br), 32.0, 22.8, 14.2. HRMS (ESI): 434.2188 (M+1); calcd. for C$_{24}$H$_{28}$N$_5$O$_3$: 434.2192.

2-(4-(4-fluorobenzyl)piperazin-1-yl)-N'-(2-hydroxy-3-propylbenzylidene)acetohydrazide (15)

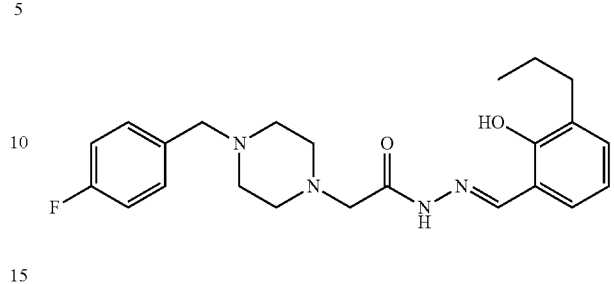

Synthesized according to General Procedure D: H11 (133 mg, 0.50 mmol, 1.0 equiv.), 47b (82 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) followed by precipitation from Et$_2$O yielded 15 (137 mg, 66.4%) as a white solid. $^1$H-NMR (500 MHz, CDCl$_3$) δ 11.26 (br s, 1H), 10.09 (br s, 1H), 8.31 (s, 1H), 7.26 (dd, 2H, J=6.0, 8.0 Hz), 7.16 (dd, 1H, J=1.5, 6.5 Hz), 7.02-6.97 (m, 3H), 6.80 (t, 1H, J=7.5 Hz), 3.48 (s, 2H), 3.18 (s, 2H), 2.65 (t, 2H, J=7.5 Hz), 2.61 (br s, 4H), 2.50 (br s, 4H), 1.65 (sext, 2H, J=7.5 Hz), 0.95 (t, 3H, J=7.5 Hz). $^{13}$C-NMR (125 MHz, CDCl$_3$) δ 165.9, 162.1 (d, $J_{C-F}$=243.6 Hz), 156.7, 151.3, 133.7 (d, $J_{C-F}$=3.0 Hz), 132.5, 130.7, 130.6 (d, $J_{C-F}$=7.8 Hz), 128.9, 118.9, 116.8, 115.2 (d, $J_{C-F}$=21.0 Hz), 62.1, 61.0, 53.8, 53.0, 32.0, 22.8, 14.2. $^{19}$F-NMR (470 MHz, CDCl$_3$) δ −118.8. HRMS (ESI): 413.2361 (M+1); calcd. for C$_{23}$H$_{30}$FN$_4$O$_2$: 413.2353.

2-(4-(4-fluorobenzoyl)piperazin-1-yl)-N'-(2-hydroxy-3-propylbenzylidene)acetohydrazide (16)

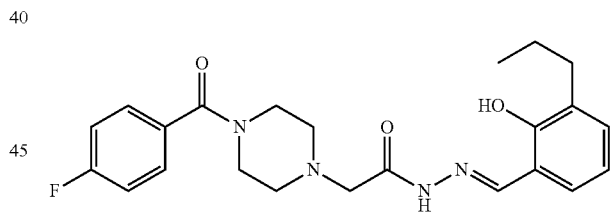

Synthesized according to General Procedure D: H12 (140 mg, 0.50 mmol, 1.0 equiv.), 47b (82 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 16 (133 mg, 62.4%) as a white solid. $^1$H-NMR (500 MHz, CDCl$_3$) δ 11.24 (br s, 1H), 10.17 (br s, 1H), 8.25 (s, 1H), 7.37 (dd, 2H, J=5.5, 8.5 Hz), 7.13 (dd, 1H, J=1.5, 7.5 Hz), 7.06 (t, 2H, J=8.5 Hz), 6.91 (dd, 1H, J=1.5, 7.5 Hz), 6.77 (t, 1H, J=7.5 Hz), 3.83 (br s, 2H), 3.49 (br s, 2H), 3.20 (s, 2H), 2.62-2.58 (m, 6H), 1.60 (sext, 2H, J=7.5 Hz), 0.91 (t, 3H, J=7.5 Hz). $^{13}$C-NMR (125 MHz, CDCl$_3$) δ 169.6, 165.4, 163.6 (d, $J_{C-F}$=249.3 Hz), 156.6, 151.7, 132.6, 131.4 (d, $J_{C-F}$=3.4 Hz), 129.5 (d, $J_{C-F}$=8.5 Hz), 128.9, 119.0, 116.7, 115.8 (d, $J_{C-F}$=21.8 Hz), 60.9, 53.5 (br), 47.7 (br), 42.2 (br), 31.9, 22.7, 14.1. $^{19}$F-NMR (470 MHz, CDCl$_3$) δ −112.8. HRMS (ESI): 427.2141 (M+1); calcd. for C$_{23}$H$_{28}$FN$_4$O$_3$: 427.2145.

N'-(2-hydroxy-3-propylbenzylidene)-2-(4-(4-(trifluoromethyl)benzyl)piperazin-1-yl)acetohydrazide (17)

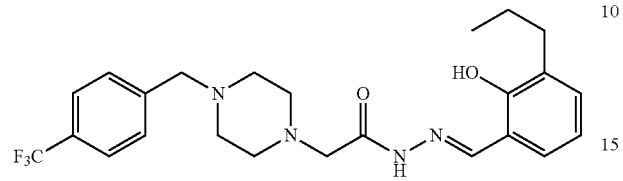

Synthesized according to General Procedure D: H13 (158 mg, 0.50 mmol, 1.0 equiv.), 47b (82 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 17 (93.9 mg, 40.6%) as a yellow solid. $^1$H-NMR (500 MHz, CDCl$_3$) δ 11.23 (br s, 1H), 10.05 (br s, 1H), 8.33 (s, 1H), 7.57 (d, 2H, J=8.0 Hz), 7.44 (d, 2H, J=8.0 Hz), 7.16 (dd, 1H, J=1.5, 7.5 Hz), 7.02 (dd, 2H, J=1.5, 7.5 Hz), 6.81 (t, 1H, J=7.5 Hz), 3.58 (s, 2H), 3.19 (s, 2H), 2.67-2.62 (m, 6H), 2.53 (br s, 4H), 1.65 (sext, 2H, J=7.5 Hz), 0.95 (t, 3H, J=7.5 Hz). $^{13}$C-NMR (125 MHz, CDCl$_3$) δ 165.9, 156.8, 151.5, 142.4, 132.6, 130.8, 129.6 (q, J$_{C-F}$=32.0 Hz), 129.3, 128.9, 125.4 (q, J$_{C-F}$=3.6 Hz), 124.4 (q, J$_{C-F}$=270.5 Hz), 119.0, 116.9, 62.4, 61.1, 53.8, 53.2, 32.0, 22.8, 14.2. $^{19}$F-NMR (470 MHz, CDCl$_3$) δ −65.5. HRMS (ESI): 463.2321 (M+1); calcd. for C$_{24}$H$_{30}$F$_3$N$_4$O$_2$: 463.2321.

N'-(2-hydroxy-3-propylbenzylidene)-2-(4-(4-(trifluoromethyl)benzoyl)piperazin-1-yl)acetohydrazide (18)

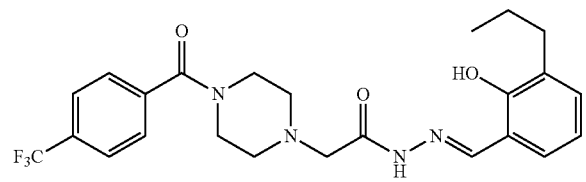 [SMILES: CCCc1cccc(/C=N/NC(=O)CN2CCN(C(=O)c3ccc(C(F)(F)F)cc3)CC2)c1O]

Synthesized according to General Procedure D: H14 (165 mg, 0.50 mmol, 1.0 equiv.), 47b (82 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 18 (216 mg, 90.8%) as a white solid. $^1$H-NMR (500 MHz, CDCl$_3$) δ 11.24 (br s, 1H), 10.14 (br s, 1H), 8.23 (s, 1H), 7.64 (d, 2H, J=8.0 Hz), 7.47 (d, 2H, J=8.0 Hz), 7.13 (d, 1H, J=8.0 Hz), 6.89 (d, 1H, J=7.5 Hz), 6.76 (t, 1H, J=7.5 Hz), 3.85 (br s, 2H), 3.43 (br s, 2H), 3.21 (s, 2H), 2.73-2.58 (m, 6H), 1.60 (sext, 2H, J=7.5 Hz), 0.90 (t, 3H, J=7.5 Hz). $^{13}$C-NMR (125 MHz, CDCl$_3$) δ 169.0, 165.4, 156.5, 151.6, 139.0, 132.7, 131.9 (q, J$_{C-F}$=32.5 Hz), 130.6, 128.8, 127.5, 125.8 (q, J$_{C-F}$=3.5 Hz), 123.7 (q, J$_{C-F}$=271.3 Hz), 119.0, 116.7, 60.8, 53.5 (br), 47.5 (br), 42.0 (br), 31.9, 22.7, 14.1. $^{19}$F-NMR (470 MHz, CDCl$_3$) δ −66.0. HRMS (ESI): 477.2108 (M+1); calcd. for C$_{24}$H$_{28}$F$_3$N$_4$O$_3$: 477.2114.

2-(4-benzylpiperazin-1-yl)-N'-(5-fluoro-2-hydroxybenzylidene)acetohydrazide (19)

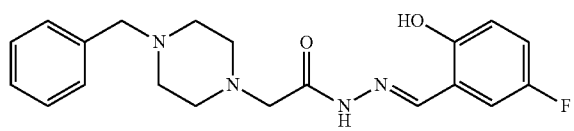 [SMILES: O=C(CN1CCN(Cc2ccccc2)CC1)N/N=C/c1cc(F)ccc1O]

Synthesized according to General Procedure D: H1 (124 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 19 (173 mg, 93.7%) as a white solid. $^1$H-NMR (500 MHz, CDCl$_3$) δ 10.81 (br s, 1H), 10.13 (br s, 1H), 8.39 (s, 1H), 7.33-7.30 (m, 4H), 7.28-7.25 (m, 1H), 7.00 (dt, 1H, J=3.0, 9.0 Hz), 6.94-6.89 (m, 2H), 3.55 (s, 2H), 3.19 (s, 2H), 2.63 (br s, 4H), 2.53 (br s, 4H). $^{13}$C-NMR (125 MHz, CDCl$_3$) δ 166.3, 155.9 (d, J$_{C-F}$=235.8 Hz), 154.8, 150.0, 137.9, 129.3, 128.5, 127.4, 118.9 (d, J$_{C-F}$=23.1 Hz), 118.4 (d, J$_{C-F}$=7.6 Hz), 117.6 (d, J$_{C-F}$=7.5 Hz), 116.1 (d, J$_{C-F}$=23.8 Hz), 63.0, 61.1, 53.9, 53.1. $^{19}$F-NMR (470 MHz, CDCl$_3$) δ −128.5. HRMS (ESI): 371.1877 (M+1); calcd. for C$_{20}$H$_{24}$FN$_4$O$_2$: 371.1883.

4-((4-(2-(2-(5-fluoro-2-hydroxybenzylidene)hydrazinyl)-2-oxoethyl)piperazin-1-yl)methyl)benzenesulfonamide (20)

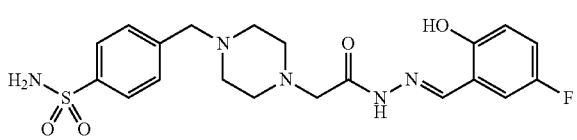 [SMILES: NS(=O)(=O)c1ccc(CN2CCN(CC(=O)N/N=C/c3cc(F)ccc3O)CC2)cc1]

Synthesized according to General Procedure D: H2 (164 mg, 0.50 mmol, 1.0 equiv.), 47c (70 mg, 0.50 mmol, 1.0 equiv.), 1.2 M HCl (29 μL, 0.035 mmol, 0.070 equiv.), 2:1 MeOH:MeCN (3 mL, 0.15 M). Purification by silica gel column chromatography (gradient, 0-20% MeOH/EtOAc) yielded 20 (172 mg, 82.1%) as a yellow solid. $^1$H-NMR (500 MHz, (CD$_3$)$_2$CO) δ 11.33 (br s, 1H), 10.95 (br s, 1H), 8.49 (s, 1H), 7.85 (d, 2H, J=8.0 Hz), 7.49 (d, 2H, J=8.0 Hz), 7.12 (dd, 1H, J=3.0, 9.0 Hz), 7.07 (dt, 1H, J=3.0, 8.5 Hz), 6.91 (dd, 1H, J=5.0, 9.0 Hz), 6.62 (br s, 2H), 3.55 (s, 2H), 3.19 (s, 2H), 2.59

(br s, 4H), 2.49 (br s, 4H). $^{13}$C-NMR (125 MHz, (CD$_3$)$_2$CO) δ 166.8, 156.4 (d, J$_{C-F}$=233.5 Hz), 155.4, 155.1 (d, J$_{C-F}$=2.8 Hz), 143.9, 143.6, 129.9, 126.7, 119.2 (d, J$_{C-F}$=7.6 Hz), 118.7 (d, J$_{C-F}$=17.8 Hz), 118.6, 116.6 (d, J$_{C-F}$=23.9 Hz), 62.5, 61.5, 54.1, 53.4. $^{19}$F-NMR (470 MHz, (CD$_3$)$_2$CO) δ −127.3. HRMS (ESI): 450.1609 (M+1); calcd. for C$_{20}$H$_{25}$FN$_5$O$_4$S: 450.1611.

2-(4-benzoylpiperazin-1-yl)-N'-(5-fluoro-2-hydroxybenzylidene)acetohydrazide (21)

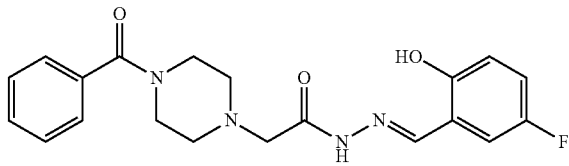 [SMILES: O=C(CN1CCN(C(=O)c2ccccc2)CC1)N/N=C/c1cc(F)ccc1O]

Synthesized according to General Procedure D: H3 (131 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 21 (157 mg, 81.6%) as a white solid. $^1$H-NMR (500 MHz, CDCl$_3$) δ 10.89 (br s, 1H), 10.50 (br s, 1H), 8.21 (s, 1H), 7.40-7.33 (m, 5H), 6.93 (dt, 1H, J=2.5, 8.5 Hz), 6.84 (dd, 1H, J=4.5, 9.0 Hz), 6.74 (dd, 1H, J=2.5, 8.5 Hz), 3.79 (br s, 2H), 3.48 (br s, 2H), 3.17 (s, 2H), 2.60 (br s, 2H), 2.53 (br s, 2H). $^{13}$C-NMR (125 MHz, CDCl$_3$) δ 170.5, 165.8, 155.7 (d, J$_{C-F}$=235.8 Hz), 154.5, 149.7, 135.3, 130.1, 128.7, 127.0, 118.8 (d, J$_{C-F}$=23.1 Hz), 118.2 (d, J$_{C-F}$=7.5 Hz), 117.6 (d, J$_{C-F}$=7.4 Hz), 116.0 (d, J$_{C-F}$=23.6 Hz), 60.7, 53.6 (br), 53.4 (br), 47.6 (br), 42.0 (br). $^{19}$F-NMR (470 MHz, CDCl$_3$) δ −128.3. HRMS (ESI): 385.1674 (M+1); calcd. for C$_{20}$H$_{22}$FN$_4$O$_3$: 385.1676.

2-(4-(4-cyanobenzyl)piperazin-1-yl)-N'-(5-fluoro-2-hydroxybenzylidene)acetohydrazide (22)

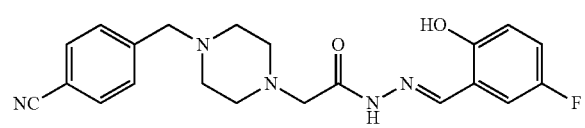 [SMILES: N#Cc1ccc(CN2CCN(CC(=O)N/N=C/c3cc(F)ccc3O)CC2)cc1]

Synthesized according to General Procedure D: H9 (137 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 22 (169 mg, 85.5%) as a white solid. $^1$H-NMR (500 MHz, CDCl$_3$) δ 10.84 (br s, 1H), 10.20 (br s, 1H), 8.31 (s, 1H), 7.56 (d, 2H, J=8.5 Hz), 7.41 (d, 1H, J=8.0 Hz), 6.95 (dt, 1H, J=3.0, 9.0 Hz), 6.88-6.85 (m, 2H), 3.54 (s, 2H), 3.18 (s, 2H), 2.60 (br s, 4H), 2.50 (br s, 4H). $^{13}$C-NMR (125 MHz, CDCl$_3$) δ 166.2, 155.7 (d, J$_{C-F}$=235.9 Hz), 154.6, 149.6, 144.0, 132.2, 129.5, 118.9 (d, J$_{C-F}$=22.6 Hz), 118.6, 118.2 (d, J$_{C-F}$=7.6 Hz), 117.5 (d, J$_{C-F}$=7.5 Hz), 116.0 (d, J$_{C-F}$=23.8 Hz), 110.9, 62.2, 61.0, 53.6, 53.0. $^{19}$F-NMR (470 MHz, CDCl$_3$) δ −128.4. HRMS (ESI): 396.1838 (M+1); calcd. for C$_{21}$H$_{23}$FN$_5$O$_2$: 396.1836.

2-(4-(4-cyanobenzoyl)piperazin-1-yl)-N'-(5-fluoro-2-hydroxybenzylidene)acetohydrazide (23)

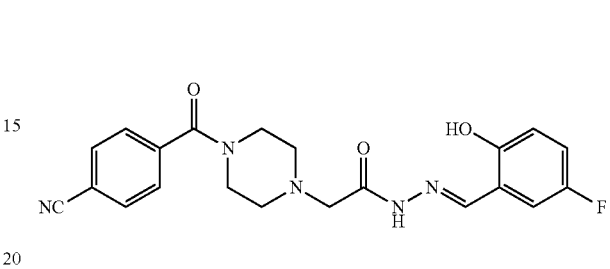

Synthesized according to General Procedure D: H10 (144 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 23 (144 mg, 70.1%) as a white solid. $^1$H-NMR (500 MHz, CDCl$_3$) δ 10.79 (br s, 1H), 10.16 (br s, 1H), 8.28 (s, 1H), 7.67 (d, 2H, J=8.0 Hz), 7.47 (d, 2H, J=8.5 Hz), 6.95 (dt, 1H, J=3.0, 8.0 Hz), 6.85 (dd, 1H, J=4.5, 9.0 Hz), 6.79 (dd, 1H, J=3.0, 8.5 Hz), 3.82 (br s, 2H), 3.41 (br s, 2H), 3.22 (s, 2H), 2.67 (br s, 2H), 2.54 (br s, 2H). $^{13}$C-NMR (125 MHz, CDCl$_3$) δ 168.4, 165.5, 155.7 (d, J$_{C-F}$=236.1 Hz), 154.5, 149.9, 139.7, 132.6, 127.8, 119.0 (d, J$_{C-F}$=23.1 Hz), 118.2 (d, J$_{C-F}$=7.6 Hz), 118.1, 117.4 (d, J$_{C-F}$=7.5 Hz), 116.0 (d, J$_{C-F}$=23.6 Hz), 113.7, 60.8, 53.4 (br), 52.7 (br), 47.4 (br), 42.0 (br). $^{19}$F-NMR (470 MHz, CDCl$_3$) δ −128.1. HRMS (ESI): 410.1623 (M+1); calcd. for C$_{21}$H$_{21}$FN$_5$O$_3$: 410.1628.

N'-(5-fluoro-2-hydroxybenzylidene)-2-(4-(4-fluorobenzyl)piperazin-1-yl)acetohydrazide (24)

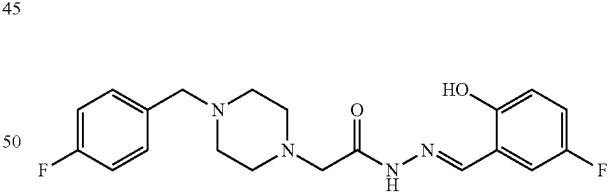

Synthesized according to General Procedure D: H11 (133 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 24 (152 mg, 78.2%) as a pale yellow solid. $^1$H-NMR (500 MHz, CDCl$_3$) δ 10.83 (br s, 1H), 10.19 (br s, 1H), 8.33 (s, 1H), 7.25 (dd, 2H, J=5.5, 8.5 Hz), 6.99-6.95 (m, 3H), 6.90-6.86 (m, 2H), 3.47 (s, 2H), 3.18 (s, 2H), 2.60 (br s, 4H), 2.49 (br s, 4H). $^{13}$C-NMR (125 MHz, CDCl$_3$) δ 166.3, 162.1 (d, J$_{C-F}$=243.9 Hz), 155.8 (d, J$_{C-F}$=236.0 Hz), 154.7 (d, J$_{C-F}$=1.4 Hz), 149.7 (d, J$_{C-F}$=2.6 Hz), 133.7 (d, J$_{C-F}$=3.0 Hz), 130.6 (d, J$_{C-F}$=7.9 Hz), 118.8 (d, J$_{C-F}$=23.3 Hz), 118.3 (d, J$_{C-F}$=7.6 Hz), 117.6 (d, J$_{C-F}$=7.5 Hz), 116.0 (d, J$_{C-F}$=23.8 Hz), 115.2 (d, J$_{C-F}$=21.1 Hz), 62.1, 61.0, 53.8, 52.9. $^{19}$F-NMR (470 MHz, CDCl$_3$) δ −118.8, −128.4. HRMS (ESI): 389.1787 (M+1); calcd. for C$_{20}$H$_{23}$F$_2$N$_4$O$_2$: 389.1789.

N'-(5-fluoro-2-hydroxybenzylidene)-2-(4-(4-fluorobenzoyl)piperazin-1-yl)acetohydrazide (25)

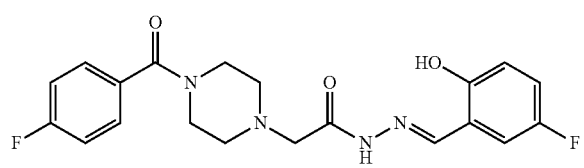 [SMILES: O=C(CN1CCN(C(=O)c2ccc(F)cc2)CC1)N/N=C/c1cc(F)ccc1O]

Synthesized according to General Procedure D: H12 (140 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 25 (101 mg, 50.1%) as a white solid. $^1$H-NMR (500 MHz, CDCl$_3$) δ 10.81 (br s, 1H), 10.25 (br s, 1H), 8.29 (s, 1H), 7.38 (dd, 2H, J=5.5, 8.5 Hz), 7.07 (t, 2H, J=8.5 Hz), 6.98-6.94 (m, 1H), 6.86 (dd, 1H, J=4.0, 9.0 Hz), 6.79 (dd, 1H, J=2.0, 8.0 Hz), 3.63 (br s, 4H), 3.21 (s, 2H), 2.59 (br s, 4H). $^{13}$C-NMR (125 MHz, CDCl$_3$) δ 169.7, 165.7, 163.6 (d, J$_{C-F}$=249.4 Hz), 155.8 (d, J$_{C-F}$=236.3 Hz), 154.6 (d, J$_{C-F}$=0.9 Hz), 150.0 (d, J$_{C-F}$=2.3 Hz), 131.3 (d, J$_{C-F}$=3.4 Hz), 129.5 (d, J$_{C-F}$=8.4 Hz), 119.0 (d, J$_{C-F}$=23.1 Hz), 118.3 (d, J$_{C-F}$=7.5 Hz), 117.5 (d, J$_{C-F}$=7.3 Hz), 116.0 (d, J$_{C-F}$=24.6 Hz), 115.8 (d, J$_{C-F}$=21.9 Hz), 60.9, 53.5, 47.7, 42.2. $^{19}$F-NMR (470 MHz, CDCl$_3$) δ −112.6, −128.2. HRMS (ESI): 403.1573 (M+1); calcd. for C$_{20}$H$_{21}$F$_2$N$_4$O$_3$: 403.1582.

N'-(5-fluoro-2-hydroxybenzylidene)-2-(4-(4-(trifluoromethyl)benzyl)piperazin-1-yl)acetohydrazide (26)

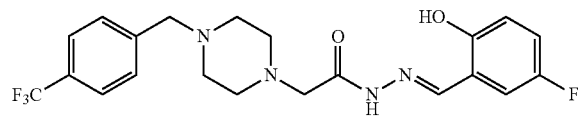 [SMILES: O=C(CN1CCN(Cc2ccc(C(F)(F)F)cc2)CC1)N/N=C/c1cc(F)ccc1O]

Synthesized according to General Procedure D: H13 (158 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 26 (194 mg, 88.6%) as a pale yellow solid. $^1$H-NMR (500 MHz, CDCl$_3$) δ 10.83 (br s, 1H), 10.17 (br s, 1H), 8.34 (s, 1H), 7.56 (d, 2H, J=8.0 Hz), 7.43 (d, 2H, J=8.0 Hz), 6.98 (dt, 1H, J=3.0, 8.0 Hz), 6.91-6.86 (m, 2H), 3.57 (s, 2H), 3.19 (s, 2H), 2.62 (br s, 4H), 2.52 (br s, 4H). $^{13}$C-NMR (125 MHz, CDCl$_3$) δ 166.3, 155.8 (d, J$_{C-F}$=236.0 Hz), 154.7 (d, J$_{C-F}$=1.5 Hz), 149.8 (d, J$_{C-F}$=2.4 Hz), 142.4 (d, J$_{C-F}$=0.8 Hz), 129.5 (q, J$_{C-F}$=32.1 Hz), 129.3, 125.3 (q, J$_{C-F}$=3.8 Hz), 124.4 (q, J$_{C-F}$=270.6 Hz), 118.9 (d, J$_{C-F}$=23.0 Hz), 118.3 (d, J$_{C-F}$=7.6 Hz), 117.6 (d, J$_{C-F}$=7.5 Hz), 116.1 (d, J$_{C-F}$=23.6 Hz), 62.3, 61.0, 53.8, 53.1. $^{19}$F-NMR (470 MHz, CDCl$_3$) δ −65.4, −128.4. HRMS (ESI): 439.1765 (M+1); calcd. for C$_{21}$H$_{23}$F$_4$N$_4$O$_2$: 439.1757.

N'-(5-fluoro-2-hydroxybenzylidene)-2-(4-(4-(trifluoromethyl)benzoyl)piperazin-1-yl)acetohydrazide (27)

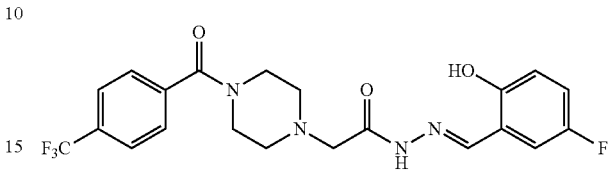

Synthesized according to General Procedure D: H14 (165 mg, 0.50 mmol, 1.0 equiv.), 47c (70 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 27 (173 mg, 76.5%) as a white solid. $^1$H-NMR (500 MHz, CDCl$_3$) δ 10.80 (br s, 1H), 10.20 (br s, 1H), 8.28 (s, 1H), 7.65 (d, 2H, J=8.0 Hz), 7.48 (d, 2H, J=7.5 Hz), 6.96 (dt, 1H, J=2.5, 8.0 Hz), 6.87 (dd, 1H, J=4.5, 8.5 Hz), 6.79 (dd, 1H, J=2.5, 8.0 Hz), 3.84 (br s, 2H), 3.44 (br s, 2H), 3.22 (s, 2H), 2.70 (br s, 2H), 2.55 (br s, 2H). $^{13}$C-NMR (125 MHz, CDCl$_3$) δ 169.1, 165.6, 155.8 (d, J$_{C-F}$=236.3 Hz), 154.6 (d, J$_{C-F}$=1.3 Hz), 150.0 (d, J$_{C-F}$=1.9 Hz), 138.9, 132.0 (q, J$_{C-F}$=32.6 Hz), 127.5, 125.8 (q, J$_{C-F}$=3.6 Hz), 123.7 (q, J$_{C-F}$=271.3 Hz), 119.0 (d, J$_{C-F}$=23.1 Hz), 118.3 (d, J$_{C-F}$=7.6 Hz), 117.4 (d, J$_{C-F}$=7.5 Hz), 116.0 (d, J$_{C-F}$=23.8 Hz), 60.8, 53.5 (br), 47.5 (br), 42.0 (br). $^{19}$F-NMR (470 MHz, CDCl$_3$) δ −66.0, −128.1. HRMS (ESI): 453.1552 (M+1); calcd. for C$_{21}$H$_{21}$F$_4$N$_4$O$_3$: 453.1550.

N'-(3-allyl-5-fluoro-2-hydroxybenzylidene)-2-(4-benzylpiperazin-1-yl)acetohydrazide (28)

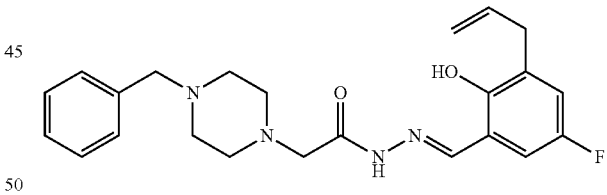

Synthesized according to General Procedure D: H1 (124 mg, 0.50 mmol, 1.0 equiv.), 47d (90 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 28 (186 mg, 90.8%) as a white solid. $^1$H-NMR (500 MHz, CDCl$_3$) δ 11.16 (s, 1H), 10.20 (br s, 1H), 8.28 (s, 1H), 7.34-7.30 (m, 4H), 7.28-7.25 (m, 1H), 6.91 (dd, 1H, J=3.0, 9.0 Hz), 6.74 (dd, 1H, J=3.0, 8.0 Hz), 5.98 (tdd, 1H, J=6.5, 10.0, 16.5 Hz), 5.13-5.08 (m, 2H), 3.54 (s, 2H), 3.42 (d, 2H, J=7.0 Hz), 3.20 (s, 2H), 2.63 (br s, 4H), 2.53 (br s, 4H). $^{13}$C-NMR (125 MHz, CDCl$_3$) δ 166.2, 155.5 (d, J$_{C-F}$=235.8 Hz), 152.5 (d, J$_{C-F}$=1.4 Hz), 149.8 (d, J$_{C-F}$=2.5 Hz), 137.9, 135.7, 130.2 (d, J$_{C-F}$=6.8 Hz), 129.2, 128.4, 127.3, 119.0 (d, J$_{C-F}$=23.1 Hz), 116.8 (d, J$_{C-F}$=7.9 Hz), 116.6, 113.9 (d, J$_{C-F}$=23.5 Hz), 62.9, 61.0, 53.8, 53.0, 33.8. $^{19}$F-NMR (470 MHz, CDCl$_3$) δ −128.6. HRMS (ESI): 411.2191 (M+1); calcd. for C$_{23}$H$_{28}$FN$_4$O$_2$: 411.2196.

4-((4-(2-(2-(3-allyl-5-fluoro-2-hydroxybenzylidene)hydrazinyl)-2-oxoethyl)piperazin-1-yl)methyl)benzenesulfonamide (29)

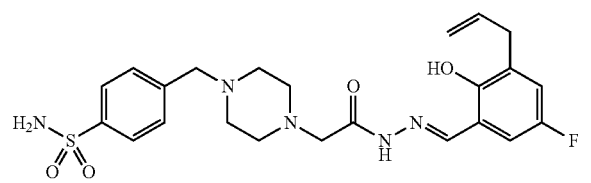 [SMILES: C=CCc1cc(F)cc(/C=N/NC(=O)CN2CCN(Cc3ccc(S(N)(=O)=O)cc3)CC2)c1O]

Synthesized according to General Procedure D: H2 (164 mg, 0.50 mmol, 1.0 equiv.), 47d (90 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-20% MeOH/EtOAc) yielded 29 (214 mg, 87.2%) as a white solid. $^1$H-NMR (500 MHz, (CD$_3$)$_2$CO) δ 11.73 (br s, 1H), 10.94 (br s, 1H), 8.46 (s, 1H), 7.85 (d, 2H, J=8.5 Hz), 7.48 (d, 2H, J=8.5 Hz), 6.96 (d, 2H, J=9.0 Hz), 6.62 (br s, 2H), 5.99 (tdd, 1H, J=6.5, 10.0, 16.5 Hz), 5.10 (qd, 1H, J=1.5, 17.0 Hz), 5.04 (qd, 2H, J=1.5, 10.0 Hz), 3.55 (s, 2H), 3.40 (d, 2H, J=7.0 Hz), 3.19 (s, 2H), 2.59 (br s, 4H), 2.49 (br s, 4H). $^{13}$C-NMR (125 MHz, (CD$_3$)$_2$CO) δ 166.8, 156.1 (d, J$_{C-F}$=233.6 Hz), 153.1 (d, J$_{C-F}$=1.3 Hz), 149.6, 143.9, 143.5, 136.6, 130.5 (d, J$_{C-F}$=7.0 Hz), 129.8, 126.7, 118.7 (d, J$_{C-F}$=23.1 Hz), 118.4 (d, J$_{C-F}$=8.0 Hz), 116.5, 114.6 (d, J$_{C-F}$=23.6 Hz), 62.5, 61.5, 54.1, 53.4, 34.2. $^{19}$F-NMR (470 MHz, (CD$_3$)$_2$CO) δ −127.4. HRMS (ESI): 490.1930 (M+1); calcd. for C$_{23}$H$_{29}$FN$_5$O$_4$S: 490.1924.

N'-(3-allyl-5-fluoro-2-hydroxybenzylidene)-2-(4-benzoylpiperazin-1-yl)acetohydrazide (30)

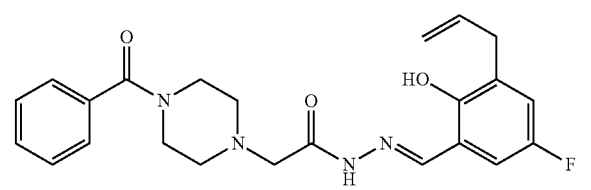 [SMILES: C=CCc1cc(F)cc(/C=N/NC(=O)CN2CCN(C(=O)c3ccccc3)CC2)c1O]

Synthesized according to General Procedure D: H3 (131 mg, 0.50 mmol, 1.0 equiv.), 47d (90 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-15% MeOH/EtOAc) yielded 30 (186 mg, 87.8%) as a white solid. $^1$H-NMR (500 MHz, CDCl$_3$) δ 11.17 (s, 1H), 10.45 (br s, 1H), 8.19 (s, 1H), 7.40-7.33 (m, 5H), 6.86 (dd, 1H, J=3.0, 9.0 Hz), 6.60 (dd, 1H, J=3.0, 8.5 Hz), 5.91 (tdd, 1H, J=6.5, 9.5, 18.0 Hz), 5.09-5.03 (m, 2H), 3.80 (br s, 2H), 3.47 (br s, 2H), 3.35 (d, 2H, J=6.5 Hz), 3.19 (s, 2H), 2.56 (br s, 4H). $^{13}$C-NMR (125 MHz, CDCl$_3$) δ 170.5, 165.6, 155.4 (d, J$_{C-F}$=235.5 Hz), 152.4 (d, J$_{C-F}$=1.4 Hz), 150.1 (d, J$_{C-F}$=1.8 Hz), 135.6, 135.3, 130.1, 130.1, 128.7, 127.0, 119.0 (d, J$_{C-F}$=23.0 Hz), 116.8 (d, J$_{C-F}$=7.9 Hz), 116.5, 113.9 (d, J$_{C-F}$=23.5 Hz), 60.7, 53.6 (br), 47.6 (br), 42.0 (br), 33.7. $^{19}$F-NMR (470 MHz, CDCl$_3$) δ −128.5. HRMS (ESI): 425.1991 (M+1); calcd. for C$_{23}$H$_{26}$FN$_4$O$_3$: 425.1989.

N'-(3-allyl-5-fluoro-2-hydroxybenzylidene)-2-(4-(4-cyanobenzyl)piperazin-1-yl)acetohydrazide (31)

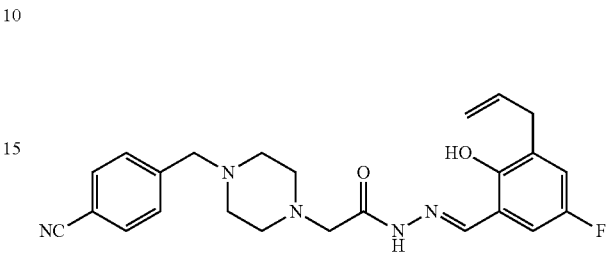

Synthesized according to General Procedure D: H9 (137 mg, 0.50 mmol, 1.0 equiv.), 47d (90 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-15% MeOH/EtOAc) yielded 31 (164 mg, 75.3%) as a white solid. $^1$H-NMR (500 MHz, CDCl$_3$) δ 11.12 (br s, 1H), 10.16 (br s, 1H), 8.28 (s, 1H), 7.57 (d, 2H, J=8.0 Hz), 7.42 (d, 2H, J=8.0 Hz), 6.88 (dd, 1H, J=3.0, 9.0 Hz), 6.72 (dd, 1H, J=3.0, 8.0 Hz), 5.94 (tdd, 1H, J=6.5, 10.0, 17.0 Hz), 5.09-5.05 (m, 2H), 3.55 (s, 2H), 3.38 (d, 2H, J=7.0 Hz), 3.19 (s, 2H), 2.62 (br s, 4H), 2.51 (br s, 4H). $^{13}$C-NMR (125 MHz, CDCl$_3$) δ 166.0, 155.5 (d, J$_{C-F}$=235.5 Hz), 152.5 (d, J$_{C-F}$=1.4 Hz), 149.9, 144.0, 135.7, 132.2, 130.1 (d, J$_{C-F}$=6.8 Hz), 129.5, 119.0 (d, J$_{C-F}$=23.0 Hz), 119.0, 116.8 (d, J$_{C-F}$=7.8 Hz), 116.5, 113.9 (d, J$_{C-F}$=23.5 Hz), 111.0, 62.3, 60.9, 53.8, 53.1, 33.8. $^{19}$F-NMR (470 MHz, CDCl$_3$) δ −128.6. HRMS (ESI): 436.2144 (M+1); calcd. for C$_{24}$H$_{27}$FN$_5$O$_2$: 436.2149.

N'-(3-allyl-5-fluoro-2-hydroxybenzylidene)-2-(4-(4-cyanobenzoyl)piperazin-1-yl)acetohydrazide (32)

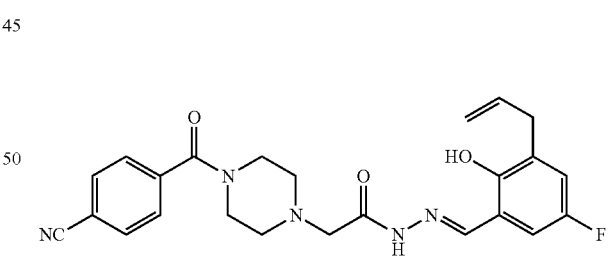

Synthesized according to General Procedure D: H10 (144 mg, 0.50 mmol, 1.0 equiv.), 47d (90 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-15% MeOH/EtOAc) yielded 32 (196 mg, 87.2%) as a white solid. $^1$H-NMR (500 MHz, CDCl$_3$) δ 11.10 (br s, 1H), 10.21 (br s, 1H), 8.20 (s, 1H), 7.65 (d, 2H, J=8.0 Hz), 7.45 (d, 2H, J=8.5 Hz), 6.84 (dd, 1H, J=3.0, 9.0 Hz), 6.61 (dd, 1H, J=3.0, 8.0 Hz), 5.88 (tdd, 1H, J=7.0, 10.0, 16.5 Hz), 5.03-5.00 (m, 2H), 3.81 (br s, 2H), 3.40 (br s, 2H), 3.31 (d, 2H, J=6.5 Hz), 3.21 (s, 2H), 2.66 (br s, 2H), 2.54 (br s, 2H).

$^{13}$C-NMR (125 MHz, CDCl$_3$) δ 168.3, 165.4, 155.4 (d, $J_{C-F}$=235.9 Hz), 152.3, 150.1, 139.7, 135.4, 132.5, 130.0 (d, $J_{C-F}$=6.8 Hz), 127.7, 119.1 (d, $J_{C-F}$=23.1 Hz), 118.0, 116.6 (d, $J_{C-F}$=7.9 Hz), 116.5, 113.8 (d, $J_{C-F}$=23.5 Hz), 113.6, 60.7, 53.3 (br), 47.3 (br), 42.0 (br), 33.6. $^{19}$F-NMR (470 MHz, CDCl$_3$) δ −128.3. HRMS (ESI): 450.1931 (M+1); calcd. for C$_{24}$H$_{25}$FN$_5$O$_3$: 450.1941.

N'-(3-allyl-5-fluoro-2-hydroxybenzylidene)-2-(4-(4-fluorobenzyl)piperazin-1-yl)acetohydrazide (33)

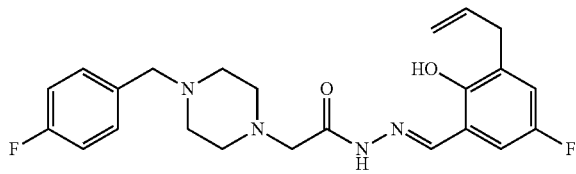 [SMILES: C=CCc1cc(F)cc(/C=N/NC(=O)CN2CCN(Cc3ccc(F)cc3)CC2)c1O]

Synthesized according to General Procedure D: H11 (133 mg, 0.50 mmol, 1.0 equiv.), 47d (90 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 33 (176 mg, 82.0%) as a yellow solid. $^1$H-NMR (500 MHz, CDCl$_3$) δ 11.15 (br s, 1H), 10.22 (br s, 1H), 8.26 (s, 1H), 7.25 (dd, 2H, J=5.5, 8.5 Hz), 6.98 (t, 2H, J=8.5 Hz), 6.89 (dd, 1H, J=3.0, 9.0 Hz), 6.72 (dd, 1H, J=3.0, 8.0 Hz), 5.95 (tdd, 1H, J=6.5, 10.0, 17.0 Hz), 5.10-5.06 (m, 2H), 3.47 (s, 2H), 3.39 (d, 2H, J=6.5 Hz), 3.18 (s, 2H), 2.61 (br s, 4H), 2.49 (br s, 4H). $^{13}$C-NMR (125 MHz, CDCl$_3$) δ 166.2, 162.1 (d, $J_{C-F}$=243.8 Hz), 155.5 (d, $J_{C-F}$=235.5 Hz), 152.5 (d, $J_{C-F}$=0.9 Hz), 149.8, 135.7, 133.6 (d, $J_{C-F}$=3.0 Hz), 130.6 (d, $J_{C-F}$=7.8 Hz), 130.1 (d, $J_{C-F}$=6.8 Hz), 119.0 (d, $J_{C-F}$=23.0 Hz), 116.8 (d, $J_{C-F}$=7.8 Hz), 116.5, 115.1 (d, $J_{C-F}$=21.0 Hz), 113.9 (d, $J_{C-F}$=23.5 Hz), 62.1, 61.0, 53.7, 52.9, 33.8. $^{19}$F-NMR (470 MHz, CDCl$_3$) δ −118.8, −128.6. HRMS (ESI): 429.2095 (M+1); calcd. for C$_{23}$H$_{27}$F$_2$N$_4$O$_2$: 429.2102.

N'-(3-allyl-5-fluoro-2-hydroxybenzylidene)-2-(4-(4-fluorobenzoyl)piperazin-1-yl)acetohydrazide (34)

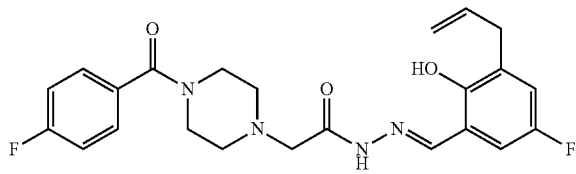 [SMILES: C=CCc1cc(F)cc(/C=N/NC(=O)CN2CCN(C(=O)c3ccc(F)cc3)CC2)c1O]

Synthesized according to General Procedure D: H12 (140 mg, 0.50 mmol, 1.0 equiv.), 47d (90 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 34 (163 mg, 73.8%) as a white solid. $^1$H-NMR (500 MHz, CDCl$_3$) δ 11.10 (br s, 1H), 10.23 (br s, 1H), 8.25 (s, 1H), 7.38 (dd, 2H, J=5.5, 8.5 Hz), 7.07 (t, 2H, J=8.5 Hz), 6.88 (dd, 1H, J=3.0, 9.0 Hz), 6.65 (dd, 1H, J=3.0, 8.5 Hz), 5.92 (tdd, 1H, J=6.5, 9.5, 17.0 Hz), 5.10-5.04 (m, 2H), 3.82 (br s, 2H), 3.50 (br s, 2H), 3.36 (d, 2H, J=6.5 Hz), 3.21 (s, 2H), 2.59 (br s, 4H). $^{13}$C-NMR (125 MHz, CDCl$_3$) δ 169.7, 165.6, 163.6 (d, $J_{C-F}$=249.8 Hz), 155.5 (d, $J_{C-F}$=235.6 Hz), 152.5 (d, $J_{C-F}$=1.4 Hz), 150.3 (d, $J_{C-F}$=2.5 Hz), 135.6, 131.3 (d, $J_{C-F}$=3.5 Hz), 130.2 (d, $J_{C-F}$=6.9 Hz), 129.5 (d, $J_{C-F}$=8.4 Hz), 119.2 (d, $J_{C-F}$=23.1 Hz), 116.7 (d, $J_{C-F}$=7.8 Hz), 116.6, 115.9 (d, $J_{C-F}$=21.8 Hz), 113.9 (d, $J_{C-F}$=23.5 Hz), 60.9, 53.6 (br), 47.7 (br), 42.2 (br), 33.8. $^{19}$F-NMR (470 MHz, CDCl$_3$) δ −112.6, −128.4. HRMS (ESI): 443.1886 (M+1); calcd. for C$_{23}$H$_{25}$F$_2$N$_4$O$_3$: 443.1895.

N'-(3-allyl-5-fluoro-2-hydroxybenzylidene)-2-(4-(4-(trifluoromethyl)benzyl)piperazin-1-yl)acetohydrazide (35)

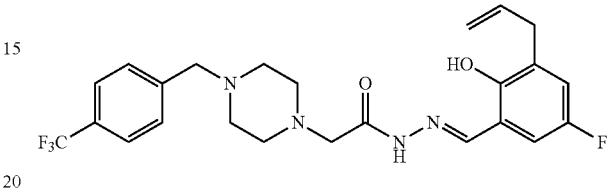

Synthesized according to General Procedure D: H13 (158 mg, 0.50 mmol, 1.0 equiv.), 47d (90 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 35 (176 mg, 73.7%) as a white solid. $^1$H-NMR (500 MHz, CDCl$_3$) δ 11.14 (br s, 1H), 10.19 (br s, 1H), 8.28 (s, 1H), 7.56 (d, 2H, J=8.0 Hz), 7.43 (d, 2H, J=8.0 Hz), 6.90 (dd, 1H, J=3.0, 9.0 Hz), 6.72 (dd, 2H, J=3.0, 8.0 Hz), 5.96 (tdd, 1H, J=6.5, 10.0, 17.0 Hz), 5.11-5.08 (m, 2H), 3.57 (s, 2H), 3.40 (d, 2H, J=6.5 Hz), 3.20 (s, 2H), 2.63 (br s, 4H), 2.53 (br s, 4H). $^{13}$C-NMR (125 MHz, CDCl$_3$) δ 166.1, 155.6 (d, $J_{C-F}$=235.5 Hz), 152.5 (d, $J_{C-F}$=1.3 Hz), 149.9 (d, $J_{C-F}$=2.4 Hz), 142.4, 135.7, 130.2 (d, $J_{C-F}$=6.8 Hz), 129.5 (q, $J_{C-F}$=32.0 Hz), 129.3, 125.3 (q, $J_{C-F}$=3.8 Hz), 124.4 (q, $J_{C-F}$=270.5 Hz), 119.1 (d, $J_{C-F}$=23.1 Hz), 116.9 (d, $J_{C-F}$=7.8 Hz), 116.6, 114.0 (d, $J_{C-F}$=23.5 Hz), 62.3, 61.0, 53.8, 53.1, 33.8. $^{19}$F-NMR (470 MHz, CDCl$_3$) δ −65.4, −128.5. HRMS (ESI): 479.2066 (M+1); calcd. for C$_{24}$H$_{27}$F$_4$N$_4$O$_2$: 479.2070.

N'-(3-allyl-5-fluoro-2-hydroxybenzylidene)-2-(4-(4-(trifluoromethyl)benzoyl)piperazin-1-yl)acetohydrazide (36)

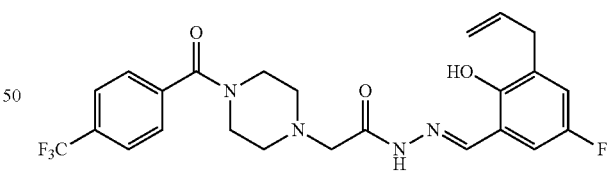

Synthesized according to General Procedure D: H14 (165 mg, 0.50 mmol, 1.0 equiv.), 47d (90 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-15% MeOH/EtOAc) yielded 36 (139 mg, 56.3%) as a white solid. $^1$H-NMR (500 MHz, CDCl$_3$) δ 11.07 (br s, 1H), 10.14 (br s, 1H), 8.26 (s, 1H), 7.66 (d, 2H, J=8.5 Hz), 7.50 (d, 2H, J=8.0 Hz), 6.89 (dd, 1H, J=3.0, 9.0 Hz), 6.66 (dd, 1H, J=3.0, 8.5 Hz), 5.93 (tdd, 1H, J=7.0, 10.0, 16.5 Hz), 5.10-5.04 (m, 2H), 3.86 (br s, 2H), 3.45 (br s, 2H), 3.37 (d, 2H, J=6.5 Hz), 3.23 (s, 2H), 2.69 (br s, 2H), 2.57 (br s, 2H). $^{13}$C-NMR (125 MHz, CDCl$_3$) δ 169.1, 165.5, 155.6 (d, $J_{C-F}$=235.9 Hz), 152.5, 150.4 (d, $J_{C-F}$=2.1 Hz), 138.9, 135.6, 132.0 (q, $J_{C-F}$=32.6 Hz), 130.3 (d, $J_{C-F}$=6.8 Hz), 127.5, 125.9 (q, $J_{C-F}$=3.8 Hz), 123.7 (q, $J_{C-F}$=271.1 Hz), 119.3 (d, $J_{C-F}$=23.0 Hz), 116.7 (d, $J_{C-F}$=4.6 Hz), 116.7, 114.0 (d, $J_{C-F}$=23.5 Hz), 60.9, 53.6 (br), 47.5 (br), 42.2 (br), 33.8. $^{19}$F-NMR (470 MHz, CDCl$_3$) δ –66.0, –128.4. HRMS (ESI): 493.1868 (M+1); calcd. for $C_{24}H_{25}F_4N_4O_3$: 493.1863.

2-(4-benzylpiperazin-1-yl)-N'-(5-fluoro-2-hydroxy-3-propylbenzylidene)acetohydrazide (37)

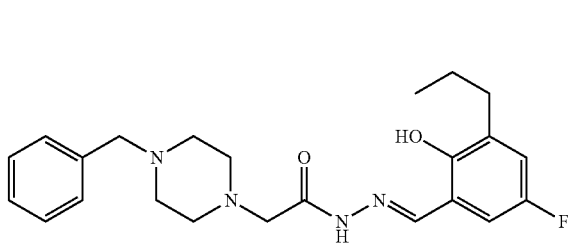 [SMILES: CCCc1cc(F)cc(/C=N/NC(=O)CN2CCN(Cc3ccccc3)CC2)c1O]

Synthesized according to General Procedure D: H1 (124 mg, 0.50 mmol, 1.0 equiv.), 47e (91 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-15% MeOH/EtOAc) yielded 37 (174 mg, 84.6%) as an off-white solid. $^1$H-NMR (500 MHz, CDCl$_3$) δ 11.10 (s, 1H), 10.19 (br s, 1H), 8.26 (s, 1H), 7.32-7.30 (m, 4H), 7.28-7.25 (m, 1H), 6.89 (dd, 1H, J=3.0, 9.0 Hz), 6.71 (dd, 1H, J=3.0, 8.5 Hz), 3.54 (s, 2H), 3.20 (s, 2H), 2.66-2.59 (m, 6H), 2.53 (br s, 4H), 1.64 (sext, 2H, J=7.5 Hz), 0.95 (t, 3H, J=7.5 Hz). $^{13}$C-NMR (125 MHz, CDCl$_3$) δ 166.1, 155.4 (d, $J_{C-F}$=235.1 Hz), 152.8, 150.0, 137.9, 132.7 (d, $J_{C-F}$=6.6 Hz), 129.2, 128.4, 127.3, 119.1 (d, $J_{C-F}$=22.5 Hz), 116.7 (d, $J_{C-F}$=7.9 Hz), 113.4 (d, $J_{C-F}$=23.4 Hz), 63.0, 61.0, 53.8, 53.1, 31.9, 22.5, 14.0. $^{19}$F-NMR (470 MHz, CDCl$_3$) δ –129.1. HRMS (ESI): 413.2345 (M+1); calcd. for $C_{23}H_{30}FN_4O_2$: 413.2353.

4-((4-(2-(2-(5-fluoro-2-hydroxy-3-propylbenzylidene)hydrazinyl)-2-oxoethyl)piperazin-1-yl)methyl)benzenesulfonamide (38)

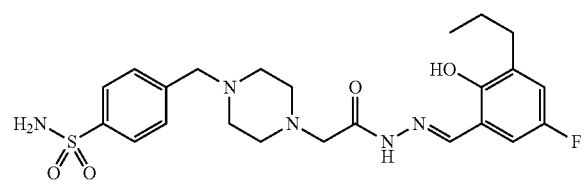 [SMILES: CCCc1cc(F)cc(/C=N/NC(=O)CN2CCN(Cc3ccc(S(N)(=O)=O)cc3)CC2)c1O]

Synthesized according to General Procedure D: H2 (164 mg, 0.50 mmol, 1.0 equiv.), 47e (91 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-20% MeOH/EtOAc) yielded 38 (221 mg, 89.9%) as a white solid. $^1$H-NMR (500 MHz, (CD$_3$)$_2$CO) δ 11.68 (br s, 1H), 10.92 (br s, 1H), 8.46 (s, 1H), 7.84 (d, 2H, J=8.0 Hz), 7.49 (d, 2H, J=8.0 Hz), 6.98 (dd, 1H, J=3.0, 9.5 Hz), 6.93 (dd, 1H, J=3.0, 8.5 Hz), 6.59 (br s, 2H), 3.57 (s, 2H), 3.18 (s, 2H), 2.64-2.59 (m, 6H), 2.50 (br s, 4H), 1.63 (sext, 2H, J=7.5 Hz), 0.93 (t, 3H, J=7.5 Hz). $^{13}$C-NMR (125 MHz, (CD$_3$)$_2$CO) δ 166.6, 156.1 (d, $J_{C-F}$=233.1 Hz), 153.4 (d, $J_{C-F}$=1.4 Hz), 149.7, 143.9, 143.6, 132.8 (d, $J_{C-F}$=2.9 Hz), 143.9, 143.6, 132.8 (d, $J_{C-F}$=6.9 Hz), 129.9, 126.8, 119.0 (d, $J_{C-F}$=22.8 Hz), 118.3 (d, $J_{C-F}$=8.1 Hz), 114.2 (d, $J_{C-F}$=23.6 Hz), 62.5, 61.6, 54.2, 53.4, 32.3, 23.1, 14.1. $^{19}$F-NMR (470 MHz, (CD$_3$)$_2$CO) δ –127.7. HRMS (ESI): 492.2074 (M+1); calcd. for $C_{23}H_{31}FN_5O_4S$: 492.2081.

2-(4-benzoylpiperazin-1-yl)-N'-(5-fluoro-2-hydroxy-3-propylbenzylidene)acetohydrazide (39)

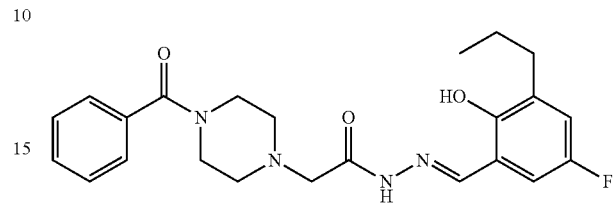

Synthesized according to General Procedure D: H3 (131 mg, 0.50 mmol, 1.0 equiv.), 47e (91 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-10% MeOH/EtOAc) yielded 39 (189 mg, 88.9%) as a white solid. $^1$H-NMR (500 MHz, CDCl$_3$) δ 11.13 (s, 1H), 10.48 (br s, 1H), 8.15 (s, 1H), 7.38-7.32 (m, 5H), 6.83 (dd, 1H, J=3.0, 9.0 Hz), 6.55 (dd, 1H, J=3.0, 8.5 Hz), 3.80 (br s, 2H), 3.46 (br s, 2H), 3.18 (s, 2H), 2.59-2.54 (m, 6H), 1.57 (sext, 2H, J=7.5 Hz), 0.88 (t, 3H, J=7.5 Hz). $^{13}$C-NMR (125 MHz, CDCl$_3$) δ 170.5, 165.6, 155.3 (d, $J_{C-F}$=235.1 Hz), 152.6 (d, $J_{C-F}$=1.4 Hz), 150.2 (d, $J_{C-F}$=2.5 Hz), 135.3, 132.5 (d, $J_{C-F}$=6.8 Hz), 130.1, 128.7, 126.9, 119.1 (d, $J_{C-F}$=22.6 Hz), 116.6 (d, $J_{C-F}$=7.9 Hz), 113.4 (d, $J_{C-F}$=23.4 Hz), 60.7, 53.5 (br), 47.5 (br), 42.0 (br), 31.8, 22.4, 13.9. $^{19}$F-NMR (470 MHz, CDCl$_3$) δ –129.0. HRMS (ESI): 427.2144 (M+1); calcd. for $C_{23}H_{28}FN_4O_3$: 427.2145.

2-(4-(4-cyanobenzyl)piperazin-1-yl)-N'-(5-fluoro-2-hydroxy-3-propylbenzylidene)acetohydrazide (40)

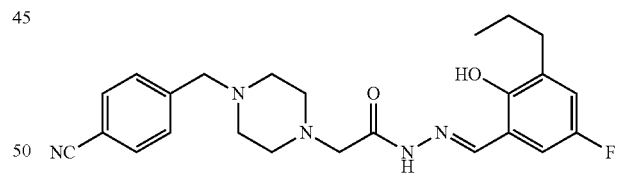

Synthesized according to General Procedure D: H9 (137 mg, 0.50 mmol, 1.0 equiv.), 47e (91 mg, 0.50 mmol, 1.0 equiv.), 1.2 M HCl (29 µL, 0.035 mmol, 0.070 equiv.), EtOH (3 mL, 0.15 M). Purification by silica gel column chromatography (gradient, 0-15% MeOH/EtOAc) yielded 40 (180 mg, 82.1%) as a white solid. $^1$H-NMR (500 MHz, CDCl$_3$) δ 11.07 (br s, 1H), 10.16 (br s, 1H), 8.25 (s, 1H), 7.57 (d, 2H, J=8.5 Hz), 7.42 (d, 2H, J=8.0 Hz), 6.86 (dd, 1H, J=3.0, 9.0 Hz), 6.68 (dd, 1H, J=3.0, 8.0 Hz), 3.55 (s, 2H), 3.18 (s, 2H), 2.70-2.57 (m, 6H), 2.51 (br s, 4H). $^{13}$C-NMR (125 MHz, CDCl$_3$) δ 166.0, 155.4 (d, $J_{C-F}$=235.1 Hz), 152.7 (d, $J_{C-F}$=1.4 Hz), 150.0 (d, $J_{C-F}$=2.5 Hz), 144.0, 132.6 (d, $J_{C-F}$=6.8 Hz), 132.2, 129.5, 119.1 (d, $J_{C-F}$=22.6 Hz), 119.0, 116.6 (d, $J_{C-F}$=8.0 Hz), 113.4 (d, $J_{C-F}$=23.5 Hz), 110.9, 62.3, 60.9, 53.7, 53.1, 31.9, 22.4, 14.0. $^{19}$F-NMR (470 MHz, CDCl$_3$) δ −129.0. HRMS (ESI): 438.2301 (M+1); calcd. for C$_{24}$H$_{29}$FN$_5$O$_2$: 438.2305.

2-(4-(4-cyanobenzoyl)piperazin-1-yl)-N'-(5-fluoro-2-hydroxy-3-propylbenzylidene)acetohydrazide (41)

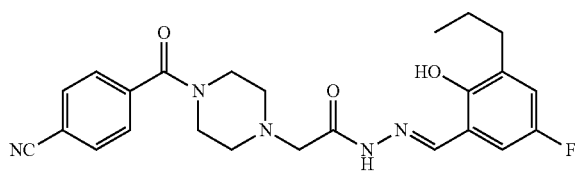 [SMILES: CCCc1cc(F)cc(/C=N/NC(=O)CN2CCN(C(=O)c3ccc(C#N)cc3)CC2)c1O]

Synthesized according to General Procedure D: H10 (144 mg, 0.50 mmol, 1.0 equiv.), 47e (91 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-10% MeOH/EtOAc) yielded 41 (196 mg, 86.5%) as a white solid. $^1$H-NMR (500 MHz, CDCl$_3$) δ 11.03 (br s, 1H), 10.17 (br s, 1H), 8.19 (s, 1H), 7.66 (d, 2H, J=8.0 Hz), 7.46 (d, 2H, J=8.0 Hz), 6.84 (dd, 1H, J=3.0, 9.0 Hz), 6.59 (dd, 1H, J=3.0, 8.5 Hz), 3.82 (br s, 2H), 3.41 (br s, 2H), 3.22 (s, 2H), 2.66 (br s, 2H), 2.57-2.52 (m, 2H), 1.55 (sext, 2H, J=7.5 Hz), 0.87 (t, 3H, J=7.5 Hz). $^{13}$C-NMR (125 MHz, CDCl$_3$) δ 168.3, 165.4, 155.3 (d, J$_{C-F}$=235.5 Hz), 152.6 (d, J$_{C-F}$=1.1 Hz), 150.3 (d, J$_{C-F}$=2.0 Hz), 139.7, 132.6 (d, J$_{C-F}$=6.8 Hz), 132.5, 127.7, 119.2 (d, J$_{C-F}$=22.6 Hz), 118.0, 116.4 (d, J$_{C-F}$=7.9 Hz), 113.6, 113.4 (d, J$_{C-F}$=23.3 Hz), 60.7, 53.4 (br), 47.4 (br), 42.0 (br), 31.7, 22.3, 13.9. $^{19}$F-NMR (470 MHz, CDCl$_3$) δ −128.7. HRMS (ESI): 452.2098 (M+1); calcd. for C$_{24}$H$_{27}$FN$_5$O$_3$: 452.2098.

N'-(5-fluoro-2-hydroxy-3-propylbenzylidene)-2-(4-(4-fluorobenzyl)piperazin-1-yl)acetohydrazide (42)

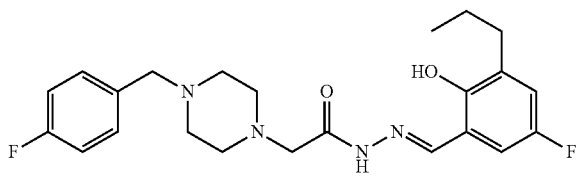 [SMILES: CCCc1cc(F)cc(/C=N/NC(=O)CN2CCN(Cc3ccc(F)cc3)CC2)c1O]

Synthesized according to General Procedure D: H11 (133 mg, 0.50 mmol, 1.0 equiv.), 47e (91 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 42 (202 mg, 93.8%) as a yellow solid. $^1$H-NMR (500 MHz, CDCl$_3$) δ 11.07 (br s, 1H), 10.16 (br s, 1H), 8.26 (s, 1H), 7.26 (dd, 2H, J=5.5, 8.5 Hz), 6.99 (t, 2H, J=8.5 Hz), 6.88 (dd, 1H, J=3.0, 9.0 Hz), 6.70 (dd, 1H, J=3.0, 8.0 Hz), 3.48 (s, 2H), 3.18 (s, 2H), 2.66-2.58 (m, 6H), 2.50 (br s, 4H), 1.62 (sext, 2H, J=7.5 Hz), 0.94 (t, 3H, J=7.5 Hz). $^{13}$C-NMR (125 MHz, CDCl$_3$) δ 166.1, 162.1 (d, J$_{C-F}$=243.8 Hz), 155.5 (d, J$_{C-F}$=235.0 Hz), 152.8 (d, J$_{C-F}$=0.9 Hz), 150.1 (d, J$_{C-F}$=2.0 Hz), 133.7, 132.7 (d, J$_{C-F}$=6.8 Hz), 130.7 (d, J$_{C-F}$=7.9 Hz), 119.2 (d, J$_{C-F}$=22.5 Hz), 116.7 (d, J$_{C-F}$=7.9 Hz), 115.2 (d, J$_{C-F}$=21.0 Hz), 113.5 (d, J$_{C-F}$=23.4 Hz), 62.1, 61.0, 53.8, 53.0, 31.9, 22.5, 14.1.

$^{19}$F-NMR (470 MHz, CDCl$_3$) δ −118.8, −129.0. HRMS (ESI): 431.2250 (M+1); calcd. for C$_{23}$H$_{29}$F$_2$N$_4$O$_2$: 431.2259.

N'-(5-fluoro-2-hydroxy-3-propylbenzylidene)-2-(4-(4-fluorobenzoyl)piperazin-1-yl)acetohydrazide (43)

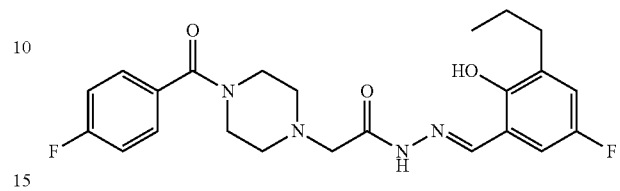

Synthesized according to General Procedure D: H12 (140 mg, 0.50 mmol, 1.0 equiv.), 47e (91 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-10% MeOH/EtOAc) yielded 43 (195 mg, 87.7%) as a white solid. $^1$H-NMR (500 MHz, CDCl$_3$) δ 11.07 (br s, 1H), 10.32 (br s, 1H), 8.18 (s, 1H), 7.36 (dd, 2H, J=5.0, 8.5 Hz), 7.05 (t, 2H, J=8.5 Hz), 6.84 (dd, 1H, J=3.0, 9.0 Hz), 6.57 (dd, 1H, J=3.0, 8.5 Hz), 3.81 (br s, 2H), 3.48 (br s, 2H), 3.20 (s, 2H), 2.62-2.50 (m, 6H), 1.56 (sext, 2H, J=7.5 Hz), 0.88 (t, 3H, J=7.5 Hz). $^{13}$C-NMR (125 MHz, CDCl$_3$) δ 169.6, 165.6, 163.5 (d, J$_{C-F}$=249.3 Hz), 155.4 (d, J$_{C-F}$=235.4 Hz), 152.7 (d, J$_{C-F}$=0.9 Hz), 150.3, 132.6 (d, J$_{C-F}$=6.8 Hz), 131.3 (d, J$_{C-F}$=3.4 Hz), 129.4 (d, J$_{C-F}$=8.4 Hz), 119.2 (d, J$_{C-F}$=22.6 Hz), 116.5 (d, J$_{C-F}$=7.9 Hz), 115.8 (d, J$_{C-F}$=21.6 Hz), 113.4 (d, J$_{C-F}$=23.4 Hz), 60.7, 53.5 (br), 47.7 (br), 42.1 (br), 31.8, 22.4, 13.9. $^{19}$F-NMR (470 MHz, CDCl$_3$) δ −112.6, −128.8. HRMS (ESI): 445.2049 (M+1); calcd. for C$_{23}$H$_{27}$F$_2$N$_4$O$_3$: 445.2051.

N'-(5-fluoro-2-hydroxy-3-propylbenzylidene)-2-(4-(4-(trifluoromethyl)benzyl)piperazin-1-yl)acetohydrazide (44)

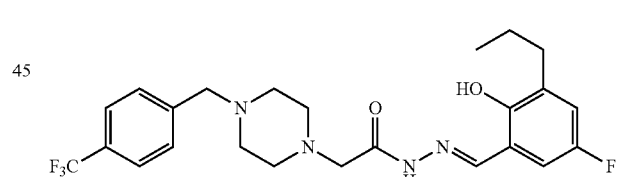

Synthesized according to General Procedure D: H13 (158 mg, 0.50 mmol, 1.0 equiv.), 47e (91 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-20% MeOH/EtOAc) yielded 44 (184 mg, 76.5%) as a light yellow solid. $^1$H-NMR (500 MHz, CDCl$_3$) δ 11.08 (br s, 1H), 10.18 (br s, 1H), 8.25 (s, 1H), 7.56 (d, 2H, J=8.0 Hz), 7.43 (d, 2H, J=8.0 Hz), 6.88 (dd, 1H, J=3.0, 9.0 Hz), 6.69 (dd, 2H, J=3.0, 8.5 Hz), 3.56 (s, 2H), 3.20 (s, 2H), 2.64-2.58 (m, 6H), 2.52 (br s, 4H), 1.62 (sext, 2H, J=7.5 Hz), 0.93 (t, 3H, J=7.5 Hz). $^{13}$C-NMR (125 MHz, CDCl$_3$) δ 166.1, 155.5 (d, J$_{C-F}$=235.1 Hz), 152.8 (d, J$_{C-F}$=1.2 Hz), 150.0 (d, J$_{C-F}$=2.6 Hz), 142.4, 132.7 (d, J$_{C-F}$=6.8 Hz), 129.5 (q, J$_{C-F}$=32.1 Hz), 129.3, 125.3 (q, J$_{C-F}$=3.8 Hz), 124.4 (q, J$_{C-F}$=270.5 Hz), 119.2 (d, J$_{C-F}$=22.6 Hz), 116.7 (d, J$_{C-F}$=7.9 Hz), 113.5 (d, J$_{C-F}$=23.5 Hz), 62.3, 61.0, 53.8, 53.1, 31.9, 22.5, 14.0. $^{19}$F-NMR (470 MHz, CDCl$_3$) δ −65.4, −128.9. HRMS (ESI): 481.2216 (M+1); calcd. for C$_{24}$H$_{29}$F$_4$N$_4$O$_2$: 481.2227.

N'-(5-fluoro-2-hydroxy-3-propylbenzylidene)-2-(4-(4-(trifluoromethyl)benzoyl)piperazin-1-yl)acetohydrazide (45)

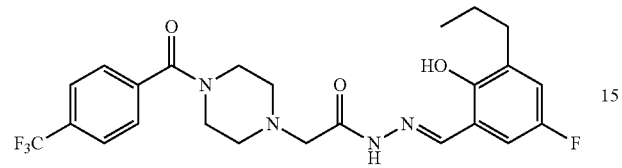

Synthesized according to General Procedure D: H14 (165 mg, 0.50 mmol, 1.0 equiv.), 47e (91 mg, 0.50 mmol, 1.0 equiv.), 1.2 M HCl (29 μL, 0.035 mmol, 0.070 equiv.), EtOH (3 mL, 0.15 M). Purification by silica gel column chromatography (gradient, 0-10% MeOH/EtOAc) yielded 45 (140 mg, 56.7%) as a white solid. $^1$H-NMR (500 MHz, CDCl$_3$) δ 11.04 (br s, 1H), 10.19 (br s, 1H), 8.21 (s, 1H), 7.65 (d, 2H, J=8.5 Hz), 7.48 (d, 2H, J=8.0 Hz), 6.86 (dd, 1H, J=3.0, 9.0 Hz), 6.60 (dd, 1H, J=3.0, 8.0 Hz), 3.85 (br s, 2H), 3.44 (br s, 2H), 3.22 (s, 2H), 2.67 (br s, 2H), 2.60-2.51 (m, 4H), 1.58 (sext, 2H, J=7.5 Hz), 0.90 (t, 3H, J=7.5 Hz). $^{13}$C-NMR (125 MHz, CDCl$_3$) δ 169.0, 165.5, 155.4 (d, $J_{C-F}$=235.4 Hz), 152.7 (d, $J_{C-F}$=0.9 Hz), 150.4 (d, $J_{C-F}$=2.4 Hz), 138.9, 132.7 (d, $J_{C-F}$=6.8 Hz), 132.0 (q, $J_{C-F}$=32.6 Hz), 127.5, 125.8 (q, $J_{C-F}$=3.6 Hz), 123.7 (q, $J_{C-F}$=271.0 Hz), 119.3 (d, $J_{C-F}$=22.6 Hz), 116.5 (d, $J_{C-F}$=7.9 Hz), 113.4 (d, $J_{C-F}$=23.4 Hz), 60.8, 53.5 (br), 47.5 (br), 42.0 (br), 31.8, 22.4, 14.0. $^{19}$F-NMR (470 MHz, CDCl$_3$) δ −66.0, −128.7. HRMS (ESI): 495.2008 (M+1); calcd. for C$_{24}$H$_{27}$F$_4$N$_4$O$_3$: 495.2019.

Scheme 3.1: Examples of starting materials used for synthesis of various hydrazides.

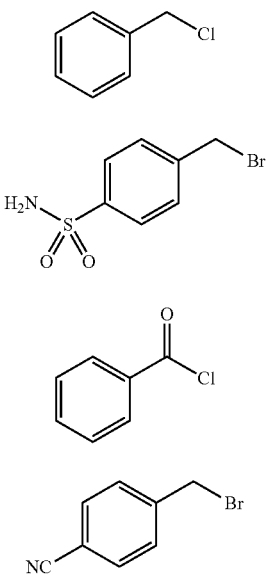

54a

54b

54c

54d

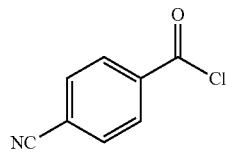

54e

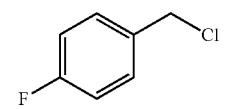

54f

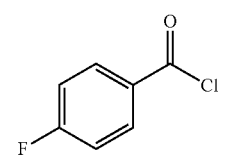

54g

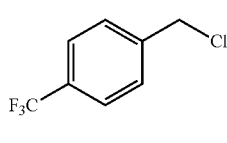

54h

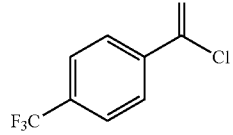

54i

Example 3

Citations

1. Putt, K. S.; Chen, G. W.; Pearson, J. M.; Sandhorst, J. S.; Hoagland, M. S.; Kwon, J. T.; Hwang, S. K.; Jin, H.; Churchwell, M. I.; Cho, M. H.; Doerge, D. R.; Helferich, W. G.; Hergenrother, P. J., Small-molecule activation of procaspase-3 to caspase-3 as a personalized anticancer strategy. *Nat. Chem. Biol.* 2006, 2, 543-550.
2. Peterson, Q. P.; Hsu, D. C.; Goode, D. R.; Novotny, C. J.; Totten, R. K.; Hergenrother, P. J., Procaspase-3 Activation as an Anti-Cancer Strategy: Structure-Activity Relationship of Procaspase-Activating Compound 1 (PAC-1) and Its Cellular Co-Localization with Caspase-3. *J. Med. Chem.* 2009, 52, 5721-5731.
3. Hsu, D. C.; Roth, H. S.; West, D. C.; Botham, R. C.; Novotny, C. J.; Schmid, S. C.; Hergenrother, P. J., Parallel Synthesis and Biological Evaluation of 837 Analogues of Procaspase-Activating Compound 1 (PAC-1). *ACS Comb. Sci.* 2012, 14, 44-50.
4. Vichai, V.; Kirtikara, K., Sulforhodamine B colorimetric assay for cytotoxicity screening. *Nat. Protoc.* 2006, 1, 1112-1116.

Example 5

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound that directly activates procaspase-3 upon contacting procaspase-3, wherein the compound is a compound of Formula I:

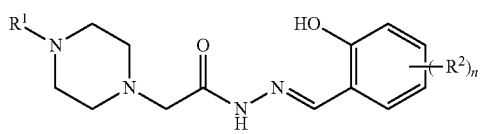

wherein
 $R^1$ is an optionally substituted benzoyl;
 n is 1, 2, 3, or 4; and
 each $R^2$ is independently H, alkyl, alkoxy, hydroxy, carboxy, halo, amino, alkylamino, dialkylamino, trifluoromethyl, trifluoromethoxy, benzyl, benzyloxy, nitro, cyano (—CN), sulfonamide (—$SO_2NH_2$), 2-propenyl, acetylene, N-alkyl-triazole, or N-benzyl-triazole; or two $R^2$ groups form an ortho-fused benzo group;
 or a pharmaceutically acceptable salt or solvate thereof.

2. The compound of claim 1 wherein n is 1 or 2.

3. The compound of claim 1 wherein $R^2$ is methyl, t-butyl, methoxy, hydroxy, fluoro, chloro, bromo, iodo, amino, ethylamino, diethylamino, trifluoromethoxy, benzyl, benzyloxy, nitro, 2-propenyl, acetylene, N-methyl-triazole, or N-benzyl-triazole.

4. The compound of claim 1 wherein n is 2 and two $R^2$ groups form an ortho-fused benzo group.

5. The compound of claim 1 wherein n is 2 and each $R^2$ is t-butyl.

6. The compound of claim 1 wherein n is 1 and $R^2$ is 2-propenyl.

7. The compound of claim 1 wherein $R^1$ is a methoxy-benzoyl; dimethoxy-benzoyl; benzyloxy-benzoyl; t-butyl-benzoyl; naphthylcarbonyl; or ethyl-benzoyl.

8. The compound of claim 1 wherein $R^1$ is 4 methoxy-benzoyl; 2,5-dimethoxy-benzoyl; 4-benzyloxy-benzoyl; 4-t-butyl-benzoyl; 2-naphthylcarbonyl; or 4-ethyl-benzoyl.

9. The compound of claim 1 wherein $R^1$ is:

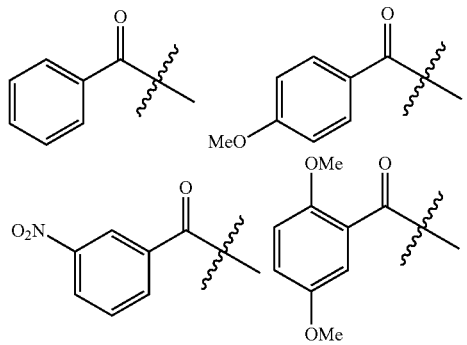

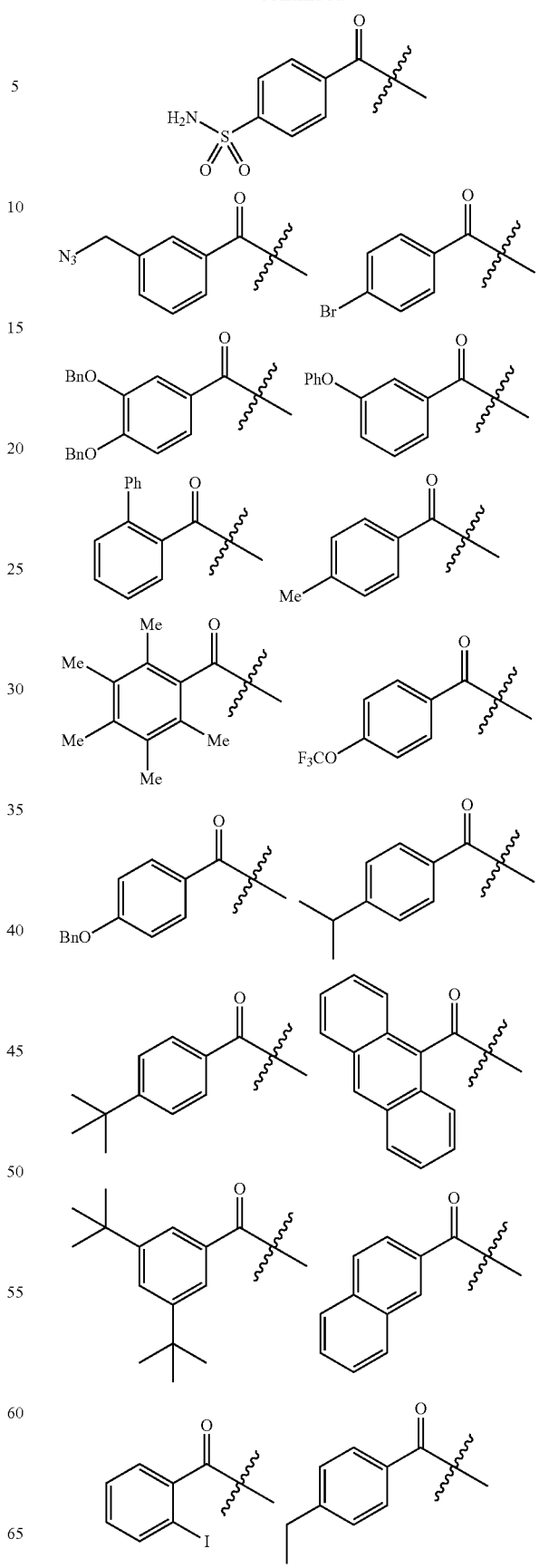

-continued

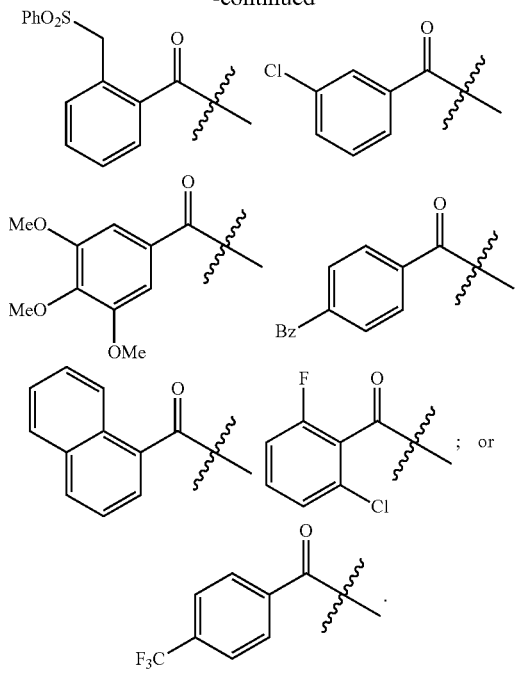

10. The compound of claim 1 wherein the compound is:

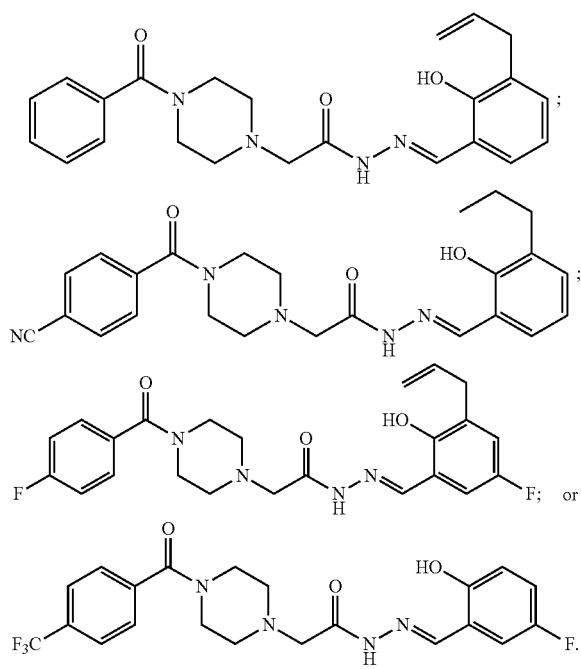

11. The compound of claim 1 wherein the compound induces death of cancer cells in culture.

12. A pharmaceutical composition comprising a compound of claim 1 and a pharmaceutically acceptable diluent, excipient, or carrier.

13. A method of inducing apoptosis in a cancer cell comprising administering to a cancer cell an effective amount of a compound of claim 1.

14. A compound of claim 1 wherein the compound is a compound of Formula (X):

(X)

wherein
$R^{10}$ is H, F, Cl, Br, —$NO_2$, —CN, —$CF_3$, —$OCF_3$, or —$SO_2NH_2$;
$R^{20}$ is H, F, Cl, Br, —$NO_2$, —CN, —$CF_3$, —$OCF_3$, or —$SO_2NH_2$; and
$R^{30}$ is H, ($C_1$-$C_6$)alkyl, ($C_1$-$C_6$)alkenyl, or ($C_1$-$C_6$)alkoxy;
or a pharmaceutically acceptable salt or solvate thereof.

15. The compound of claim 14 wherein $R^{30}$ is H, propyl, or 2-propenyl.

16. A pharmaceutical composition comprising a compound of claim 14 and a pharmaceutically acceptable diluent, excipient, or carrier.

17. A method of inducing apoptosis in a cancer cell comprising administering to a cancer cell an effective amount of a compound of claim 14.

18. The method of claim 17 wherein the cancer cell is an adrenal cancer cell, a brain cancer cell, a breast cancer cell, a colon cancer cell, a kidney cancer cell, a lymphoma cell, a leukemia cell, a liver cancer cell, a lung cancer cell, a melanoma cell, a neuroblastoma cell, a pancreatic cancer cell, a prostate cancer cell, or a renal cancer cell.

19. The method of claim 13 wherein the cancer cell is an adrenal cancer cell, a brain cancer cell, a breast cancer cell, a colon cancer cell, a kidney cancer cell, a lymphoma cell, a leukemia cell, a liver cancer cell, a lung cancer cell, a melanoma cell, a neuroblastoma cell, a pancreatic cancer cell, a prostate cancer cell, or a renal cancer cell.

* * * * *

UNITED STATES PATENT AND TRADEMARK OFFICE
CERTIFICATE OF CORRECTION

| | | |
|---|---|---|
| PATENT NO. | : 9,249,116 B2 | Page 1 of 1 |
| APPLICATION NO. | : 14/417524 | |
| DATED | : February 2, 2016 | |
| INVENTOR(S) | : Paul J. Hergenrother and Howard S. Roth | |

It is certified that error appears in the above-identified patent and that said Letters Patent is hereby corrected as shown below:

In the specification,

Add the following paragraph at column 1, line 12, before the BACKGROUND OF THE INVENTION heading:

GOVERNMENT SUPPORT

This invention was made with government support under Grant No. R01CA120439 awarded by the National Institutes of Health. The government has certain rights in the invention.

Signed and Sealed this
Nineteenth Day of April, 2016

Michelle K. Lee
*Director of the United States Patent and Trademark Office*